US011089767B2

(12) United States Patent
Lewis et al.

(10) Patent No.: US 11,089,767 B2
(45) Date of Patent: Aug. 17, 2021

(54) TRANSGENIC SILKWORMS EXPRESSING SPIDER SILK

(71) Applicants: Randolph V. Lewis, Nibley, UT (US); Lijin Xia, North Logan, UT (US); Xiaoli Zhang, North Logan, UT (US); Justin A. Jones, Nibley, UT (US)

(72) Inventors: Randolph V. Lewis, Nibley, UT (US); Lijin Xia, North Logan, UT (US); Xiaoli Zhang, North Logan, UT (US); Justin A. Jones, Nibley, UT (US)

(73) Assignee: Utah State University

( * ) Notice: Subject to any disclaimer, the term of this patent is extended or adjusted under 35 U.S.C. 154(b) by 97 days.

(21) Appl. No.: 15/942,185

(22) Filed: Mar. 30, 2018

(65) Prior Publication Data

US 2018/0288988 A1 Oct. 11, 2018

Related U.S. Application Data

(60) Provisional application No. 62/479,156, filed on Mar. 30, 2017.

(51) Int. Cl.

| | |
|---|---|
| ***A01K 67/033*** | (2006.01) |
| ***A01K 67/04*** | (2006.01) |
| ***C12N 15/85*** | (2006.01) |
| ***C07K 14/435*** | (2006.01) |
| ***C12P 21/02*** | (2006.01) |
| ***C12N 15/90*** | (2006.01) |

(52) U.S. Cl.

CPC ...... *A01K 67/0335* (2013.01); *A01K 67/0339* (2013.01); *A01K 67/04* (2013.01); *C07K 14/43518* (2013.01); *C07K 14/43586* (2013.01); *C12N 15/8509* (2013.01); *C12N 15/90* (2013.01); *C12P 21/02* (2013.01); *A01K 2217/052* (2013.01); *A01K 2227/706* (2013.01); *A01K 2267/01* (2013.01)

(58) Field of Classification Search

CPC .................................................. A01K 67/0335

See application file for complete search history.

(56) References Cited

U.S. PATENT DOCUMENTS

| | | | | |
|---|---|---|---|---|
| 6,872,869 | B2 | 3/2005 | Liu | |
| 9,131,671 | B2 * | 9/2015 | Brigham | A01K 67/0339 |
| 2013/0178602 | A1 | 7/2013 | Zhao | |
| 2013/0212718 | A1 | 8/2013 | Fraser | |
| 2014/0093965 | A1 * | 4/2014 | Lewis | C12P 21/02 435/471 |
| 2015/0166615 | A1 | 6/2015 | Xia | |
| 2015/0322122 | A1 | 11/2015 | Fraser | |
| 2016/0345555 | A1 | 1/2016 | Brigham | |
| 2016/0102125 | A1 | 4/2016 | Lewis | |

FOREIGN PATENT DOCUMENTS

| | | | |
|---|---|---|---|
| EP | 2520584 | A1 | 11/2012 |
| WO | 2018183946 | A1 | 10/2018 |

OTHER PUBLICATIONS

Ma et al. (2014, Scientific Reports, vol. 4:4489, pp. 1-6) (Year: 2014).*

Lu C. (2013, Lipoproteins and Cardiovascular Dis., vol. 1027, pp. 183-201). (Year: 2013).*

Zheng et al., "Expansion of CRISPR targeting sites in Bombyx mori", Insect Biochemistry and Molecular Biology, (Mar. 24, 2016), vol. 72, pp. 31-40.

Cho, S.W., et al., "Targeted genome engineering in human cells with the Cas9 RNA-guided endonuclease", Nature Biotechnology, (Mar. 2013), vol. 31, No. 3, pp. 230-232.

Dickinson, D.J., et al., "Engineering the Caenorhabditis elegans genome using Cas9-triggered homologous recombination", (Oct. 2013), vol. 10, No. 10, pp. 1028-1038.

Eisoldt, L., et al., "Decoding the secrets of spider silk", Materials Today, (Mar. 2011), vol. 14, No. 3, pp. 80-86.

Lazaris, A., et al., "Spider silk fibers spun from soluble recombinant silk produced in mammalian cells", Science, (Jan. 2002), vol. 295, pp. 472-476.

Mao, Y., et al., "Development of germ-line-specific CRISPR-Cas9 systems to improve the production of heritable gene modifications in *Arabidopsis*", Plant Biotechnology Journal, (2016), vol. 14, pp. 519-532.

Ma, S., et al., "Genome editing of BmFib-H gene provides an empty Bombyx mori silk gland for a highly efficient bioreactor", Scientific Reports, (Oct. 2014), vol. 4, 6867.

Menassa, R., et al., "Spider dragline silk proteins in transgenic tobacco leaves: accumulation and field production", Plant Biotechnology Journal, (2002), vol. 2, pp. 431-438.

Miao, Y., et al., "Expression of spider flagelliform silk protein in Bombxy mori cell likne by a novel Bac-to-Bac/BmNPV baculovirus expression system", Appl. Microbiol. Biotechnol. (2006), vol. 71, pp. 192-199.

Takasu, Y., et al., "Targeted mutagenesis in Bombyx mori using TALENS", TALENs: Methods and Protocols, Methods in Molecular Biology, vol. 1338, Ralf Kuhn et al. (eds.), pp. 127-142.

Teule, F., et al., "A protocol for the production of recombinant spider silk-like proteins for artificial fiber spinning", Nature Protocols, (2009), vol. 4, No. 3, pp. 341-355.

Wang, F., et al., "An optimized sericin-1 expression system for mass-producing recombinant proteins in the middle silk glands of transgenic silkworms", Transgenic Res. (2013), vol. 22, pp. 925-938.

(Continued)

*Primary Examiner* — Thaian N. Ton
*Assistant Examiner* — David A Montanari

(57) ABSTRACT

Transgenic silkworms stably expressing synthetic spider silk genes or composite silkworm/spider silk genes are disclosed. The exogenous spider silk genes are stably intergrated into a defined site of the fibroin heavy chain intron or a fibroin light chain intron of silkworms. Synthetic spider silk proteins and composite spider silk-silkworm genes and proteins are provided. The expression of exogenous spider silk genes is driven by the endogenous fibroin heavy chain promoter, improving the genetic stability of transgenic silkworms. The composite silkworm/spider silk fibers exhibit exceptional mechanical performance, compared to normal silkworm silk fibers and other transgenic silkworm fibers.

20 Claims, 20 Drawing Sheets

Specification includes a Sequence Listing.

(56) References Cited

OTHER PUBLICATIONS

Wei, W., et al., "Heritable genome editing with CRISPR/Cas9 in the silkworm, Bombyx mori", PLoS ONE, vol. 9, No. 7: e101210.
Wen, H., et al., "Transgenic silkworms (*Bombyx mori*) produce recombinant spider dragline silk in cocoons", Mol. Biol. Rep. (2010), vol. 37, pp. 1815-1821.
Xia, X-X, et al., "Native-sized recombinant spider silk protein produced in metabolically engineering *Escherichia coli* results in a strong fiber", PNAS, (Aug. 2010), vol. 107, No. 32, pp. 14059-14063.
Xu, D., et al., "Probing the impact of acidification on spider silk assembly kinetics", Biomacromolecules, (2015), vol. 16, pp. 2072-2079.
Xu, H., et al., "Construct synthetic gene encoding artificial spider dragline silk protein and its expression in milk of transgenic mice", Animal Biotechnology, (2007), vol. 18, pp. 1-12.
Yang, M., et al., "Obligate ligation-gated recombination (ObLiGaRe): Custom-designed nuclease-mediated targeted integration through nonhomologous end joining", Genome Research (2013), vol. 23, pp. 539-546.

* cited by examiner

TRANSGENIC SILKWORMS EXPRESSING SPIDER SILK

This invention was made with government support under contract number IIP1318194 awarded by the National Science Foundation and under contract number DE-EE0006857 awarded by the Department of Energy. The government has certain rights in the invention.

BACKGROUND

1. Field of the Invention

The present disclosure relates to transgenic silkworms. More specifically, the disclosure relates to transgenic silkworms that express synthetic spider silk proteins and composite spider silk-silkworm proteins. Also disclosed are the synthetic spider silk proteins, composite spider silk-silkworm proteins, and the nucleic acid sequences used to express them. Also disclosed are methods for producing such silkworms, including methods utilizing an optimized CRISPR/Cas9 system.

2. Description of the Related Art

Spider silks have a unique combination of strength and extensibility, which makes them among the toughest materials known. Unfortunately, spiders cannot be farmed on a large-scale to meet the demand of commercial applications because of their territorial and cannibalistic behaviors.

Cloning of the cDNA and gene sequences of several spider silk proteins has facilitated the design of synthetic spider silk genes. Dragline silk is composed of two proteins, Major ampullate silk proteins 1 and 2 (MaSp1 and MaSp2). The primary structure of spider silk proteins includes a large central core of repeated modular units—accounting for approximately 90% of a silk protein—flanked by non-repetitive N- and C-terminal domains. The repeated modular unit has a subset of the sequence motifs poly-alanine $(AAAA)_n$ and Glycine-Glycine-X, with X representing a variable amino acid in the major ampullate spider silk protein MaSp1 and the minor ampullate spider silk protein MiSp1 (Eisolt et al. 2011). The sequential order and the number of motifs are different in different spider silk proteins. These characteristics are responsible for the secondary structures and mechanical properties of spider silks.

Synthetic spider silk genes have been introduced into various organisms to produce recombinant spider silk proteins (rSSps). A wide range of heterologous host systems have been investigated as platforms for producing rSSps, including bacteria, yeast, mammalian cell lines, transgenic plants, mammalian animals, and insects (Lazaris et al. 2002; Menassa et al. 2004; Xu et al. 2007; Miao et al. 2006). Although the rSSps produced in these host systems have been artificially spun into fibers, the fibers are not as strong as natural spider silks, due to limitations on protein size and spinning technologies (Teulé et al. 2009).

The majority of rSSps produced to date in a series of hosts are about 30-110 kDa, much smaller than the most commonly-characterized spidroin (250-350 kDa) of spider silk fibers (Eisoldt et al. 2011). A nearly native-sized rSSps has been expressed in *Escherichia coli*, but the limitations of expression levels make it impossible to meet large scale demands (Xia et al. 2010). Additionally, techniques used for artificial spinning of rSSps are dramatically different from the natural spinning process of spiders. One of the most common methods for spinning spider silk fibers in the laboratory employs 1,1,1,3,3,3-hexafluoro-2-propanol (HFIP) which is toxic and expensive. Fibers are created by extruding the dope solution into a coagulant and then stretching in various alcohols. Spiders and silkworms, on the other hand, solvate silk proteins in water and then pull fibers from the spinneret without a requirement for coagulants, the fiber forming within nano-seconds.

In recent years, the silkworm *Bombyx mori* has been used as a platform for producing recombinant spider silk and composite silkworm/spider silk fibers (Wen 2010). *B. mori* has a similar natural fiber spinning process to that of spiders, is a prolific silk producer, and can be farmed commercially.

In the silk gland, micellar-like structures are formed because of the aggregation of the silk proteins under a remarkably high concentration, and then β-sheet crystals are formed due to shear forces imposed as the protein liquid flows along the duct. The protein structure in the fiber occurs as the fiber is pulled out of the spigot of the spider or the mouth of the silkworm, further increasing the shear stress. Additionally, the silkworm fibroin heavy chain, enriched in poly GX and comprising 70% of the silkworm fiber, has similar β-sheet structures to spider dragline silk. These biological similarities make silkworms a potential host to produce "synthetic" spider silk-like fibers.

The most frequent way to engineer transgenic silkworms uses the transposon-based piggyBac system, in which the foreign gene of interest is expressed under an exogenous promoter. Previous studies have shown that piggyBac vector-based transgenic silkworms can produce recombinant spider silk proteins by encoding the spider *Nephila clavipes* dragline silk protein MaSp1 under the control of a sericin promoter (Ser1) or a fibroin heavy chain (FibH) promoter (Teulé et al. 2009; Wen 2010). The Ser1 promoter can only drive recombinant spider silk proteins expressed in the sericin layer, however. The sericin layer is soluble and is normally degummed in sericulture; thus, the incorporation of spider silk protein in the sericin layer is unlikely to improve the mechanical properties of transgenic fibers.

The transposon-based piggyBac system has also been used to incorporate an exogenous FibH enhancer and promoter in a gene-expressing cassette driving rSSp expression in the fibroin portion of the spider silk fibers, but the piggyBac system still has several drawbacks for stable expression (Teulé et al. 2009). For example, transposons usually transfer from one genomic location to another by a cut-and-paste mechanism at TTAA chromosomal sites in the transposon-based piggyBac system. Elements with low-transposition rate may be frequently lost through genetic drift, while elements with high-transposition rate may amplify uncontrollably, leading to host sterility or other complications (Xu et al. 2015). Additionally, differences in composite silkworm/spider silk protein ratios and/or the localization of these proteins along the fiber caused by transposon-based heterogeneity may result in wide variation in the mechanical properties of the composite silk fibers (Wen et al. 2010). The homogeneity of the silks' mechanical properties serves as an important index to evaluate silk fibers. Furthermore, transposon-based gene vectors have been incapable of producing high levels of synthetic spider silk proteins in a host due to problems associated with random integrations (Teulé et al. 2009).

Thus, it has been difficult to obtain trangenic silkworms stably expressing transgenic spider silk with mechanical properties comparable or better than natural spider silk.

BRIEF SUMMARY

In one aspect, transgenic silkworms are disclosed. In some embodiments, transgenic silkworms stably express synthetic spider silk genes. In some embodiments, transgenic silkworms stably express composite spider silk-silkworm genes.

In one aspect, synthetic spider silk proteins and composite spider silk-silkworm silk proteins are disclosed.

In one aspect, the nucleic acid sequences used to express synthetic spider silk proteins and composite spider silk-silkworm silk proteins are disclosed.

In embodiments, the transgenic spider silk gene is the major ampullate spider silk gene MaSp1 or the minor ampullate spider silk gene MiSp1 of *N. Clavipes*. In embodiments, the synthetic spider silk proteins, composite spider silk-silkworm silk proteins, synthetic spider silk, and/or composite spider silk-silkworm silk has mechanical properties comparable to or superior to natural spider silk proteins and/or natural spider silk.

In one aspect, methods of producing transgenic silkworms are disclosed. In some embodiments, the methods utilize an optimized CRISPR/Cas9 system. In certain embodiments, the CRISPR/Cas9 system employs non-homologous recombination.

In some embodiments, the exogenous spider silk genetic material is introduced into the intron of the silkworm fibroin heavy chain or an intron of the fibroin light chain gene. In some embodiments, the exogenous spider silk genes or composite genes are operably linked to an endogenous silkworm promoter.

The foregoing broadly outlines the features and technical advantages of the present disclosure in order that the detailed description that follows may be better understood. Additional features and advantages of the disclosure will be described hereinafter that form the subject of the claims of this application. It will be appreciated by those of skill in the art that the conception and specific aspects disclosed herein may be readily utilized as a basis for modifying or designing other aspects for carrying out the same purposes of the present disclosure within the spirit and scope of the disclosure and provided in the appended claims.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

A detailed description of the invention is hereafter provided with specific reference being made to the drawings in which.

DETAILED DESCRIPTION

Figure 1:
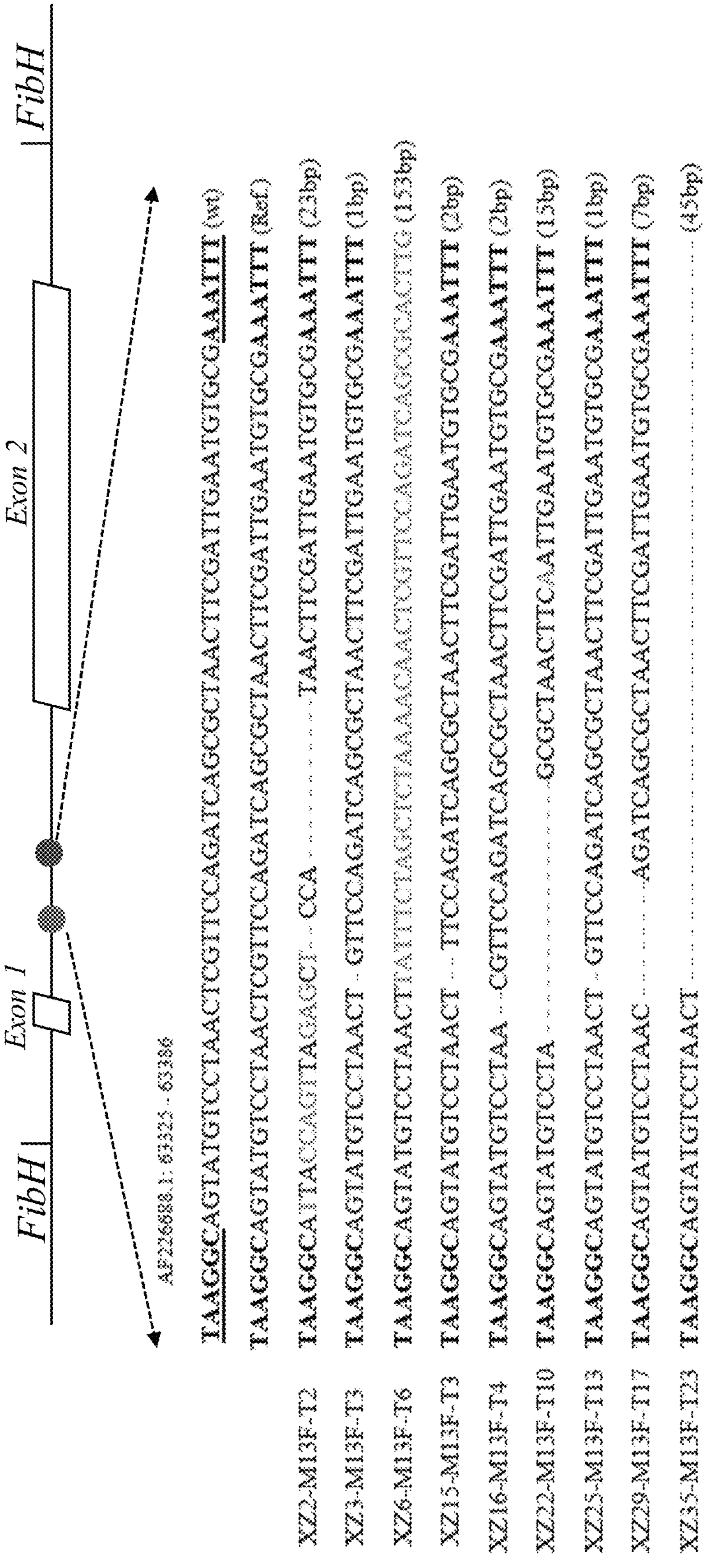
FIG. 1 illustrates CRISPR/Cas9 system HC3-mediated targeted integration in BmN cells, with wt.: wild-type gene sequence [SEQ ID NO:1]; Ref: reference sequence, the same as wt.; Testing Samples: XZ2-M13F-T2 [SEQ ID NO:2], XZ3-M13F-T3 [SEQ ID NO:3], XZ6-M13-T6 [SEQ ID NO:4], XZ15-M13F-T3 [SEQ ID NO:5], XZ16-M13F-T4 [SEQ ID NO:6], XZ22-M13-T10 [SEQ ID NO:7], XZ25-M13-T13 [SEQ ID NO:8], XZ29-M13F-T17 [SEQ ID NO:9], and XZ35-M13F-T23 [SEQ ID NO:10]; gene replacements are shown in red and dashes indicate deletions. The nucleotides in bold indicate the N-terminal and C-terminal of the gene sequences.

Various aspects are described below with reference to the drawings. The relationship and functioning of the various elements of the aspects may better be understood by reference to the following detailed description. However, aspects are not limited to those illustrated in the drawings or explicitly described below. It should be understood that the drawings are not necessarily to scale, and in certain instances details may have been omitted that are not necessary for an understanding of aspects disclosed herein, such as conventional fabrication and assembly. Headings are provided for the convenience of the reader and to assist organization of the disclosure and should not be construed to limit or otherwise define the scope of the invention.

In one aspect, the disclosure provides transgenic silkworms stably expressing synthetic spider silk genes or composite spider silk-silkworm genes.

As used herein, the term "synthetic" is understood to include a gene sequence or resulting gene expression product (e.g., protein) that encompasses some or all of the native gene sequence or gene expression product, but is removed or otherwise isolated from its native host. As such, a "synthetic spider silk gene" is understood to include a DNA sequence that has at least 70%, at least 75%, at least 80%, at least 85%, at least 90%, at least 95%, at least 96%, at least 97%, at least 98%, at least 99%, or 100% sequence identity with the native spider silk gene over at least a 20 base pair (bp) contiguous segment of the gene or that produces a gene expression product having at least at least 70%, at least 75%, at least 80%, at least 85%, at least 90%, at least 95%, at least 96%, at least 97%, at least 98%, at least 99%, or 100% protein sequence identity with the native spider silk protein over at least a 20 amino acid contiguous segment of the protein. The term "synthetic" may be used herein interchangeably with the terms "exogenous" or "transgenic," particularly when describing a synthetic gene sequence that is derived from an organism different from its current host.

Similarly, the term "synthetic spider silk gene" is understood to include a DNA sequence that may be less than the full length of the native spider silk gene.

In some embodiments, transgenically-produced spider silk or composite spider silk-silkworm silk reflects about 10-15% of the total silk production by the silkworm. In other embodiments, transgenically-produced spider silk or composite spider silk-silkworm silk reflects over 15%, over 20%, over 25%, over 30%, over 35%, over 40%, over 45%, over 50%, over 55%, over 60%, over 65%, over 70%, over 75%, over 80%, over 85%, over 90%, over 95%, over 99%, or about 100% of the total silk production by the silkworm.

In this respect, the engineered spider silk may substantially replace endogenous production of one or more of the silkworm's own silk-associated proteins, such as the silkworm fibroin protein.

It is understood that the protein fibroin, including the fibroin heavy chain and fibroin light chain, is the core protein component of silk in spiders and silkworms. Thus, the terms "fibroin," "silk protein," or "spider silk protein" may in some cases be used interchangeably herein with reference to "silk" or "spider silk," as appropriate.

The limitations of prior technology have made it difficult to produce transgenic silkworms that stably integrate a transgene larger than about 3 kb in length in silkworms. In a specific embodiment, a transgenic silkworm is disclosed, the transgenic silkworm having a stably-integrated synthetic spider silk gene greater than about three kilobases (3 kb) in length. In certain embodiments, the stably-integrated synthetic spider silk gene is greater than about 4 kb in length; greater than about 5 kb in length; greater than about 6 kb in length; greater than about 7 kb in length; greater than about 8 kb in length; greater than about 9 kb in length; or greater than about 10 kb in length. In some embodiments, the synthetic silk gene is about 10 kb in length.

As used herein, the term "stably integrated" means that the introduced transgenic material is capable of successfully passing through cell division to daughter cells and/or offspring, for example, into the second generation, third generation, etc., without substantial change in sequence or the transgenic material being lost. Thus, in some embodiments, a stably integrated transgene is present in the first generation, second generation, third generation, etc. of a transgenic silkworm (i.e., in progeny). In certain embodiments, the stably integrated transgene is expressed in the first generation, second generation, third generation, etc. of a transgenic silkworm (i.e., in progeny).

It is also understood that stable integration of an exogenous nucleotide sequence into a host gene, such as through a CRISPR/Cas9 mediated knock-in system, may produce a composite (i.e., hybrid) gene including both exogenous and endogenous nucleic material. Thus, in some embodiments, a transgenic silkworm is disclosed, the transgenic silkworm having a composite spider silk-silkworm gene.

It is further understood that expression of such a composite gene sequence may produce a composite (i.e., hybrid or fusion) protein or proteins. Thus, in some embodiments, a transgenic silkworm is disclosed that stably expresses a synthetic spider silk gene or a composite/hybrid spider silk-silkworm gene.

In embodiments, integrated genes are expressed under control (i.e., operably linked) of an endogenous promoter in the silkworms. In some embodiments, a spider silk gene is operably linked to an endogenous promoter. For example, exogenous spider silk genetic material may be introduced into the single intron of the silkworm fibroin heavy chain gene, FibH, with stable expression of the integrated transgene driven by an endogenous promoter. In another example, exogenous spider silk genetic material may be introduced into any of the six introns of the silkworm fibroin light chain gene, FibL, with stable expression of the integrated transgene driven by an endogenous promoter. Expression of MaSp1 or MiSp1 in silkworm, driven by an endogenous fibroin promoter, appears to improve genetic stability in transgenic silkworms. In specific embodiments, the endogenous silkworm promoter is the silkworm-specific U6 promoter. The disclosed strategies thus overcome the limitations of CRISPR/Cas9 using homologous recombination, random integrations presented by the transposon-based piggyBac system, and other systems.

In some embodiments, the exogenous spider silk gene may comprise the major ampullate spider silk gene MaSp1 gene, major ampullate spider silk gene MaSp2, Aciniform gene Ac1, Flagelliform gene Flag, Piriform gene *Piri*, or minor ampullate gene MiSp1, or synthetic variants thereof. See Teule 2007.

Thus, in a specific embodiment, a transgenic silkworm is disclosed, the transgenic silkworm having a stably-integrated synthetic spider silk gene operably linked to an endogenous silkworm promoter, where the exogenous spider silk gene is greater than about three kilobases (3 kb) in length.

In one aspect, transgenic spider silk proteins, composite spider silk-silkworm proteins, transgenic spider silk, composite spider silk-silkworm silk, and the nucleic acid sequences used to express them are disclosed.

The sequential order and number of protein motifs are different in different spider silk proteins. These characteristics are responsible for the secondary structures and mechanical properties of spider silks. Accordingly, in various embodiments, different synthetic spider silk genes have been designed to integrate these motifs with various mechanical properties.

In some embodiments, the introduced spider silk gene is the major ampullate spider silk gene MaSp1 (~10 kb) or minor ampullate spider silk gene MiSp1 (~10 kb) of *N. Clavipes*. In embodiments, transgenic silkworms express composite silkworm/spider silk proteins.

The disclosed hybrid proteins may be larger and more stable than previous transgenic silk proteins. In embodiments, the transgenic spider silk proteins, composite spider silk-silkworm silk proteins, and/or composite spider silk-silkworm silk have mechanical properties comparable to or superior to natural spider silk proteins and/or natural spider silk, as well as other transgenic silkworm fibers described in the literature.

In certain embodiments, these improved properties are present in the $G_0$ and the $G_1$ generation of transgenic silkworms. In certain embodiments, these improved properties are present in successive generations of transgenic silkworms.

In one aspect, methods are disclosed for producing transgenic silkworms.

Current genome editing technologies facilitate introducing site-specific modifications in the genomes of cells and organisms and provide a means to deliver exogenous genes at precise target sites in silkworms. Preliminary applications of the latest genomic editing technologies such as zinc-finger nucleases (ZFN), transcription activator-like effector nucleases (TALENs), and the clustered regularly interspaced short palindromic repeat (CRISPR) system in silkworms have mostly focused on the silkworm phenotype gene (BmBLOS2) or the non-phenotype gene (Bmku70) (Wang et al. 2013). For example, researchers disrupted the fibroin heavy chain (FibH) gene of silkworm glands using a customized ZFN (Ma et al. 2014). Applications of these genome editing techniques in silkworms are generally limited to the knock-out phase, however (Wei 2014).

Thus, in some embodiments, a synthetic spider silk gene and/or composite spider silk-silkworm silk gene is expressed in the silk gland of a silkworm. In other embodiments, a synthetic spider silk gene and/or composite spider silk-silkworm silk gene is expressed in other tissues or organs of a silkworm.

Researchers have successfully knocked-in a red fluorescence gene at a defined locus of silkworms using homologous recombination (Takasu et al. 2016). Using these techniques to stably knock-in a large (e.g., greater than 3 kb) transgene at a defined silkworm site and express the transgene under an endogenous promoter has not been demonstrated.

The CRISPR/Cas9 system has been used in different research models, including insect cells, plants and human cells (Mao et al. 2016; Cho et al. 2013). The advantages of this system are the relatively easy production and design of constructs, time-saving production of transgenic organisms, and binding stability to the genomic DNA.

CRISPR has two components: a "guide" RNA (gRNA) and a non-specific CRISPR-associated endonuclease (Cas9). CRISPR creates DNA double strand breaks (DSBs) at a defined position in a chromosome. The Cas9-mediated DSBs can be spontaneously repaired via the independent pathway of homology-directed repair (HDR) or nonhomologous end-joining (NHEJ).

The homologous recombination-mediated knock-in system has been the preferred technology to introduce foreign genes into desired hosts. For example, using the CRISPR/Cas9 system, an exogenous DNA fragment has been added through precise and controlled homologous recombination (HR) repair systems in *Caenorhabditis elegans* (Dickinson et al. 2013). One limitation of this approach is that it is difficult to incorporate large DNA fragments into the target organism.

Nonhomologous end-joining (NHEJ), which acts independently of the HR pathway(s), is highly efficient. For example, a 15 kb inducible gene expression cassette has been introduced at a defined locus in human cell lines using NHEJ (Yang et al. 2013). But NHEJ is associated with potentially damaging nucleotide insertions and deletions (indels) and/or substitutions in the DSB region, which can reduce transgene stability and expression.

Thus, in some embodiments, the CRISPR/Cas9 system employs non-homologous recombination (end-joining) to facilitate introduction of large exogenous nuclear material, while targeting an integration site that is not affected by adjacent mutations.

In some embodiments, an optimized CRISPR/Cas9 system is utilized to introduce relatively large spider silk genes into silkworm. This strategy overcomes the limitations of random integrations of transposon-based piggyBac system and other systems known in the art, including other applications of CRISPR itself. The disclosed methods facilitate insertion of large exogenous DNA fragments at defined sites within the silkworm genome. In some embodiments, fragments of the disclosed synthetic spider silk genes is introduced into a silkworm.

In a specific embodiment, a method is disclosed for producing a transgenic silkworm, the method comprising: introducing an exogenous synthetic spider silk gene operably linked to an endogenous silkworm promoter, wherein the exogenous spider silk gene is greater than about three kilobases (3 kb) in length.

In a specific embodiment, a method is disclosed for producing a transgenic silkworm, the method comprising: introducing an isolated nucleic acid having SEQ ID NO. 25 or SEQ ID NO:26, or a fragment of either thereof, into a defined site of the silkworm genome using a CRISPR/Cas9 system, such that the isolated nucleic acid is operably linked to an endogenous silkworm promoter, wherein the exogenous nucleic acid is stably integrated into the silkworm genome.

In certain embodiments, the disclosed methods do not require use of exogenous promoters in the HC-NHEJ donors.

For example, using the methods disclosed herein, two large spider silk genes may be successfully integrated at the defined locus of the fibroin heavy chain gene using optimized CRISPR/Cas9 initiated non-homologous end joining. The incorporated spider silk genes may be fully expressed under the endogenous FibH promoter of silkworm.

An optimized CRISPR/Cas9 system, as used herein, may be specifically designed for efficient and stable integration and expression of a transgenic sequence in silkworm. In some embodiments, the CRISPR/Cas9 system is optimized for silkworms using the silkworm-specific U6 promoter. The CRISPR/Cas9 system may be further optimized by targeting silkworm genomic sequences (e.g., introns) that are not disrupted by introduction of exogenous nucleic acid material.

In certain embodiments, relatively large synthetic spider silk protein genes (e.g., MaSp1 and MiSp1) are thus successfully integrated into the intron of the FibH gene and/or into an intron of the FibL gene. These genes are each approximately 9-10 kb, larger than any comparable successful gene knock-in previously reported in silkworms.

The disclosed methods provide efficient methods for creating transgenic silkworms transformed with a synthetic spider gene, which are superior to the transposon-based piggyBac system. The disclosed methods make possible, for example, expression of a large exogenous synthetic spider gene (~10 kb) driven by an endogenous FibH promoter through nonhomologous end-joining (NHEJ). The mechanical properties of the composite silkworm/spider fibers in these transgenic silkworms are also significantly improved, compared to non-transgenic fibers. The genetic stability of these transgenes and the superior mechanical characteristics of the expression products persists in transgenic offspring. The strategy developed in this study may be extended to other exogenous synthetic silk proteins for commercial production of biomolecules by using silkworm as an expression system.

The following examples are provided to illustrate certain features and/or aspects of the disclosure. The examples should not be construed to limit the disclosure to the particular features or aspects described therein.

EXAMPLES

Example 1. Spider Silk Transgenes in FibH Intron

Using the silkworm-specific CRIPSR/Cas9 system, two relatively large synthetic spider silk genes, the major ampullate spider silk gene (MaSp1, ~10 kb) and the minor ampullate spider silk gene (MiSp1, ~10 kb) of *N. Clavipes* were separately introduced into the only intron of the silkworm FibH gene. An optimized silkworm-specific CRISPR/Cas9 system was used with NHEJ. Expression was driven by the endogenous FibH promoter in the transgenic silkworm glands to improve yields and ensure genetic stability.

Construction of Cas9 and sU6 gRNA Expression Vectors for Silkworm.

To ensure the CRISPR/Cas9 system was well expressed in BmN cells and/or silkworms, the coding region of cas9 was constructed into a pIE-1 vector under the hr5 enhancer and IE1 promoter.

To construct the expression vector of Cas9 in silkworms, the coding region of Cas9 was excised from Px330-U6-Chimeric BB-CBh-hSpCas9 (Addgene plasmid #42230) with AgeI and NotI (NEB, R3552S and R3189S), gel-purified (Qiagen, No. 28704), recovered and sub-cloned into the corresponding sites downstream of the hr5 enhancer and IE1 promoter in pIEx™-1 (Novagen, No. 71241-3) to form pIEx™-1-Cas9. To facilitate the tracking of Cas9 expression and presence inside cells, eGFP was added on the C-terminal of Cas9 to form the plasmid pIEx™-1-eGFP-Cas9. To construct the sgRNA-expressing vector for silkworms, an 467 bp gBlock DNA fragment including the silkworm-specific U6 promoter and terminator as well as part of essential sgRNA frame was synthesized by Integrated DNA Technologies (Coralville, Iowa) [SEQ ID NO:22]. This gBlock DNA fragment was PCR-amplified (primer 1: AGGTTATGTAGTACACATTG [SEQ ID NO: 14] and primer 2: TTAATGCCAACTTTGTACA [SEQ ID NO: 15]) and then sub-cloned into the pGEM®-T easy vector system (Promega, A3600) to form pGEM®-T-sU6 (silkwormU6). Oligo gRNAs (gRNA_sU6_FibH_1, 2, 3) having 20 nucleotides, the target site sequence which starts with G in the sgRNA-1 and ends with C in the sgRNA2 were made. See Table 1, below, which shows the gRNAs Design of the CRISPR/Cas9 system. Sequences listed in Table 1 are SEQ ID NOS: 16-21, as listed from first to last in the table.

TABLE 1

| Name | Sequence (5'-3') | Genome Location |
|---|---|---|
| gRNA_sU6_FibH_1_F | TTTTTTTAGGTATATATACAAAATATCGTGCTCTACAAGT GGTTTTCCCTACCTATTAGC | AF226688.1:63141-63159 |
| gRNA_sU6_FibH_1_R | TATTAATGCCAACTTTGTACAAGAAAGCTGGGTCTAGAA AAAAAGCACCGACTCGGTGCCACTTTTTCAAGTTGATA ACGGACTAGCCTTATTTTAACTTGCTATTTCTAGCTCTAA AACGCTAATAGGTAGGGAAAACC | AF226688.1:63141-63159 |
| gRNA_sU6_FibH_2_F | TTTTTTTAGGTATATATACAAAATATCGTGCTCTACAAGT GATGTGACCATAAAATCTCG | AF226688.1:63194-63212 |
| gRNA_sU6_FibH_2_R | TATTAATGCCAACTTTGTACAAGAAAGCTGGGTCTAGAA AAAAAGCACCGACTCGGTGCCACTTTTTCAAGTTGATA ACGGACTAGCCTTATTTTAACTTGCTATTTCTAGCTCTAA AACCGAGATTTTATGGTCACATC | AF226688.1:63194-63212 |
| gRNA_sU6_FibH_3_F | TTTTTTTAGGTATATATACAAAATATCGTGCTCTACAAGT GCGCTGATCTGGAACGAGTT | AF226688.1:63341-63360 |
| gRNA_sU6_FibH_3_R | TATTAATGCCAACTTTGTACAAGAAAGCTGGGTCTAGAA AAAAAGCACCGACTCGGTGCCACTTTTTCAAGTTGATA ACGGACTAGCCTTATTTTAACTTGCTATTTCTAGCTCTAA AACAACTCGTTCCAGATCAGCGC | AF226688.1:63341-63360 |

The oligos, including sgRNA targeting sites and part of sgRNA frame, were also ordered from Integrated DNA Technologies and were annealed and extended to form double strand DNAs. These double strand DNAs were gel-purified (Qiagen, No. 28704) and sub-cloned into the MfeI-digested pGEM®-T-sU6 using Gibson Assembly® Master Mix (NEB, E2611S) to form final sgRNA expression vector pGEM®-T-sU6-sgRNA. A codon-optimized U6 promoter (sU6) (SEQ ID NO:71) was used to construct silkworm-specific gRNA (sgRNA) expression vectors.

As noted, NHEJ repair systems are associated with random nucleotide insertions and/or deletions, leading to potential loss of function of a protein if it occurs in the exons of a gene. Three different sgRNAs were designed to target the only intron of the silkworm fibroin heavy chain (FibH) to eliminate negative effects due to error-prone splicing and/or modifications via NHEJ repair. The three gRNAs (gRNA_sU6_FibH_1, 2, 3) that specifically target the intron of heavy chain AF226688.1: 63138-63159; 63196-63215; 63318-63337 were tested. See Table 1.

CRISPR/Cas9 Evaluation in BmN Cells.

The fully constructed plasmids pIEx™-1-eGFP-Cas9 and pGEM®-T-sU6-sgRNA were transfected to BmN cells using X-tremeGENE™ HP DNA Transfection Reagent (Roche, No. 06 366 244 001) with a ratio of 1 μg total plasmids to 2 μl transfection reagent for each well. The control group was transfected with the same volume of $ddH_2O$ in which the plasmids were suspended without the DNA plasmids. After 72-96 h transfections, the cells were washed with 1×PBS buffer (pH 7.4), the genomic DNA of transfected BmN cells were harvested by using QuickExtract™ DNA Extraction Solution (Epicentre, QE09050) and then subjected to PCR amplification by Taq PCR Master Mix Kit (Qiagen, No. 201443) using the following primers: HC-lacZdisr-Forward: ATATCTAGATTCTCAGTGGGTCGCGTTAC [SEQ ID NO:23], and HC-lacZdisr-Reverse: ATAGGTACCTCGATAACTGCCCCAGATGC [SEQ ID NO:24]. The PCR products (~250 bp) were cloned into the pGEM®-T easy vector system (Promega, A3600). After transformation into high efficiency 5-alpha competent *E. coli* (NEB, C2987P) colonies were sequenced. Colonies determined to contain the mutation were determined by comparing the sequences of the PCR products to the reference sequence of the fibroin heavy chain gene (AF226688.1:63001-63601). The CRISPR/Cas9 efficiencies were evaluated based on the ratio of the mutated sequences to the unmutated sequences.

The introduction of indels in the FibH intron does not affect the subsequent transcription and protein expression of FibH genes. The transgenic silkworms were thus created by optimized silkworm-specific CRISPR/Cas9 system triggered NHEJ. This strategy was also expected to have no effect on subsequent alternative splicing and/or nucleotide modifications, even allowing for NHEJ repair mutations (30). Three different gRNAs of the CRISPR/Cas9 system, with three different target sites (HC-1, -2, -3), were transformed separately into BmN cells to evaluate their on-target efficiencies.

Genomic DNA was extracted and NHEJ repair regions were PCR amplified. HC-3 gRNA was introduced into silkworm eggs to generate transformed embryos because it had the highest repair rate (30% determined by sequencing) at a defined site in FibH genome.

FIG. 1 shows CRISPR/Cas9 system HC3-mediated targeted integration in BmN cells, with wt.: wild-type gene sequence [SEQ ID NO:1] from the intron of the fibroin heavy chain gene, FibH; Ref: reference sequence, the same as wt.; Testing Samples: XZ2-M13F-T2 [SEQ ID NO:2], XZ3-M13F-T3 [SEQ ID NO:3], XZ6-M13-T6 [SEQ ID NO:4], XZ15-M13F-T3 [SEQ ID NO:5], XZ16-M13F-T4 [SEQ ID NO:6], XZ22-M13-T10 [SEQ ID NO:7], XZ25-M13-T13 [SEQ ID NO:8], XZ29-M13F-T17 [SEQ ID NO:9], and XZ35-M13F-T23 [SEQ ID NO:10]. Gene replacements shown in red, dashes indicate deletions.

HC-NHEJ Donor Design.

In previous research, the transposon-based piggyBac system was used to incorporate the fibroin heavy chain (FibH) promoter to drive temporary expression of the foreign spider silk protein gene in the posterior silk glands of transgenic silkworms. Here, a donor vector pBluescript II SK (+), was used as a backbone to construct HC-NHEJ vectors with synthetic spider silk expression motif's MaSp1-8 repeats (~10 kb) or MiSp1-8 repeats (~10 kb) with protein molecular weights of 214 kDa and 229 kDa, respectively.

The major ampullate spider silk protein MaSp1 gene is enriched with [GGX]n and poly (A) motifs. The minor ampullate spider silk protein MiSp1 gene is enriched with the GGXGGY (X=Q or A) motifs alternating with (GA)y (A)z motifs (y=3-6 and z=2-5). Accordingly, the synthesized spider silk protein DNA of [MaSp1]8 and [MiSp1]8 synthesized by Life Technologies and connected with 8 repeats using the enzymes AgeI and BspEI (NEB, R3552S and R0540S). Table 2 below shows the DNA sequence of the MaSp1 [SEQ ID NO: 25, top] and MiSp1 [SEQ ID NO. 26, bottom] synthetic spider silk genes.

TABLE 2

| Name | Sequence (5'-3') |
|---|---|
| MaSp1(8) | (GGTGGTGCAGGTCAGGGTGGTTATGGTGGTCTGGGTAGCCAGGGTGCCGGTCGTGGTGGACTGGGTGGTCAAGGT<br>GCTGGTGCAGCAGCAGCTGCCGCAGCAGCAGGCGGTGCAGGCCAAGGCGGATATGGCGGACTGGGTTCACAGGG<br>TGCAGGCCGTGGCGGTTTAGGTGGTCAAGGCGCAGGCGCTGCTGCAGCCGCAGCGGCAGCAGCTGGCCAAGGTGG<br>CTATGGTGGCTTAGGCTCACAGGGTGGCGGTGCTGGACAGGGTGGATACGGTGGCCTTGGCAGTCAAGGTGCGGG<br>TCGCGGTGGTTTAGGCGGTCAGGGTGCGGGTGCGGCTGCTGCAGCTGCGGCAGCGGGTGGTGCTGGGCAAGGCGG<br>TTACGGTGGATTAGGTAGCCAAGGTGCAGGACGCGGAGGTCTTGGTGGACAGGGTGCTGGCGCTGCTGCGGCAGC<br>AGCAGCCGCTGGGGGTGCTGGTCAAGGGGGTTATGGCGGTTTAGGATCTCAGGGTGCGGGACGGGGTGGTCTGGG<br>AGGGCAAGGGGCAGGCGCAGCAGCAGCGGCAGCTGCAGCCGGTGGTGCCGGACAAGGGGGATATGGGGGTCTTG<br>GCTCCCAAGGCGCTGGTCGTGGCGGTCTTGGAGGCCAAGGTGCCGGTGCCGCTGCAGCGGCTGCTGCTGCAGCGG<br>GTCAAGGGGGATACGGTGGTCTGGGATCACAAGGTGGTGGCGCAGGGCAAGGTGGGTATGGGGGTTTAGGTTCGC<br>AAGGTGCTGGCCGTGGGGGACTGGGAGGACAGGGTGCCGGTGCGGCAGCCGCTGCAGCTGCTGCGGGTGGCGCT<br>GGTCAGGGTGGCTATGGCGGATTGGGCTCTCAAGGGGCAGGTCGGGGTGGCTTGGGAGGACAAGGTGCGGGTGCA<br>GCCGCTGCGGCAGCTGCCGCTGGCGGAGCAGGCCAGGGTGGCTACGGTGGACTGGGTTCCCAAGGTGCGGGAAG<br>AGGTGGCTTGGGTGGCCAGGGTGCAGGGGCAGCGGCTGCAGCGGCAGCAGCC)8 |
| MiSp1(8) | (GGTGGTGCCGGTGGTTATGGTCGTGGTGCTGGTGCGGGTGCCGGTGCAGCAGCTGGTGCCGGTGCTGGCGCAGGC<br>GGTTATGGTGGTCAGGGTGGCTACGGTGCCGGTGCCGGTGCTGGTGCCGCAGCCGCAGCGGGTGCGGGTGCAGGC<br>GGTGCTGGCGGTTATGGCAGAGGTGCTGGGGCTGGTGCAGGCGCTGCAGCCGGTGCGGGTGCTGGTGCGGGTGGA |

TABLE 2-continued

| Name | Sequence (5'-3') |
|---|---|
| | TATGGTGGCCAGGGTGGTTATGGCGCTGGCGCAGGGGCAGGCGCAGCAGCAGCAGCTGGGGCAGGCGCAGGCGG<br>TGCCGGTGGCTATGGACGCGGAGCCGGTGCCGGTGCAGGGGCAGCAGCGGGTGCTGGTGCCGGTGCAGGGGGTTA<br>TGGTGGCCAAGGCGGATATGGTGCGGGTGCAGGCGCTGGTGCAGCAGCAGCCGCTGGTGCCGGTGCCGGTGGTGC<br>GGGTGGCTACGGAAGAGGTGCGGGTGCCGGTGCCGGTGCTGCAGCGGGTGCGGGTGCGGGTGCCGGTGGTTATGG<br>CGGTCAGGGTGGGTATGGTGCGGGTGCTGGTGCAGGCGCAGCTGCAGCCGCTGGTGCTGGTGCAGGCGGAGCCGG<br>TGGATATGGCCGAGGTGCTGGCGCAGGCGCTGGCGCTGCTGCTGGTGCCGGTGCGGGTGCTGGGGATACGGTGG<br>TCAAGGGGGTTATGGTGCGGGTGCCGGTGCGGGTGCAGCCGCAGCAGCTGGTGCGGGTGCGGGTGGTGCAGGGGG<br>ATATGGCCGTGGTGCCGGTGCTGGTGCGGGTGCTGCAGCCGGTGCTGGGGCAGGGGCTGGCGGTTATGGGGGTCA<br>AGGCGGTTATGGCGCTGGTGCTGGTGCTGGGGCTGCCGCAGCAGCCGGTGCTGGTGCTGGCGGTGCGGGTGGTTA<br>CGGTCGGGGAGCTGGCGCTGGTGCTGGCGCAGCAGCGGGTGCCGGTGCTGGTGCCGGTGGCTACGGTGGACAAGG<br>TGGCTATGGTGCCGGTGCAGGCGCAGGGGCTGCAGCCGCAGCCGGTGCCGGTGCCGGTGGCGCTGGGGGTTATGG<br>TCGCGGAGCGGGTGCAGGCGCAGGCGCAGCCGCTGGCGCTGGTGCGGGTGCTGGCGGTTATGGTGGACAAGGGG<br>GTTATGGGGCTGGTGCTGGCGCAGGGGCAGCTGCTGCAGCGGGTGCTGGCGCT)8 |

Figure 2:
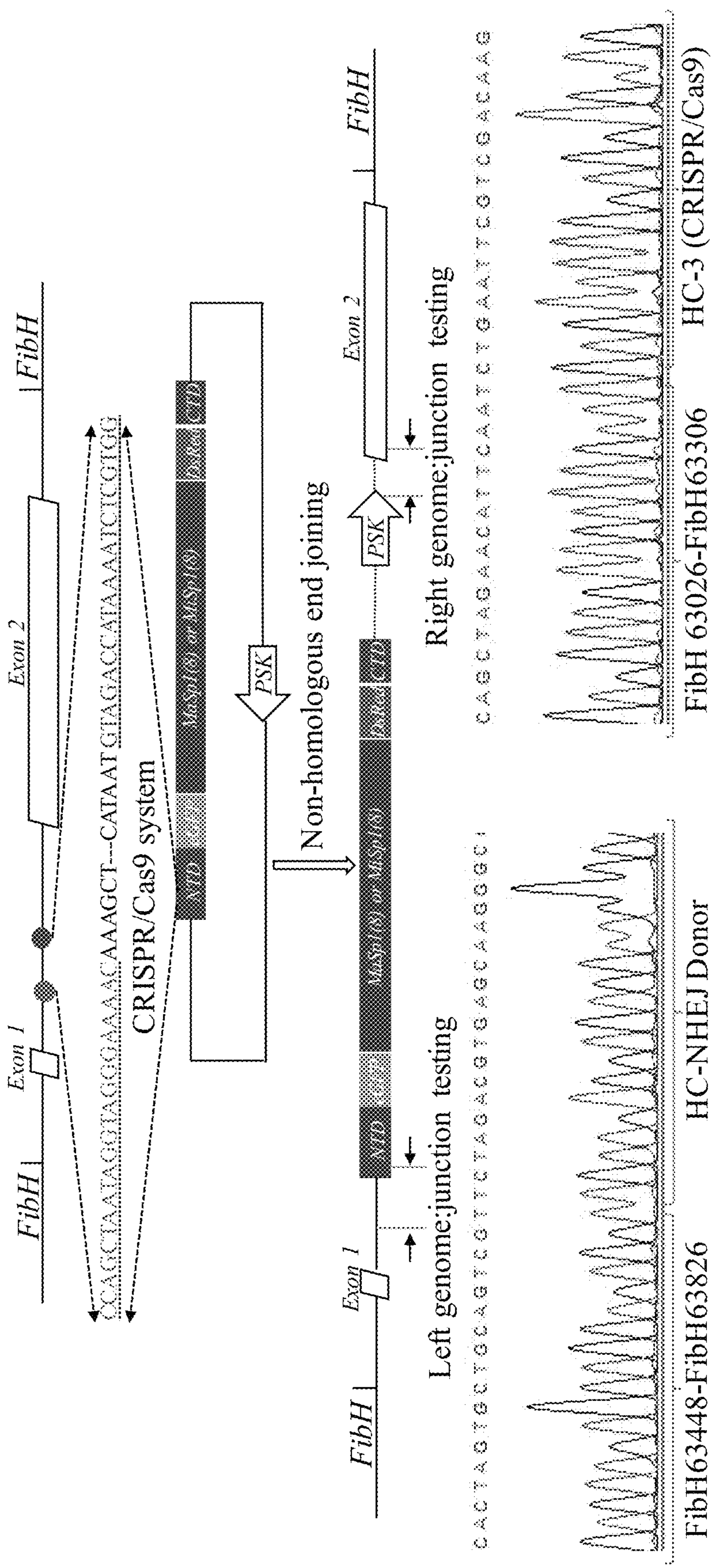
FIG. 2 is a schematic illustration of a HC-NHEJ strategy. Red-Green dots: indicate silkworm gRNA recognition sites (HC-1, -2, -3) with the corresponding sequences displayed in the scheme (AF226688.1: 63183-63215). The underlined sequences in red and green show the target sites of gRNA HC-1 and HC-3 [SEQ ID NO:11 in red/left side; SEQ ID NO:12 in green/right side]. The entire listed sequence is SEQ ID NO:13.

The entire encoding fragment was cloned into a pBluescript II SK (+) vector with HindIII and BamHI (NEB, R3104S and R3136S) to produce pSK-MaSp1/MiSp (8). The 3' coding sequence and poly (A) signal (CTD) of the silkworm heavy chain genome was inserted into pSK-MaSp1/MiSp (8) with SacII and SacI (NEB, R0157S and R3156S) to produce pSK-MaSp1/MiSp1 (8)-CTD. The DsRed gene fragment was amplified from piggyBac1379 by PCR with gene-specific primers and then sub-cloned into pSK-MaSp1/MiSp1(8)-CTD to produce pSK-MaSp1/MiSp1(8)-DsRed-CTD. The 5' key regulatory elements and protein sequences included the N-terminal domain (intron1/exon2) and eGFP. This was produced by PCR with the piggyBac1379 plasmid DNA and was cloned into pSK-MaSp1/MiSp1(8)-DsRed-CTD to produce the full pSK-NTD-MaSp1/MiSp1(8)-DsRed-CTD vector. PCR primers for the constructions of pSK-NTD-MaSp1/MiSp1(8)-DsRed-CTD vector are shown in Table 3, below (SEQ ID NOS: 27-32, as listed in order from first to last in the table).

relied only on the endogenous FibH promoter in the posterior silk gland cells, which means that the expression of fhc proteins should be directly replaced by expression of synthetic spider silk proteins. See FIG. 2, which illustrates the HC-NHEJ strategy. Insertion of the HC-NHEJ donor causes a size shift from about 15.7 kb (wild type FibH gene) to about 16 kb (ligation product of the who HC-NHEJ donor). The 13 kb gene cassette, including NTD with eGFP, MaSp1-8 repeats or MiSp1-8 repeats, DsRed and CTD, can be expressed under an endogenous FibH promoter.

The CTD of the gene cassette includes a stop code from the original FibH genome. Genomic insertion of HC-NHEJ donor in $G_0$ HCA transgenic silkworms, as revealed by nested PCR and sequencing. The horizontal arrow bars indicate the primers for the genome: junction testing. Left genome:junction testing sequence, as shown, is SEQ ID NO: 33; right genome:junction testing sequence is SEQ ID NO:34. Table 4 below shows additional primers used for the genome: junction testing of transgenic silkworm moths. Sequences listed in Table 4 are SEQ ID NOS: 35-42, as listed in order from first to last in the table.

TABLE 3

| Name | Sequence (5'-3') | Restriction Sites Added | Original from NCBI |
|---|---|---|---|
| NTD-F2 | ATAGGTACCAGCCCTAACAAGAGCTCACGTGATAGATTCTATGAAGC ACTTCGGTAACGCGACCCAGTGTTAGCAAATTCTTTCAGGTTG | 5' KpnI | AF226688.1:63026-63862 with eGFP |
| NTD(eGFP)-R | TAACTCGAGAGCTTGTACAGCTCGTCCATGCCGAGAG | 3' XholI | |
| DsRed-F | ATAGGATCCCGCCTCCTCCGAGAACGTCAT | 5' BamHI | |
| DsRed-R | TAATCTAGACAGGAACAGGTGGTGGCGG | 3' XbaI | |
| CTD-F | CAACCGCGGAAGCGTCAGTTACGGAGCTGGCAG | 5' SacII | AF226688.1:79021-79500 |
| CTD-R | TAAGAGCTCTATAGTATTCTTAGTTGAGAAGGCATAC | 3' SacI | |

Because exogenous promoters and enhancers were not used in HC-NHEJ vector construction (see Table 3, above), expression of synthetic spider silk protein MaSp1 or MiSp1

TABLE 4

| Primer No. | Name | Sequence (5'-3') | Primer combination for PCRs |
|---|---|---|---|
| 1 | FibH62454-F | TTGTGATCTTGTGCTGCGCT | 1 and 2 for 5'-junction first time PCR |
| 2 | H1-R | CAGGGTCAGCTTGCCGTAG | |
| 3 | FibH62737-F | CACCGGTAAATCAGCATTGC | 3 and 4 for 5'-junction secondary time PCR |
| 4 | FibH-donor-R | CGACTGCAGCACTAGTGCTG | |

TABLE 4-continued

| Primer No. | Name | Sequence (5'-3') | Primer combination for PCRs |
|---|---|---|---|
| 5 | PSK-F | GGGCGATCGGTGCGGGCCTC | 5 and 6 for 3'-junction first time PCR |
| 6 | FibH63746-R | TGAGCAACAGTACCATCGGA | |
| 7 | PSK-F2 | TACGACTCACTATAGGGCGA | 7 and 8 for 3'-junction second-ary time PCR |
| 8 | FibH63575-R | TCGATAACTGCCCCAGATGC | |

The 5' genome: junction was precisely identified (Left genome: junction testing) while at the 3' junction: genome performed non-precision end repair resulting in some sequence heterogeneity which would be of no consequence since it will be excised out (Right genome: junction). These results indicated the HC-NHEJ donor was successfully integrated at the defined locus of FibH in transgenic silkworms. A relatively large synthetic spider silk protein gene (MaSp1 or MiSp1, ~10 kb) was thus integrated into the genome of silkworm FibH at specific sites, which is not possible with the random integration of the transposon-based piggyBac system.

The original promoter of pBluescript II SK (+) vector can only be used to run plasmid amplification in *E. coli* and cannot be used for gene expression in transgenic silkworms. The MaSp1 or MiSp1 genes were flanked by 5' and 3' regulatory elements and protein sequences (hereinafter as 5' and 3' terminal). The 5' terminal region includes a portion of the intron 1/exon 2 of the FibH gene and an enhanced green fluorescence protein eGFP gene for detection. The 3' terminal region contains a portion of the 3' end and the stop codon of exon 2 of the FibH gene. A red fluorescence DsRed gene was added immediately after the MaSp1 and MiSp1 gene to track the expression of the full length synthetic spider silk gene. As long as the optimized CRISPR/Cas9 generated DSBs both at the intron of FibH and in the HC-NHEJ vector, the linearized vector could be ligated into the same DSB site of FibH through NHEJ, leading to the insertion of the entire HC-NHEJ vector. The error-prone mechanism of NHEJ repaired the DSBs of the optimized silkworm specific CRISPR/Cas9 system, therefore, the gRNAs cannot recognize their target sites in the FibH genome of transgenic silkworms. The transgenic silkworms transformed with the donor vectors containing the MaSp1 gene were designated as the HCA group, while the transgenic silkworms transformed with the donor vectors containing the MiSp1 gene as the HCl group.

Unlike the mechanism of homologous recombination where only the target exogenous gene can be bound to specific sites by homologous arms, the whole plasmid of HC-NHEJ donor including the backbone of pBluescript II SK (+) can be inserted into fibroin heavy chain through NHEJ. The inserted backbone cannot be expressed due to the incorporated 3' stop codon in the construction of HC-NHEJ donor. The gene cassette, including part of the FibH N-terminal, eGFP, spider silk gene, DsRed, and the C-terminal of FibH, expressed its entirety under the endogenous FibH promoter.

Transgenic Silkworm Isolation.

A purebred silkworm strain (diapause strain, Haoyue) was used for transformations as it has a white cocoon and high silk production, which facilitates detection of the eGFP-tagged and DsRed-tagged spider silk protein in transgenic cocoons. Microinjection has traditionally been used as a standard method for transformation of *B. mori* embryos. This method has flaws that are difficult to overcome, such as high cost, low survival rate, time and labor consuming as well as technically demanding operations. Additionally, microinjection can only be applied to non-diapause silkworm eggs. As an alternative, electroporation was used to reduce the time and labor needed, due to its convenience and high efficiency. Electroporation has some disadvantages, such as low transformation rate and the need to establish the appropriate electrical pulse parameters (voltage, time, frequency, time interval, and the media composition) for different species. However, once these parameters are optimized and established, exogenous DNA can be easily delivered into *B. mori* embryos.

The electroporation equipment, CUY21EDIT in vivo square wave electroporator and CUY495P10 chamber and were purchased from Sonidel® Limited. Fresh eggs were collected within 1-2 h after being laid by purebred moths (Haoyue). The electroporation procedure is as follows. a) Prepare electroporation buffer (EP buffer) by adding $ddH_2O$ (385 μl), 2% PVP (polyvinylpyrrolidone) solution (250 μl), 10% Tween 20 (15 μl), 0.1M spermidine solution (50 μl), DNA plasmid(s) solution (100 μl, 1.0 μg/μl) to a 1.5 ml Eppendorf tube and mixed together well; then adding 100 ul 2.5 M $CaCl_2$, mixed well again; b) collect and briefly wash the silkworm eggs spawned within 2-3 h; c) place the eggs (500-1000 eggs) into EP buffer in a 9 cm petri-dish; d) treat the silkworm eggs with pressure reduction by placing the dish with eggs on ice in a vacuum chamber for 10-20 min; e) run electroporation for the eggs on ice by placing them into the electroporation chamber, adding 1 ml EP buffer into electroporation chamber (eggs were cooled prior to electroporation by allowing them to sit in the chamber, on ice, for 2 minutes), and running the electroporation under 15 V, 50 ms (pulse), 75 ms (interval), 10-20 repeats, then leaving eggs in the chamber 10-20 min on ice to allow the eggs to cool; f) place the eggs on ice and leave them for at least 1 h; g) eggs are then placed in a 9 cm petri-dish with 7 cm diameter paper; and h) they are left in the dark at 25° C. for hatching.

Electroporated *B. mori* embryos were raised under the same conditions as the non-transgenic group until cocoons were spun. The composite silkworm/spider fibers of transgenic cocoons emitted both green and red fluorescence, indicating the entire gene construct was inserted due to the presence of both the eGFP and the DsRed proteins.

Figure 3B:
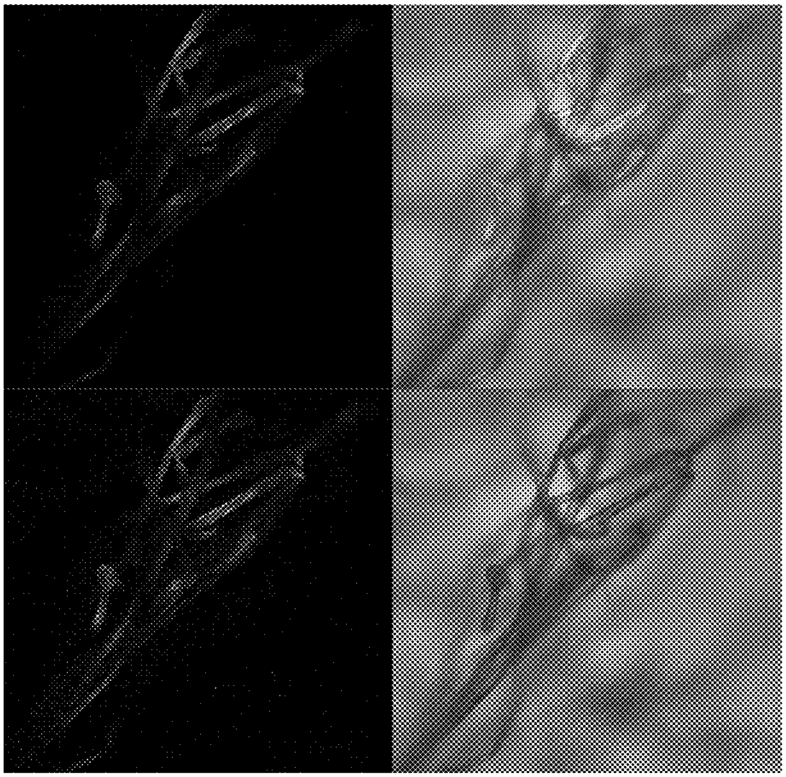
FIGS. 3A and 3B illustrate expression of a composite silkworm/spider/EGFP protein in transgenic cocoons of a $G_0$ HCA group.
Figure 3A:
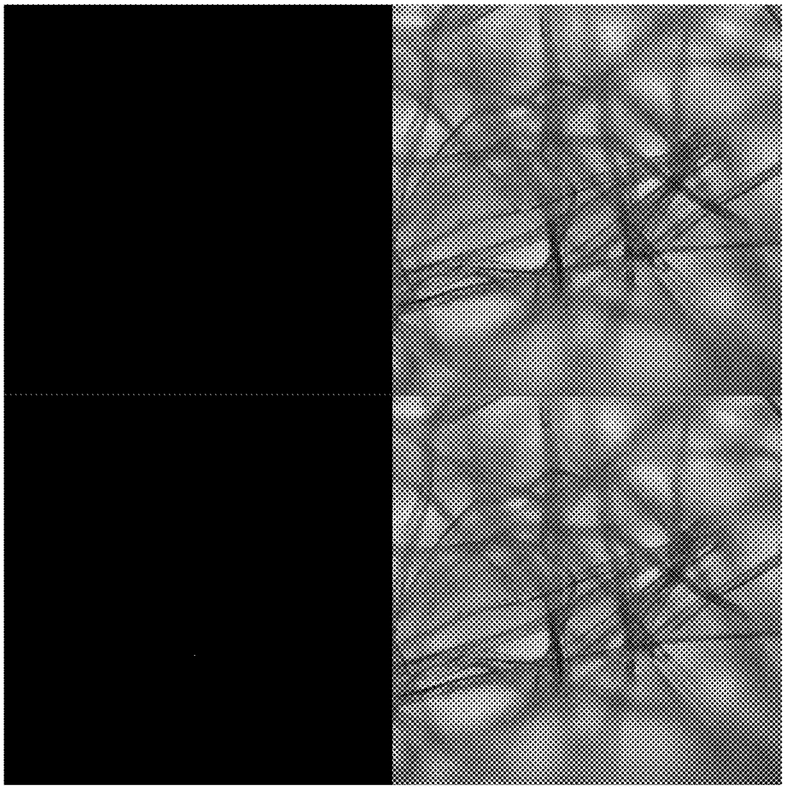
Figure 4A:
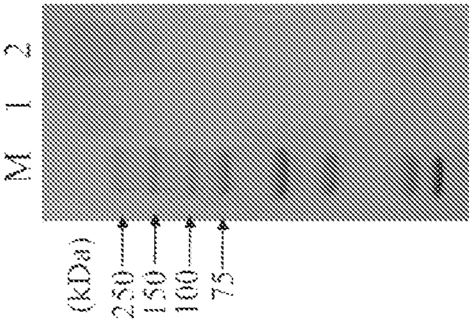
FIGS. 4A, 4B, 4C, and 4D show SDS-PAGE Coomassie blue staining and western blotting of transgenic silkworm gland proteins.
Figure 4B:
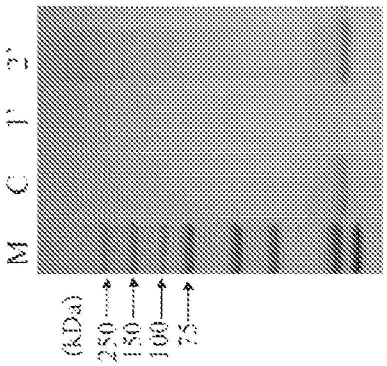
Figure 4C:
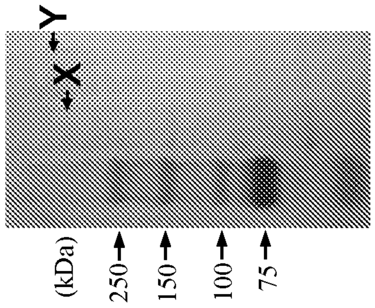
Figure 4D:
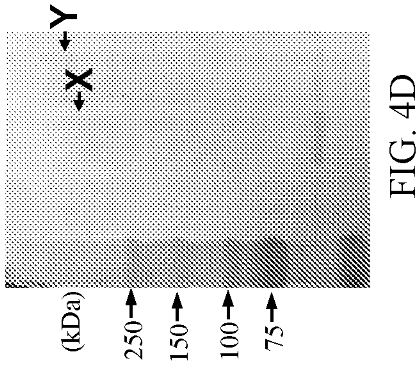

FIG. 3A illustrates the non-transgenic (control) silkworm fibers under the excitation of green and red fluorescence; Upper Left: green fluorescence; Upper Right: red fluorescence; Bottom Left: visible light; Bottom Right: the merged images of visible light, green and red fluorescence. FIG. 3B illustrates the transgenic spider/silkworm fibers under the excitation of green and red fluorescence in HC-NHEJ groups (HCA); Upper Left: green fluorescence; Upper Right: red fluorescence; Bottom Left: visible light; Bottom Right: the merged images of visible light, green and red fluorescence.

Inverse PCR and Junction Sequences.

When silkworms reached the moth stage, the genomes of the $G_0$ transgenic moths were extracted after oviposition.

Genomic DNA was extracted from $G_0/G_1$ transgenic moths using the E.Z.N.A™ Insect DNA Isolation Kit (Omega Bio-Tek, C0926-01). DNA was digested with Sau3AI (NEB, R0169S) and circularized by ligation for 30 min at 16° C. The 3'- and 5'-end genome: transgene junction sequences were amplified using the designed primers reported in Table S4. The first-round of PCR amplification was performed with NEBNext® High-Fidelity 2×PCR Master Mix (NEB, M0541S) and second-round PCRs were performed using Taq PCR Master Mix Kit (Qiagen, No. 201443) on the PCR products, purified by gel extraction, from the first round of amplifications. Amplified fragments were gel-purified (Qiagen, No. 28704) and cloned into the pGEM®-T easy vector system (Promega, A3600) for sequencing. The sequencing data was analyzed using Blast at National Center for Biotechnology Information (NCBI).

Sequencing data showed that the NHEJ allele in the 5' junction is precisely repaired. See FIG. 1. On the other hand, non-precision end repair was evident at the 3' junction. Id. Fortunately, this does not affect expression of the construct. From these results, it was determined that eGFP-tagged and DsRed-tagged composite silkworm/spider silk protein genes were present in the transgenic silkworm glands and that the HC-NHEJ donor fragment had been inserted into the desired location in the intron of the FibH gene. Id.

Analysis of the Composite Silk Protein.

$G_0$ and the $G_1$ adult silkworms were dissected at the 3rd of 5 larval-stages. The glands were removed, treated with 1×PBS and then subjected to −80° C. storage. The middle gland proteins were homogenized in 2×SDS lysis buffer (3% SDS, 6M urea, 40 mM Dithiothreitol, 10% w/v Glycerol, 0.01% Bromophenol blue, and 62.5 mM Tris-HCl pH 6.8), boiled at 100° C. for 15-20 min, loaded onto 4-20% gradient gels (Thermo, Scientific), and run at 100V for 1.5 h. After gel separation (Bio-Rad), proteins were transferred to Immobilon®-P Transfer Membrane (Emd Millipore, IPVH00010) by using Tris-Glycine-Methanol buffer (3.0 g Tris, 14.4 Glycine and 200 ml methanol for 1 L buffer), 45V, overnight. Primary antibodies were commercial eGFP-specific antibody (Thermo scientific, MA1-952), and dsRed2 antibody (Santa Cruz® Biotechnology, sc-101529). Secondary antibody was Anti-Mouse IgG (H+L), HRP Conjugate (Promega, W4021). All antibodies were diluted in blocking buffer (1×TBST with 5% nonfat dry milk). Antibody-antigen reactions were performed using one-step ultra TMB blotting solution (Pierce, Thermo scientific). Transgenic confirmation of the $G_1$ HCl group was performed in the same way as the HCA group using PCR and Western blot analyses.

Proteins extracted from the middle silk glands of non-transgenic or both transgenic groups (the $G_0$ HCA and the $G_1$ HCl) was subjected to immunoblotting to detect eGFP and DsRed proteins using an anti-eGFP or anti-DsRed antibody to determine the presence of the spider silk protein MaSp1 and MiSp1. FIG. 4 illustrates the SDS-PAGE Coomassie staining and western blotting of transgenic silkworm gland proteins. [A and B: Coomassie blue stain; C: Western blot with anti-eGFP as the primary antibody; D: Western blot with anti-DsRed as the primary anti-body; M: Protein Ladder; Lane C: control, non-transgenic silkworm gland; Lan 1 and 1': right middle gland of in the $G_0$ HCA group; Lane 2 and 2': left middle gland of in the $G_1$ HCl group].

Coomassie blue staining of SDS-PAGE gels demonstrated the presence of MiSp1 (~350 kDa) in the transgenic silk gland of the $G_1$ HCl group. MaSp1 or MiSp1 were tagged with both eGFP and DsRed. The positive bands indicated that both proteins were present in the $G_0$ HCA and the $G_1$ HCl groups. See FIG. 4C (lanes 1 (X) and 2 (Y)). The red fluorescence protein DsRed gene was positioned downstream of the exogenous synthetic spider gene MaSp1 or MiSp1 to indicate full expression of the construct. See FIG. 4D (lanes 1' (X) and 2' (Y)).

These results showed that the HC-NHEJ donor in the $G_1$ HCl group were inserted at the same target site as that of the $G_0$ HCA group. See FIG. 4A (lane 2) and FIG. 4B (lane 2). MaSp1 is much more difficult to solvate and therefore was not detected by Coomassie staining in the silk gland of $G_0$ HCA group because this technique is less sensitive than Western blot staining. See FIG. 4A (Lane 1) and FIG. 4B (lane 1).

DsRed Detection in cDna of Transgenic Silkworms mRna.

The transgenic silkworms were dissected at the 3rd larval stage. The glands were removed and washed with 1×PBS (pH 7.4). Glands were stored at −80° C. after absorbing excess moisture using filter paper. The mRNA of the transgenic glands was extracted following the manufacturer's instructions of RNA/DNA/Protein Isolation Reagent (TRI Reagent, No. TR 118/50) and then reverse transcribed into its complementary DNA (cDNA) by using Transcriptor high fidelity cDNA synthesis kit (Roche, No. 05081955001). By using the cDNA as templates, the primary and secondary PCRs were performed with the designed primers (Table S5) using 2×PCR Master Mix (Qiagen, No. 201443). After gel purification (Qiagen, No. 28704), the PCR products were cloned into pGEM®-T easy vector (Promega, A3600) for sequencing. The sequencing data was analyzed using NCBI Blast. All experiments were performed with control (non-transgenic) samples of silkworm glands.

Reverse transcription PCR (RT-PCR) results also showed that the DsRed gene was present in the complementary DNA (cDNA) of the transgenic silkworm glands. See Table 5, illustrating primers for DsRed detection in the genome of transgenic moths. Sequences listed in Table 5 are SEQ ID NOS: 43-48, as listed in order from first to last in the table.

TABLE 5

| Primer No | Name | Sequence (5'-3') | Primer Combinations for PCRs | Template DNA |
|---|---|---|---|---|
| 1 | Dsred-BamHI | ATAGGATCCCGCCTCCTCCGAGAACGTCAT | Primer 1 and 2 used for | cDNA of Transgenic |
| 2 | Dsred-XbaI | TAATCTAGACAGGAACAGGTGGTGGCGG | the first time PCR | silk glands mRNA |
| 3 | HC_DsRed_1_F | CACGAGTTCGAGATCGAGGG | Primer 3 and 4 used for | PCR products from |
| 4 | HC_DsRed_1_R | GCGTCCACGTAGTAGTAGCC | the secondary PCR | the 1st PCR |
| 5 | HC_DsRed_2_F | CCGACATCCCCGACTACAAG | Primer 5 and 6 used for | PCR products from |
| 6 | HC_DsRed_2_R | ACGCCGATGAACTTCACCTT | the secondary PCR | the 1st PCR |

These results show that the synthetic spider silk protein MaSp1 and MiSp1 were fully expressed under the endogenous FibH promoter. In addition, the data indicates that the genes were inherited by the next generation of transgenic silkworms.

Mechanical properties of the composite silk fibers.

To further investigate the mechanical properties of composite silkworm/spider fibers, the $G_1$ HCl offspring of the transgenic moths were raised under the same environmental and diet conditions as their parents to produce silk. The mechanical properties of non-transgenic and composite silkworm/spider fibers were tested under the same environmental conditions (22-25° C. and 40% relative humidity).

The transgenic and control (non-transgenic) cocoon fibers were degummed (0.05% sodium bicarbonate, 0.05% SDS, and 0.01% sodium carbonate solution) at 85° C. for 30-45 min (wt./vol=1:50) until the silk became transparent. Then the degummed fibers were rinsed twice with warm water (50-60° C.) using the same material: solvent ratio. The degummed fibers were dried overnight under room temperature. Individual fibers were gently separated to avoid stretching and deformation and then attached to "C" shaped cards. The gauge length was 19.1 mm and diameters for each fiber were determined by taking an average of nine measurements with a Motic Optical 5A310 light microscope and Motic Images Plus 2.0 software. Each "C" card with the attached fiber was then loaded into a MTS Synergie 100 (MTS Systems) equipped with both a 50N load cell and a custom-made 10 g load cell (Transducer Techniques) for mechanical testing. Using TestWorks® 4 software, the attached fiber was uniaxially tested by pulling the fiber at a speed of 5 mm/min with a data acquisition rate of 120 Hz until the fiber broke. All tests were performed in ambient conditions (20-22° C. and 20-26% humidity). Data were then exported and further analyzed using Microsoft Excel.

FIG. 5 illustrates the mechanical properties of degummed native and transgenic silk fibers [Control: the non-transgenic group (n=57); the $G_0$ HCA group: the first generation of HCA group (silkworms transformed with MaSp1) including HCA-2 (n=35) and HCA-3 (n=35); the $G_1$ HCl group: the second generation of HCl group (silkworms transformed with MiSp1) (n=17).] SD=standard deviation. Silk fibers from native and transgenic silkworms tested under equivalent conditions.

Table 6 illustrates the mechanical properties of the transgenic fibers in both $G_0$ HCA and $G_1$ HCl group compared to the $G_0$ control group.

TABLE 6

| | $G_0$ Control Group n = 57 | | $G_0$ HCA Group HCA-2 n = 35 | | $G_0$ HCA Group HCA-3 n = 35 | | $G_1$ HCI Group n = 17 | |
|---|---|---|---|---|---|---|---|---|
| | Average | SD | Average | SD | Average | SD | Average | SD |
| Diameter (µL) | 9.39 | 1.15 | 10.15 | 0.64 | 10.18 | 0.82 | 9.49 | 1.25 |
| Maximum stress (MPa) | 510.99 | 160.51 | 650.4 | 115.49 | 627.85 | 125.83 | 667.46 | 139.95 |
| Maximum strain (%) | 20.5 | 8.1 | 25.7 | 5.4 | 23.6 | 5.8 | 13.51 | 6.35 |
| Elastic Modulus (GPa) | 8.73 | 2.45 | 7.92 | 2.06 | 7.60 | 2.29 | 15.24 | 4.23 |
| Energy to Break ($MJ/m^3$) | 77.29 | 38.99 | 107.93 | 31.06 | 102.92 | 38.66 | 59.77 | 31.38 |

Table 7 is a comparative table of mechanical properties of the transgenic fibers using a standard two tailed T-test.

TABLE 7

| Compared Materials | Max Stress | Max Strain | Diameter | Elastic Modulus | Energy to Break |
|---|---|---|---|---|---|
| Control, HCA-2 | 0.000027** | 0.0013** | 0.00067** | 0.11 | 0.00018** |
| Control, HCA-3 | 0.00041** | 0.055 | 0.00064** | 0.03* | 0.0028** |
| Control, HCI | 0.00053** | 0.0016** | 0.75 | 1.43E−11** | 0.095 |
| HCA-2, HCA-3 | 0.44 | 0.12 | 0.86 | 0.54 | 0.56 |
| HCA-2, HCI | 0.65 | 3.82E−09** | 0.017* | 5.46E−11** | 3.85E−06** |
| HCA-3, HCI | 0.31 | 6.22E−07** | 0.022* | 2.99E−11** | 0.00021** |

*P < 0.05 considered significant,

**P < 0.01

These results demonstrated that the composite silkworm/spider silk fibers in the $G_0$ HCA group (the $G_0$ HCA2 and the $G_0$ HCA3 lines) were tougher than the non-transgenic fibers. See FIG. 5, and Tables 6 and 7 below.

Figures 5A, 5B, 5C, 5D:
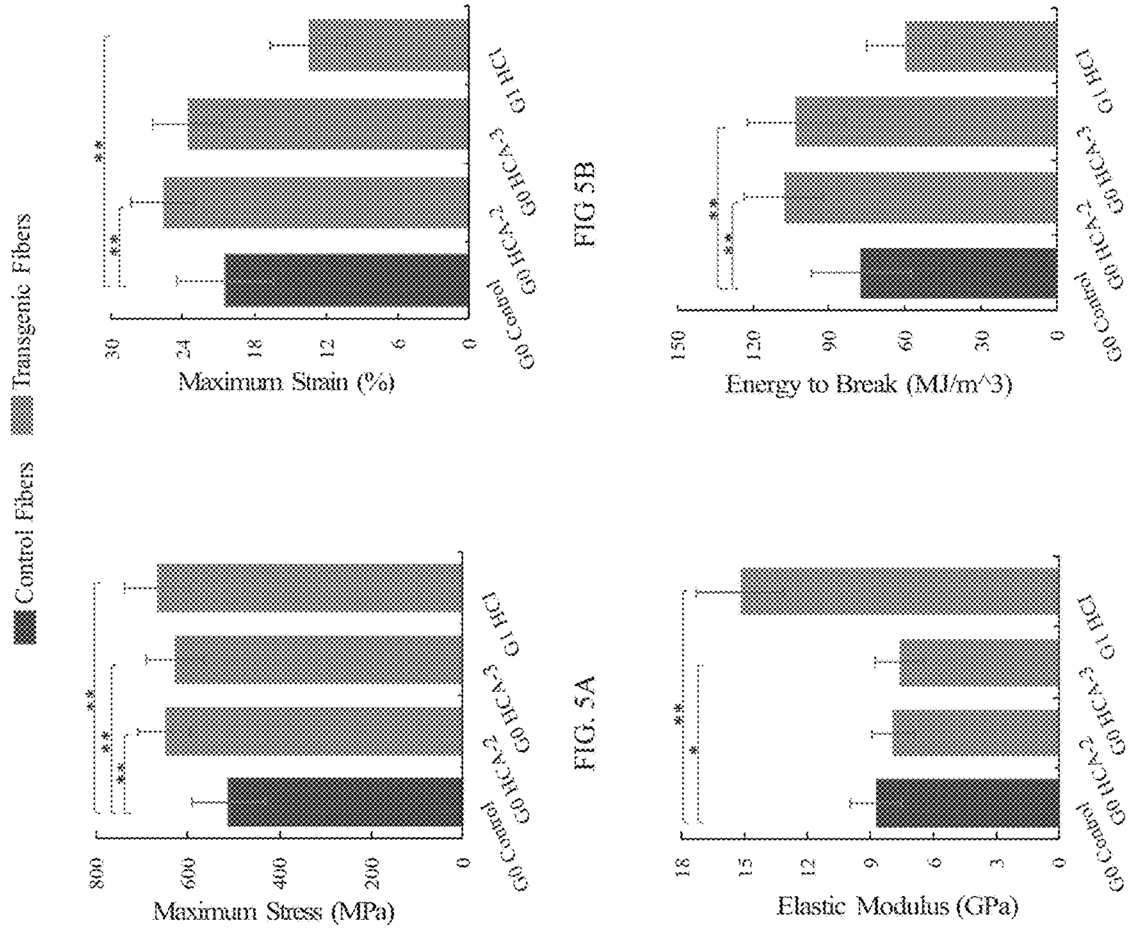
FIGS. 5A, 5B, 5C, and 5D show mechanical properties (stress, strain, elastic modulus, energy to break) of degummed native and transgenic silk fibers.

The values of average maximum stress in the $G_0$ HCA2 and the $G_0$ HCA3 were 650 and 628 MPa (27.3% and 22.9% increases respectively), higher than the non-transgenic group value of 511 Mpa. See FIG. 5A and Table 6. The average maximum stress of the composite silkworm/spider fibers in the $G_1$ HCl group was 667 MPa, showing a 30.6% increase over the control. Id. There was an increase in average maximum strain of the $G_0$ HCA2 and the $G_0$ HCA3 groups of 25.7% and 23.6% compared to 20.5% in the control group. In contrast, the $G_1$ HCl group had an average maximum strain of only 13.5%. Comparisons between transgenic and non-transgenic fibers for maximum stress and maximum strain were statistically significant ($P<0.001$), with the exception of maximum strain in the $G_0$ HCA3. See FIG. 5 and Table 7. While the maximum strain increased for the $G_0$ HCA group, the elastic modulus decreased slightly from 8.73 GPa in the non-transgenic group to 7.92 GPa for the $G_0$ HCA2 and 7.6 GPa for the $G_0$ HCA3. FIG. 5C. On the other hand, the $G_1$ HCl group had a decrease in maximum strain and a statistically significant increase in elastic modulus to 15.24 GPa.

Figure 6:
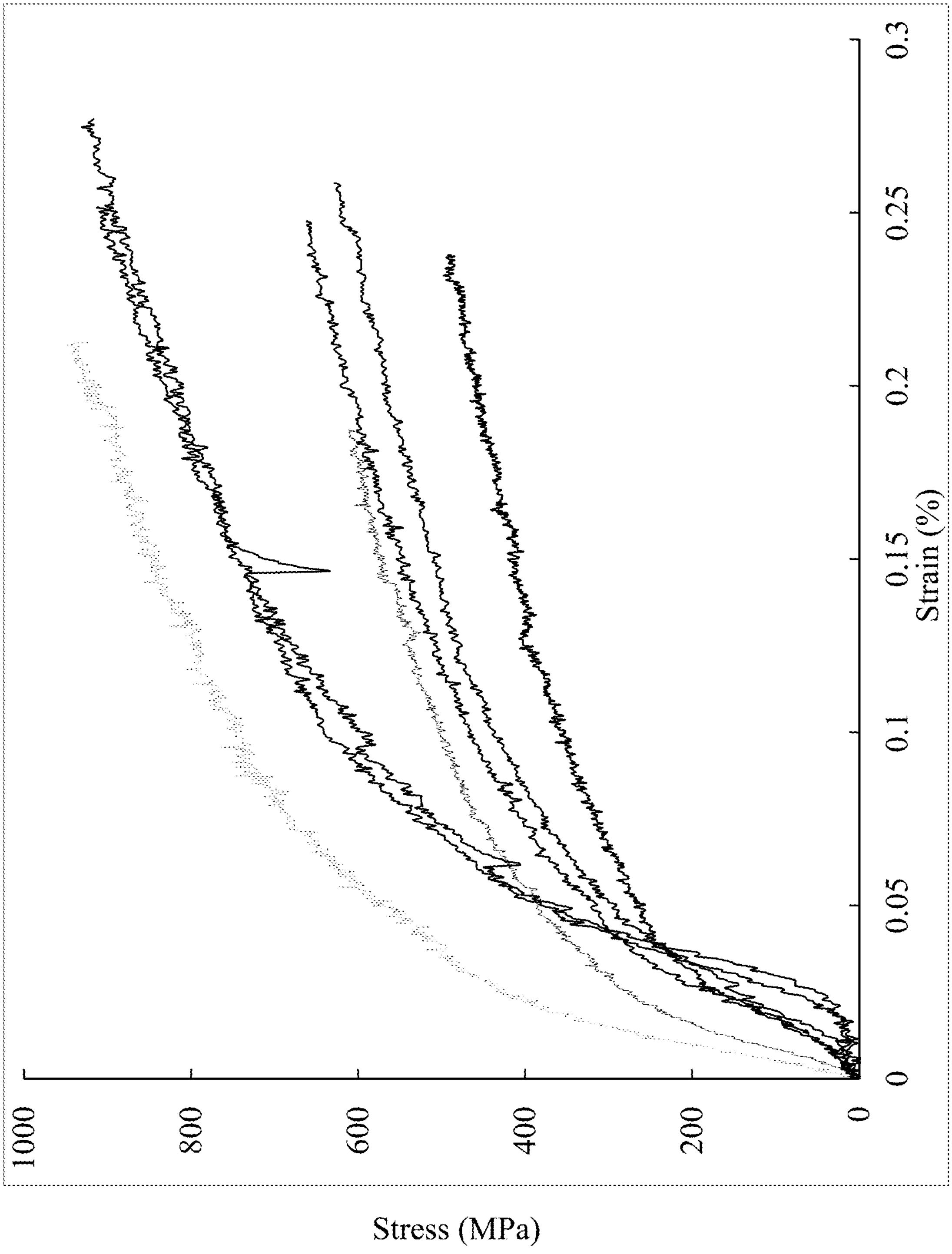
FIG. 6 shows mechanical properties of degummed silk fibers (stress vs. strain) from a control (non-transgenic) group (n=57) and three transgenic groups: the $G_0$ HCA-2 (n=35), the $G_0$ HCA-3 (n=35), and the $G_1$ HCl (n=17).

The toughness (energy to break) of the composite silkworm/spider fibers in the $G_0$ HCA2 (107.93 $MJ/m^3$) and the $G_0$ HCA3 (102.92 $MJ/m^3$) was higher than that in the non-transgenic group (77.29 $MJ/m^3$), while it decreased in the $G_1$ HCl group (59.77 $MJ/m^3$). See FIG. 5D and Table 6. The mechanical properties of the composite silkworm/spider fibers in the $G_0$ HCA group and the $G_1$ HCl group are both stronger than the median non-transgenic fibers when tested in tensile. FIG. 6 shows mechanical properties of degummed silk fibers (stress vs. strain) from a control (non-transgenic) group (n=57) and three transgenic groups: the $G_0$ HCA-2 (n=35), the $G_0$ HCA-3 (n=35), and the $G_1$ HCl (n=17). This figure shows the mechanical properties of silk fibers from each group based on maximum stress. 1: green, the $G_0$ non-transgenic fiber (control), 492.4 MPa; 2 and 5: blue, the median and best composite silkworm/spider silk fibers of the $G_0$ HCA group (HCA-3), 661.5 and 916.93 Mpa, respectively; 3 and 6: red, the median and best composite silkworm/spider silk fibers of the $G_0$ HCA group (HCA-2), 628.8 and 913.03 Mpa, respectively; 4 and 7: purple, the median and the best composite silkworm/spider silk fibers of the $G_1$ HCl group, 610.9 and 921.08 MPa.

Both the $G_0$ HCA and the $G_1$ HCl groups had composite silkworm/spider fibers with maximum stress values over 900 MPa (FIG. 6), which nearly matches the stress of native spider silk.

FTIR-ATR Spectroscopic Characterization of Gland Contents.

Fourier transformed infrared spectroscopy analysis of secondary protein structures on the silks in the glands was performed. A Varian 660-IR instrument with a horizontal single reflection Pike Technologies MIRacle attenuated total reflectance (ATR) module containing a ZnSe crystal was used for all measurements. Prior to producing any spectra, an appropriate background spectrum was obtained. Fresh middle glands of both control and transgenic groups were analyzed immediately after being excised from the silkworm bodies. Each gland was cut into sections beginning at the posterior end of the middle gland (posterior division (MP)) continuing to the anterior end of the middle gland (anterior division (MA)). These sections were then subjected to FTIR-ATR measurements at positions normal to the lumen of the glands. Each sample was gently clamped down prior to performing any readings and residual moisture completely wiped away and cleaned before the next section. A method developed with Resolution Pro Version 5.1.0.822 was used for all measurements that averaged the results for 20 scans over the range of 1000 $cm^{-1}$ to 2000 $cm^{-1}$ with a resolution of 1 $cm^{-1}$ and an aperture setting of 4 $cm^{-1}$ at 4000 $cm^{-1}$.

Spectroscopic analysis of the middle glands of silkworm from both non-transgenic and the $G_0$ HCA transgenic groups revealed both similar and contrasting trends, as shown in FIG. 7, showing FTIR spectra for proteinaceous material measured in various glands [(A) Comparison of anterior segments from non-transgenic glands (bottom plot, green) and morphologically normal transgenic glands (top plot, red). (B) Comparison of middle segments from non-transgenic glands (bottom plot, green) and transgenic glands (13 HCA transgenic, middle plot, red; 8 HCA transgenic, top plot, red). (C) Formation of secondary structure along the gland from posterior (bottom plot) to middle (middle plot) to anterior (top plot) sections in non-transgenic glands. (D) Formation of secondary structure along the gland from posterior (bottom plot) to middle (middle plot) to anterior (top plot) in transgenic glands].

Figure 7A:
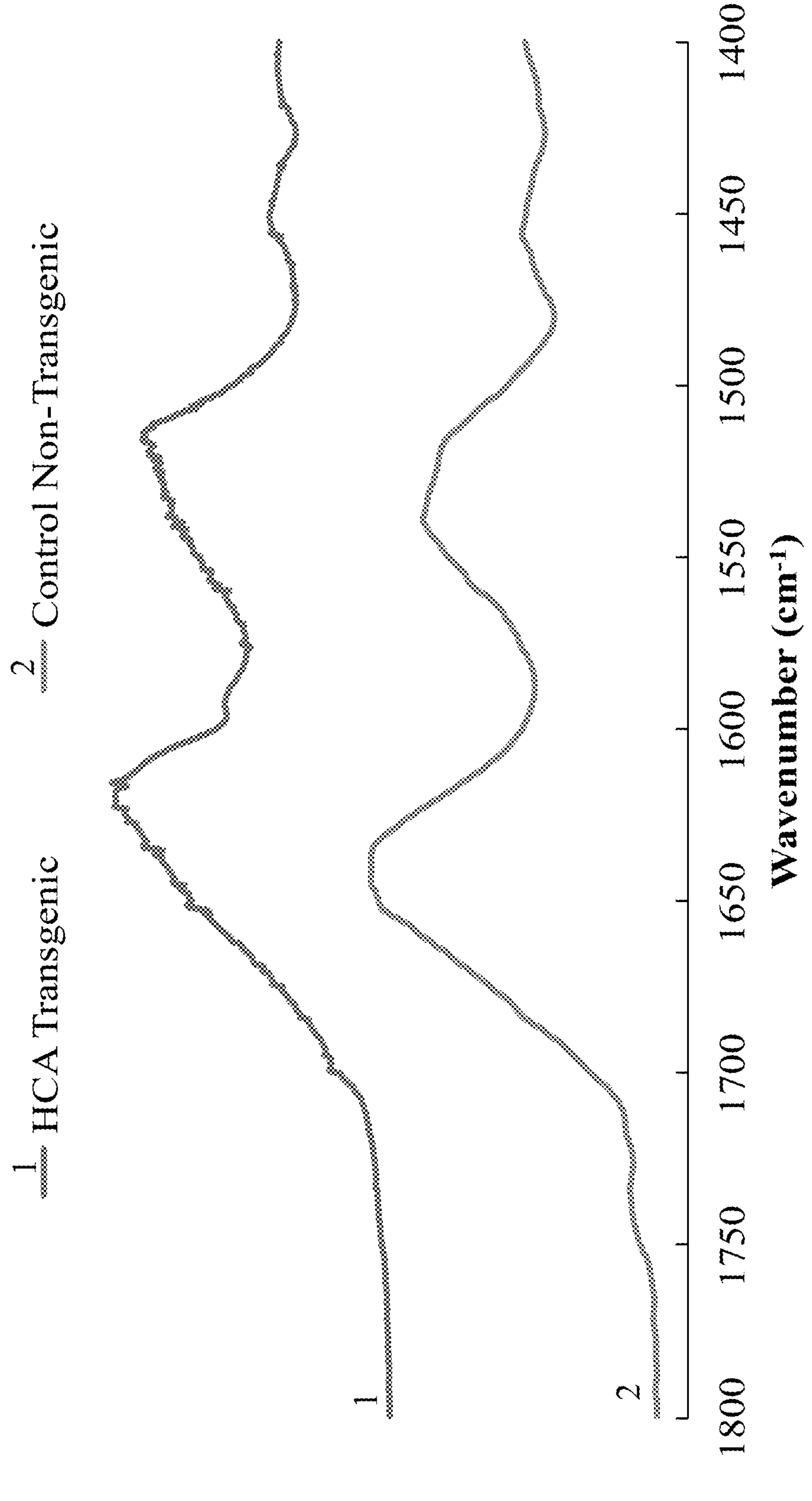
FIGS. 7A, 7B, 7C, and 7D show FTIR spectra for proteinaceous material measured in various glands.
Figure 7B:
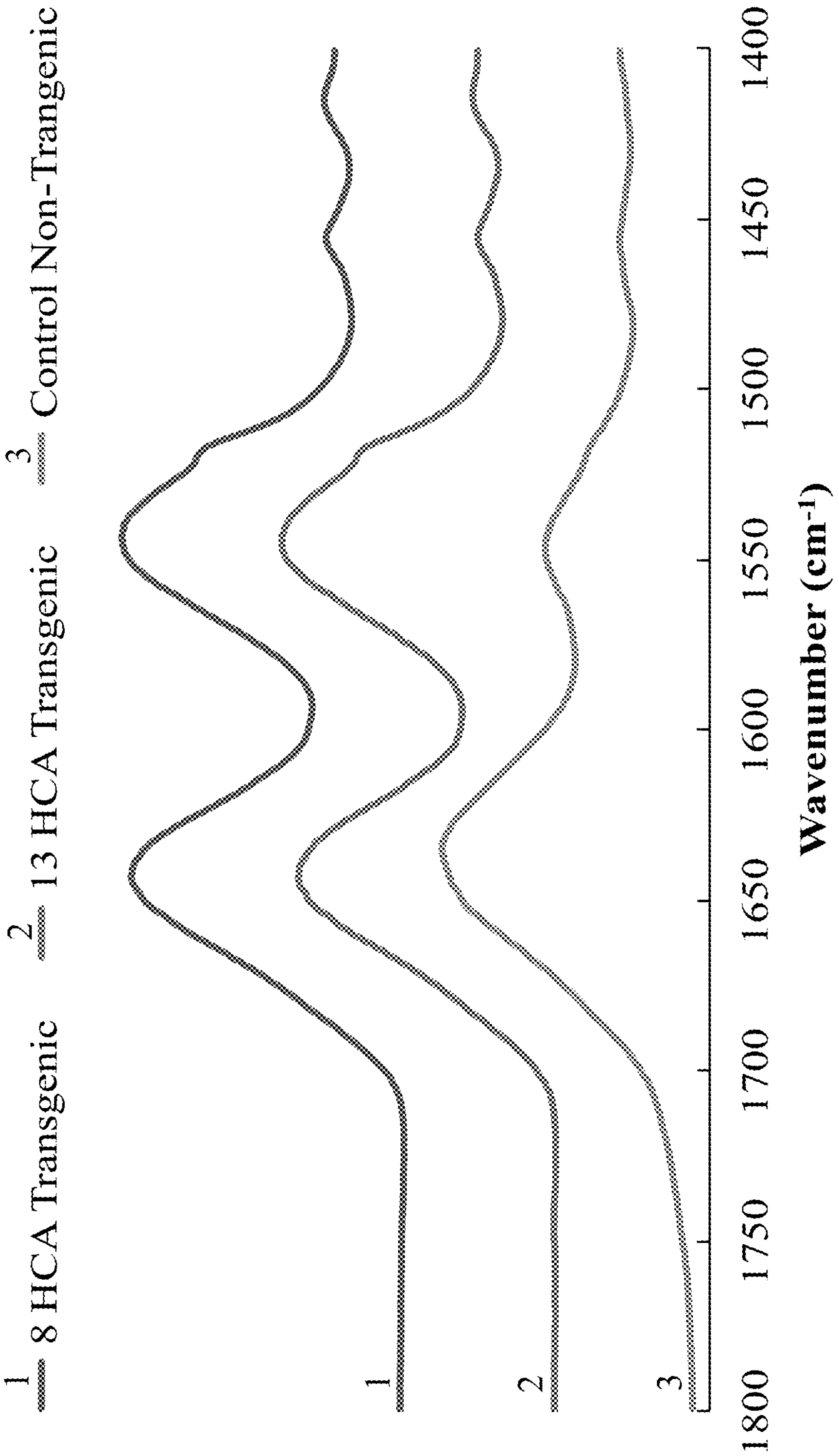

When the secondary structural arrangement of the transgenic glandular material was compared to that of non-transgenic silkworms, the arrangements were highly similar. Both contained amorphous and helical-structures as well as beta-sheets, which are defining hallmarks of all silk proteins. Although the secondary structures present were fairly similar, there were also minor differences between the non-transgenic and the $G_0$ HCA groups. Compared to the non-transgenic group, the most notable difference was that the transgenic glands had increased signal levels around the Amide II region and had an increased shift to beta-sheet rich structures or conformations as shown in FIGS. 7A and B. These trends may be explained by the presence of the spider silk protein, which leads to the observed phenomena due to its primary sequence and motifs that generally contribute to such secondary structures.

Figure 7C:
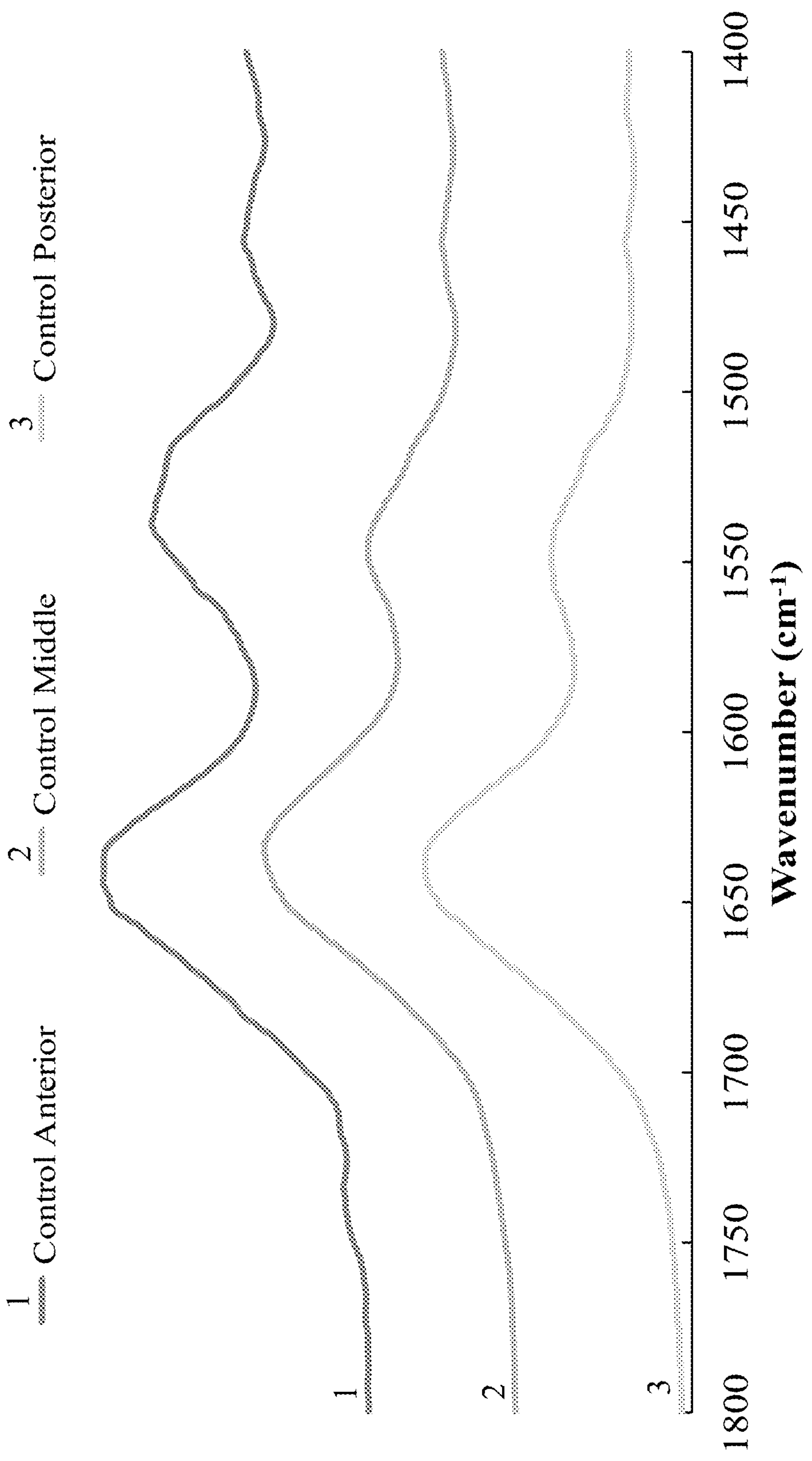
Figure 7D:
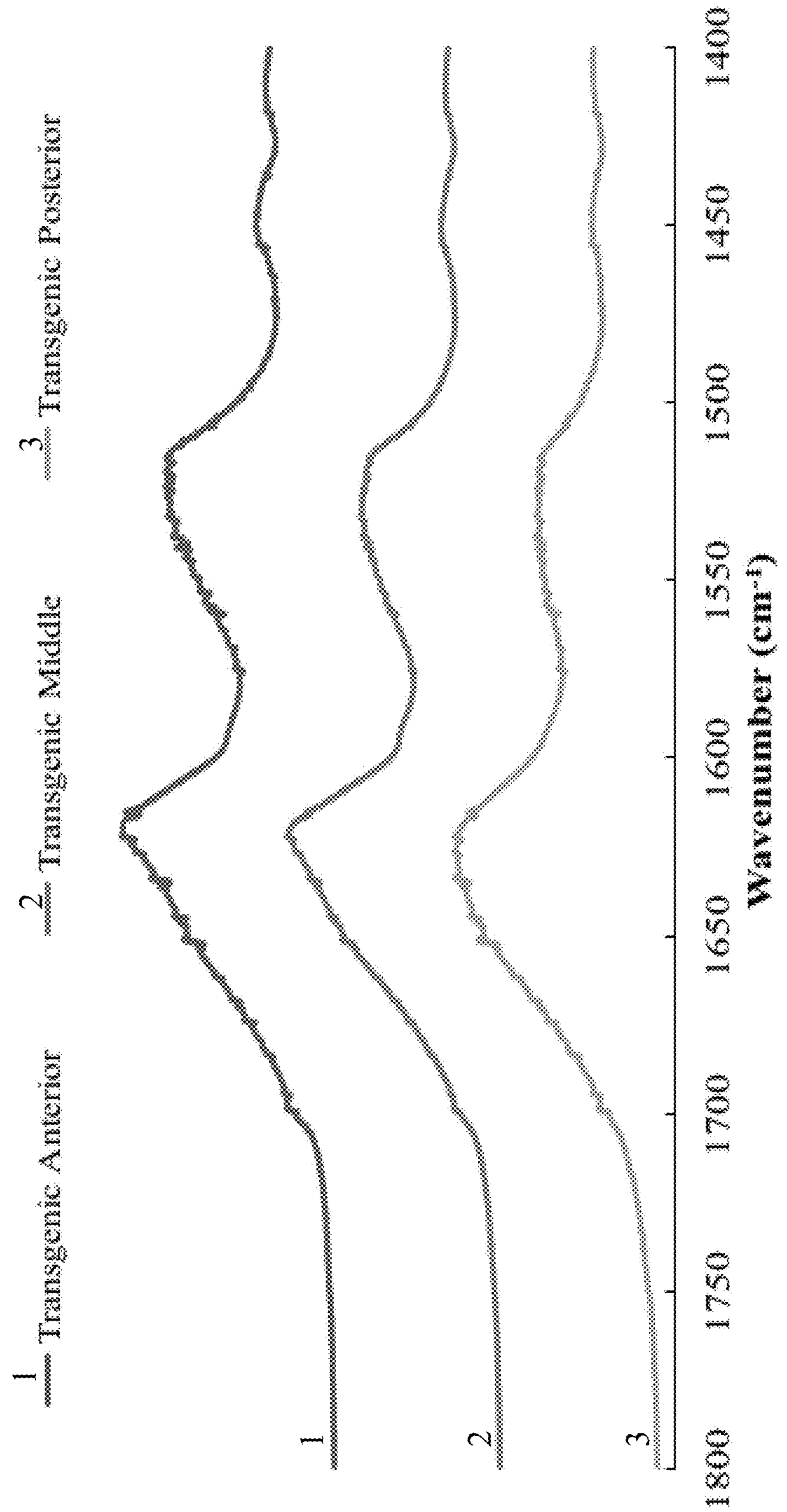

Finally, the organization of silk proteins and more ordered structures are also preserved from non-transgenic to transgenic specimens. FTIR-ATR spectra of protein samples taken from the posterior glands of both groups appear fairly similar and lack any predominant order or structure. At points further along the lumen of the duct, more ordered structures can be seen in the protein structures and the formation of beta-structures is increased, as shown in FIGS. 7C and D. This is especially true for transgenic samples that showed a substantial increase. As the anterior end of the duct is reached and fiber formation starts the increase in secondary structures is clearly present. Characteristic beta-sheets of silks become more apparent when compared to other possible structures. This behavior was demonstrated by both groups of silkworms but was more evident in the transgenic samples (FIG. 7D), which is likely due to the presence of spider silk proteins during the formation. In summary, the properties and structures were present for both groups but the structures of the transgenic samples appeared to be slightly altered to a more beta-rich conformation due to the inclusion of spider silk proteins.

Figure 8:
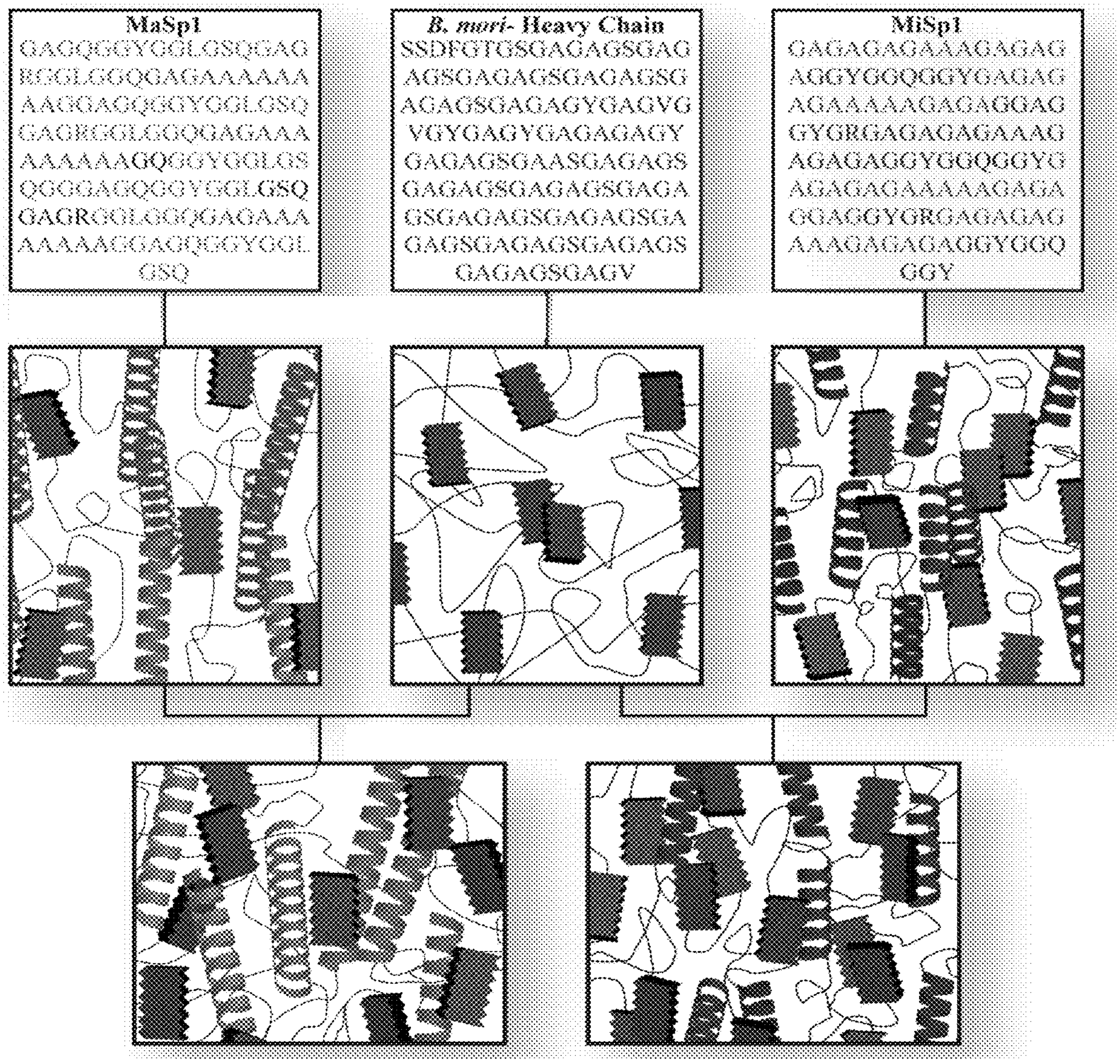
FIG. 8 is a schematic model demonstrating the secondary structure of the composite silkworm/spider silk fibers in the $G_0$ HCA group and $G_1$ HCl group. Upper left: the amino acid sequence of the synthetic spider silk protein MaSp1 [SEQ ID NO:48]. The residues in light blue, red and black indicate the alpha-helixes, beta-sheets and spacers in the central left figure. Upper middle: the amino acid sequence of *B. mori* heavy chain [SEQ ID NO:49]. The residues in green and black indicate the beta-sheets and spacers in the central middle figure. Upper right: the amino acid sequence of the synthetic spider silk protein MiSp1 [SEQ ID NO:50]. The residues in dark blue, red and black indicate the alpha-helixes, beta-sheets and spacers in the central right figure. D: the secondary structure of MaSp1 including $3_{10}$-helixes and β-sheets. E: the secondary structure of *B. mori* heavy chain including β-sheets; F: the secondary structure of MiSp1 including $3_{10}$-helixes and β-sheets. Bottom left and right: the secondary structure of the composite silkworm/spider silk fibers in the $G_0$ HCA group and the secondary structure of the composite silkworm/spider silk fibers in the $G_1$ HCl group. The composite secondary structures of the fusion spider/silkworm fibers respectively transformed with MaSp1 and MiSp1.

FIG. 8 illustrates a schematic model demonstrating the secondary structure of the composite silkworm/spider silk fibers in both the $G_0$ HCA group and the $G_1$ HCl group. [A: amino acid sequence of the synthetic spider silk protein MaSp1 [SEQ ID NO:49]; B: the amino acid sequence of *B. mori* heavy chain [SEQ ID NO:50]; C: the amino acid sequence of the synthetic spider silk protein MiSp1 [SEQ ID NO:51]; D: the secondary structure of MaSp1 including $3_{10}$-helixes and β-sheets; E: the secondary structure of *B. mori* heavy chain including β-sheets; F: the secondary structure of MiSp1 including $3_{10}$-helixes and β-sheets; G: the secondary structure of the composite silkworm/spider silk fibers in the $G_0$ HCA group; H: the secondary structure of the composite silkworm/spider silk fibers in the $G_1$ HCl group.].

The disclosed methods have several advantages over existing technology. First, the disclosed methods are the first successful use of an endogenous FibH promoter to drive expression of large (e.g., greater than 3 kb, greater than 5 kb, etc) exogenous synthetic spider silk genes, which differs significantly from other design approaches based on constructing an expression cassette with an exogenous promoter.

Second, the disclosed methods demonstrate the first time a large synthetic spider silk gene (~10 kb), which is similar to the natural characterized spidroin genes (>9 kb), has been incorporated into the FibH genome of silkworms. A relatively large gene cassette including the synthetic spider silk protein gene (protein size ~300 kDa) has been successfully expressed in its entirety in the silk gland of transgenic silkworms. Previous workers have successfully expressed smaller synthetic spider silk proteins of approximately 120 kDa in piggyBac-based transgenic silkworms.

Third, the composite silkworm/spider silk fibers emit both green and red fluorescence in both the $G_0$ and the $G_1$ generations of transgenic silkworms, indicating the hereditary of transgenic silkworms is stable and reliable. Genome junction testing results show that the synthetic spider silk gene has been integrated into the expected sites of FibH in the genome by the optimized silkworm-specific CRISPR/Cas9 system triggered NHEJ in both $G_0$ and $G_1$ generations of transgenic silkworms.

Fourth, the composite silkworm/spider silk fibers demonstrate improved mechanical properties in both the $G_0$ HCA group and the $G_1$ HCl group, as compared to control silkworm silk fibers. The incorporation of synthetic spider silk protein MaSp1 and MiSp1 enriched both the β-sheets ($(GA)_n$, $A_n$) and $3_{10}$-helixes (GGX) in the composite silkworm/spider silk fibers (FIG. 8). There are no repetitive amino acid regions that form helical structures in the native silkworm silk fibers. The combination of the β-sheets and $3_{10}$-helixes increased both the maximum stress and strain of the composite silkworm/spider silk fibers in the $G_0$ HCA group (FIG. 5). The composition differences of amino acids between MaSp1 and MiSp1 made the composite silkworm/spider silk fibers have different mechanical performances in each transgenic group (the $G_0$ HCA group and the $G_1$ HCl group) (FIG. 5).

Example 2. Spider Silk Transgenes in FibL Intron

To improve the mechanical properties of transgenic silkworm/spider fibers, a synthetic spider silk MaSp1 (172 kDa) gene was incorporated at the genetic locus of the fibroin light chain (FibL) in silkworms by CRIPSR/Cas9 initiated non-homologous end joining (NHEJ). Double strand breaks (DSBs) were created at the sixth intron of the fibroin light chain gene using an optimized CRISPR/Cas9 system. An exogenous spider silk protein MaSp1 was fully expressed under control of the endogenous FibL enhancer and promoter. The resulting transgenic silkworm/spider fibers demonstrated superior mechanical properties in both the first and second generations ($G_1$), indicating genetic stability of the transgenic silkworms.

Design of the CRISPR/Cas9 System.

Two gRNAs (g5 and g6) were designed to target the $6^{th}$ intron of fibroin light chain (FibL) of silkworm gland (Table 8), showing gRNA target sites in the LC-NHEJ project. The gRNAs were sub-cloned into the pGEM®-T easy vector under control of a silkworm specific U6 (sU6) promoter via Gibson Assembly. Expression vectors of the CRISPR/Cas9system (pGEM®-T-sU6-sgRNA and pIEx™-1-eGFP-cas9) were generated. Synthesized sequences of g5 (SEQ ID NO:52) and g6 (SEQ ID NO:53) are shown in Table 8.

TABLE 8

| Name | Target Sequence | Genome Location |
|---|---|---|
| g5 | AGAACTTTAAATTATATCT | M76430.1:13857-13875 |
| g6 | TCACTATGAGACTTAAGCT | M76430.1:13880-13898 |

Light Chain Non-Homologous End Joining Donor (LC-NHEJ Donor).

Figure 9:
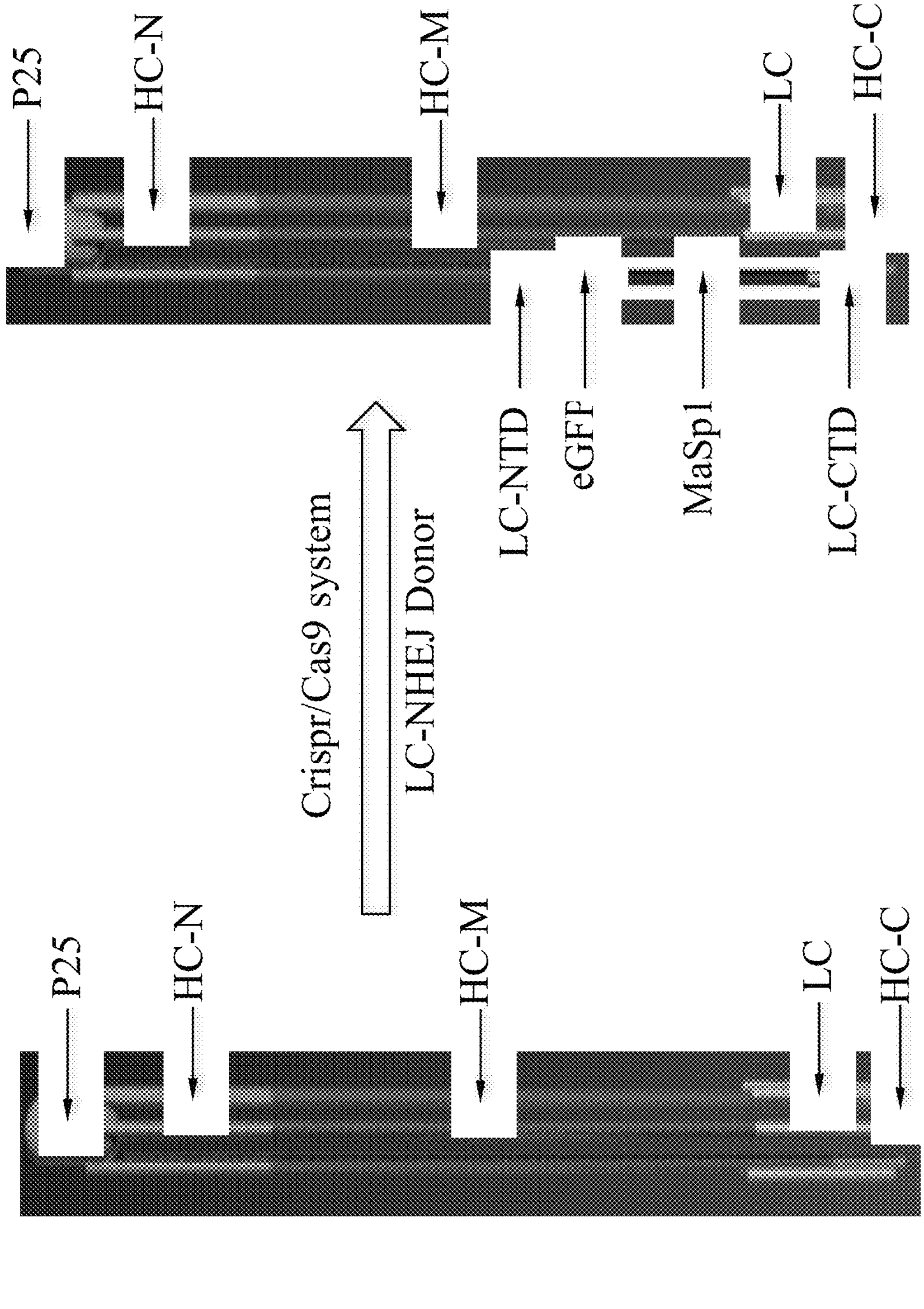
FIG. 9 is a schematic illustration of the engineered fibroin light chain with synthetic spider silk gene MaSp1.

FIG. 9 is a schematic illustration of the engineered fibroin light chain with synthetic spider silk gene MaSp1. LC: fibroin light chain; LC-NTD: N-terminal of fibroin light chain (M76430.1:13461-14090); LC-CTD: the C-terminal of fibroin light chain (M76430.1:14091-14600); HC—N: the N-terminal of fibroin heavy chain; HC-M: the repetitive region of fibroin heavy chain; HC—C: the C-terminal of fibroin heavy chain. MaSp1: the synthetic spider silk gene (MaSp1-6 times).

FIG. 9 shows the N- and C-terminal regions of FibL targeted for LC-NHEJ donor construction. In constructing the LC-NHEJ donor, the N-terminal region of FibL (LC-NTD) included the entire sixth intron flanked by part of the fifth and seventh exons. The C-terminal region of FibL (LC-CTD) includes the entire $7^{th}$ exon and the stop codon of FibL.

Table 9 below shows the primers used to construct the LC-NHEJ donors. The primers in Table 9 have SEQ ID NOs: 54-59, as listed from top to bottom in the table.

TABLE 9

| Name | Sequence(5'-3') |
|---|---|
| KpnI-13461-L-F | ATAGGTACCCCGGTTGCTCAAGTGTTCCACC |
| SalI-14090-L-R | ATTGTCGACGTCATTACCGTTGCCAACGCCTC |
| eGFP-SalI-F | ATAGTCGACGTGAGCAAGGGCGAGGAGCTGTTCACC |
| eGFP-HindIII-R | GCAAGCTTCTTGTACAGCTCGTCCATGCCGAGAG |
| BamHI-14091-R-F | ATAGGATCCTGCGACCGGCTTAGTTGCTAATGCTC |
| SacI-14600-R-R | ATAGAGCTCGTACCCACTGTCCAATCCACCGTC |

Figure 10:
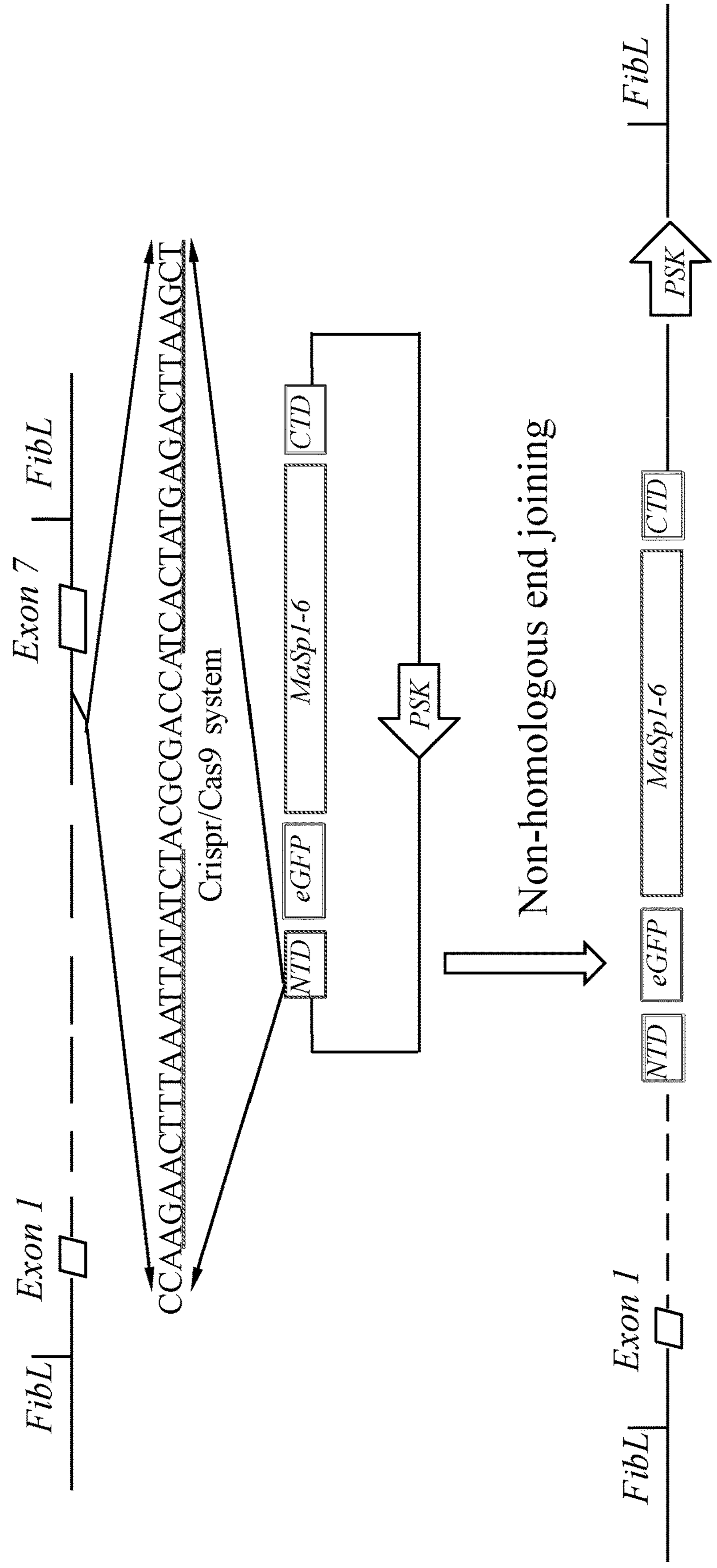
FIG. 10 shows a schematic illustration of the LC-NHEJ strategy. The entire listed sequence is SEQ ID NO:60.

FIG. 10 shows a schematic illustration of the LC-NHEJ strategy used herein. Two gRNAs were targeted to the 6*th* intron of fibroin light chain. NTD and CTD were originally amplified from the fibroin light chain gene then cloned into pBlueScript II. eGFP and the synthetic spider silk gene (MaSp1-6 times) were also sequentially cloned into pBlueScript II. The entire segment of the LC-NHEJ donor was ligated into the fibroin light chain after the generation of DSBs in the 6*th* intron of FibL genome. The g5 sequence identified in Table 8 is shown underlined in red at left (SEQ ID NO:52) and the g6 sequence is shown underlined in brown at right (SEQ ID NO:53). The entire listed sequence in FIG. 10 is SEQ ID NO:60.

Gene fragments of MaSp1-6 (with six repeats), were cloned into pBluescript SK (+) with HindIII and BamHI (NEB) to produce pSK-MASP1 (6). The N-terminal region of silkworm FibL from part of the FibL 6*th* intron/7*th* exon (NTD) was sub-cloned into pSK-MASP1 (6) (using KpnI and SalI sites) to form the pSK-NTD-MASP1 (6) vector. The enhanced green fluorescence protein gene (eGFP) was cloned adjacent to the NTD using SalI and HindIII sites to produce pSK-NTD-eGFP-MASP1 (6). The C-terminal region of silkworm FibL (CTD) includes part of the 7*th* exon and almost all of the C-terminal non-coding region. This was subcloned into the CTD at BamHI and SacI sites to produce the final LC-NHEJ-Donor, pSK-NTD-eGFP-MASP1 (6)-CTD.

The coding region of cas9 was driven by the hr5 enhancer and IE1 promoter in the pIE-1 vector to make sure that cas9 was expressed well in BmN cells and silkworms. The U6 promoter specific for silkworm (sU6) was used to drive the expression of FibL gRNAs, g5 and g6. To preclude the effects of error-prone repairs by NHEJ, the sixth intron of FibL was chosen as the gRNA specific target site (FIG. 9). Thus, gene transcription and protein expression of the LC-NHEJ donor construct were not affected by mutagenesis of the sixth intron of FibL since the intron would be spliced out.

The linearized shuttle vector, the LC-NHEJ construct, can be inserted into FibL at the DSBs through NHEJ (FIG. 10). The transgenic silkworms transformed with MaSp1-6 repeats were named LCA6. The enhanced green fluorescence eGFP gene was used as an indicator to track expression of the LC-NHEJ construct. See FIG. 10. No exogenous enhancer or promoter of FibL was added to the construct of the LC-NHEJ donor, so the transgene cassette can only be expressed by the endogenous FibL enhancer and promoter. The pBlueScript II vector was chosen to shuttle the construct because its original enhancer or promoter has no function in the genome of BmN cells and silkworms. It is noteworthy that the gRNA target site, the sixth intron, was constructed into the LC-NHEJ donor. Thus, an optimized silkworm-specific CRISPR/Cas9system can create DSBs at the defined locus both in the genome of FibL and the LC-NHEJ construct.

Identification of Transgenic Silkworms.

The mature silkworm-specific CRISPR/Cas9 system and LC-NHEJ donors were delivered into fresh silkworm eggs (1-2 h after spawning) through electroporation, as described in Example 1 herein. (silkworm strain: Haoyue). The vectors of the optimized CRISPR/Cas9 system and LC-NHEJ donor were prepared by midi/maxi-preps (QIAGEN).

Figure 11B:
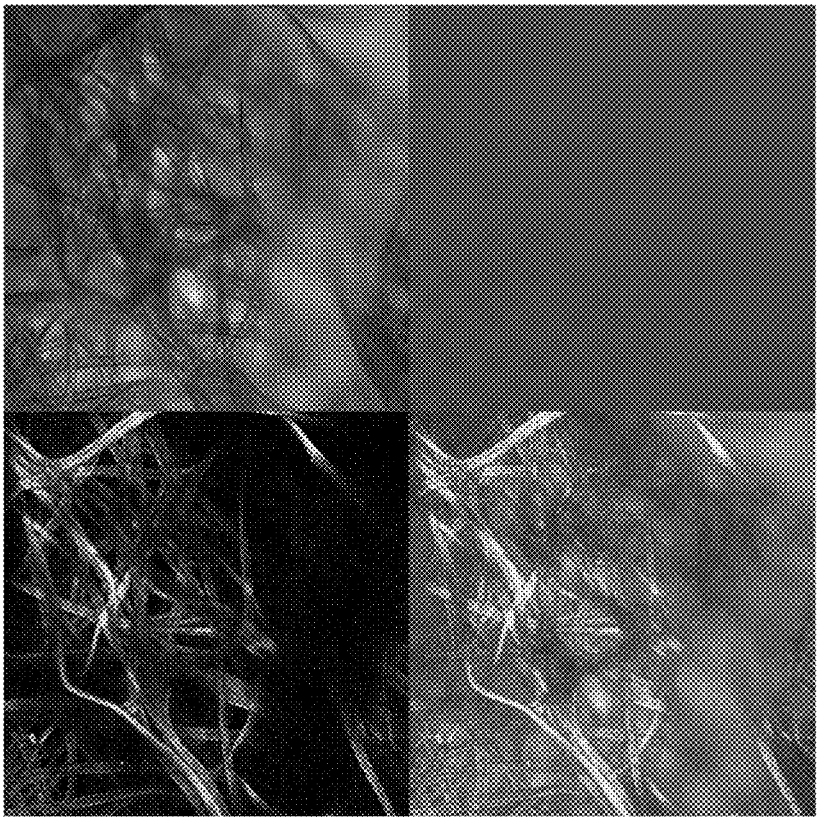
FIGS. 11A and 11B illustrate transgenic silkworm/spider fibers emission of green fluorescence after excitation during confocal microscopy.
Figure 11A:
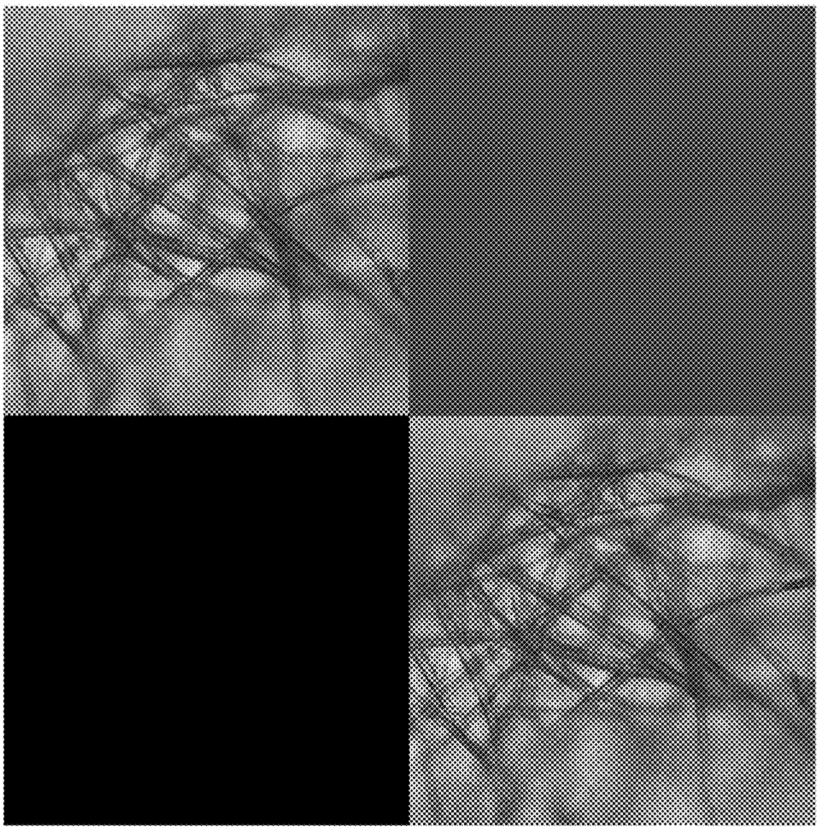
Figure 12:
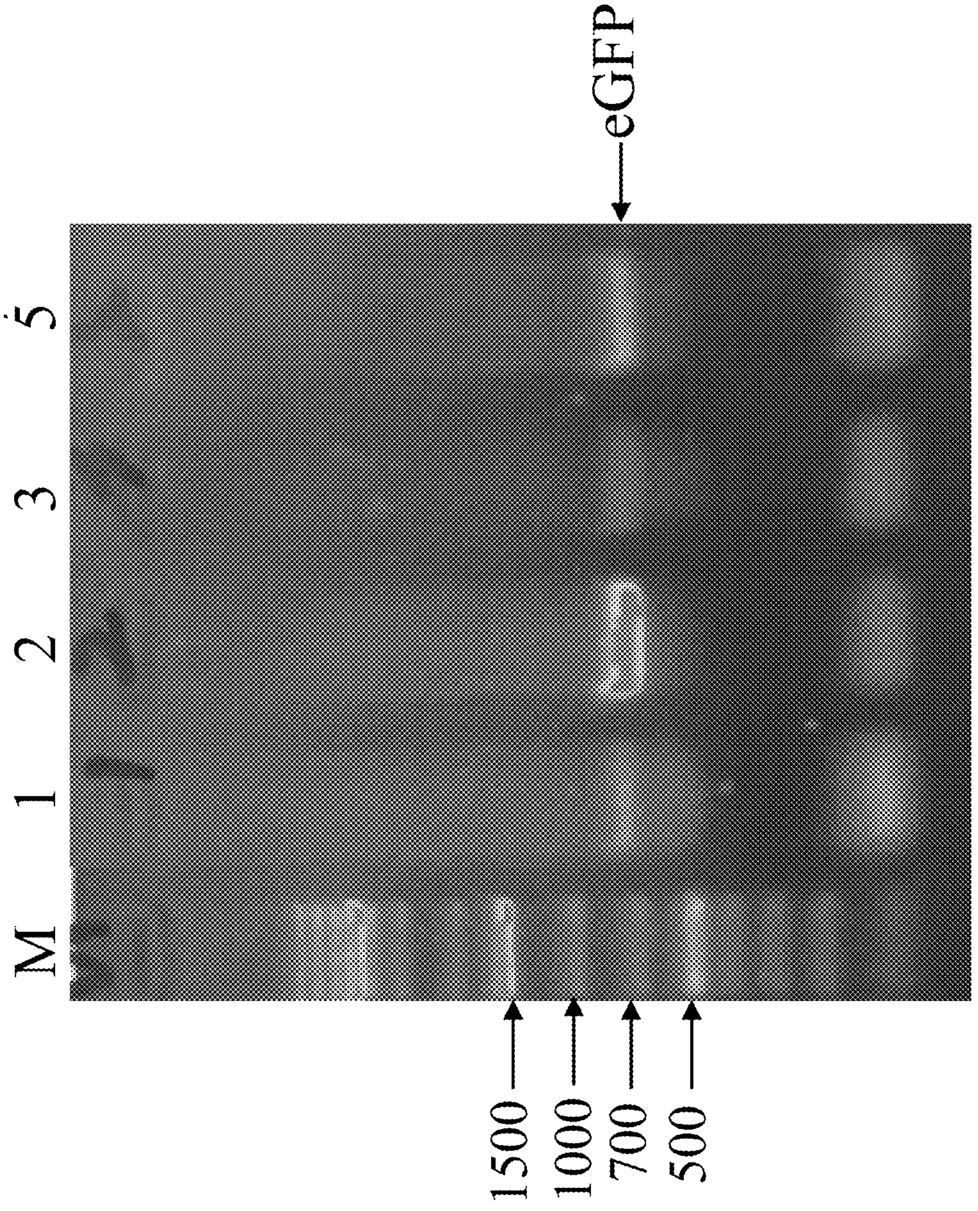
FIG. 12 is an agarose gel showing eGFP in the genome of transgenic moths.

The $G_0$ (first generation) transgenic worms were fed with cooked mulberry chow till the last day of the fifth larval-stage. The transgenic $G_0$ cocoons with pupae inside emitted green fluorescence under the excitation of UV light. These $G_0$ transgenic moths from the transgenic cocoons were raised in order to lay $G_1$ (second generation) transgenic eggs. The hatched $G_1$ transgenic worms were raised to spin $G_1$ transgenic cocoons under the same conditions as parents in a room with specific light (12-hour light vs. 12-hour dark) and humidity (60-80%) conditions. FIG. 11A illustrates the non-transgenic (control) silkworm fibers under the excitation of green fluorescence; Top Left: Green fluorescence; Top right: Natural light; Bottom Left: the combination of green fluorescence and natural light; Bottom Right: Blank. FIG. 11B illustrates the transgenic spider/silkworm fibers under the excitation of green fluorescence in LC-NHEJ group (LCA6); Top Left: Green fluorescence; Top right: Natural light; Bottom Left: the combination of green fluorescence and natural light; Bottom Right: Blank. FIG. 12 is a Western blot showing eGFP expression in the genome of transgenic moths [1, 2, 3 and 5: the genome samples of transgenic moths in LCA6; M: Gene ruler 1 kb plus DNA ladder]. Green fluorescence protein eGFP gene was detected in the genome of $G_1$ transgenic moths after spawning (FIG. 12).

Genome: Junction Testing in Transgenic Silkworm Moths.

Table 10 below shows the primers used for genome: junction testing. The primers in Table 10 have SEQ ID NOs: 61-68, as listed in order from top to bottom in the table.

TABLE 10

| Name | Sequence(5'-3') | Primer Combinations for PCRs |
|---|---|---|
| LC-NHEJ-LJ13201-F | AAGATGGATCAAACTGCACACGGTGTGC | First-time Forward Primer |
| LC-NHEJ-LJ13389-F | AAGAGATTGTACAACTCTCGCAACAGCC | Secondaiy-time Forward Primer |
| LJ-R1 | GTAAACGGCCACAAGTTCAGC | Secondaiy-time Reverse Primer |
| LS-R | TACGGCAAGCTGACCCTGAA | First-time Reverse Primer |
| PSK-F | GGGCGATCGGTGCGGGCCTC | First-time Forward Primer |
| PSK-F2 | TACGACTCACTATAGGGCGA | Secondaiy-time Forward Primer |
| LC-NHEJ-RJ14589-R | CCAATCCACCGTCTTTGGGT | Secondary-time Reverse Primer |
| Sac1-14600-R-R | GACGGTGGATTGGACAGTGGGTAC | First-time Reverse Primer |

Genomic DNA was extracted from $G_1$ (second generation) transgenic moths using the E.Z.N.A™ Insect DNA Isolation Kit (Omega Bio-Tek, C0926-01). The 3'- and 5'-end genome: transgene junction sequences were amplified using the designed primers. The first PCRs were performed with NEBNext® High-Fidelity 2×PCR Master Mix (NEB) and the second PCRs were performed using Taq PCR Master Mix Kit (Qiagen) after purification of the first-time PCR products by gel extraction (Qiagen). Amplified fragments were gel-purified (Qiagen) and cloned into pGEM®-T easy vector system for sequencing (Promega). Sequencing data was analyzed using the NCBI Blast program.

Figure 14:
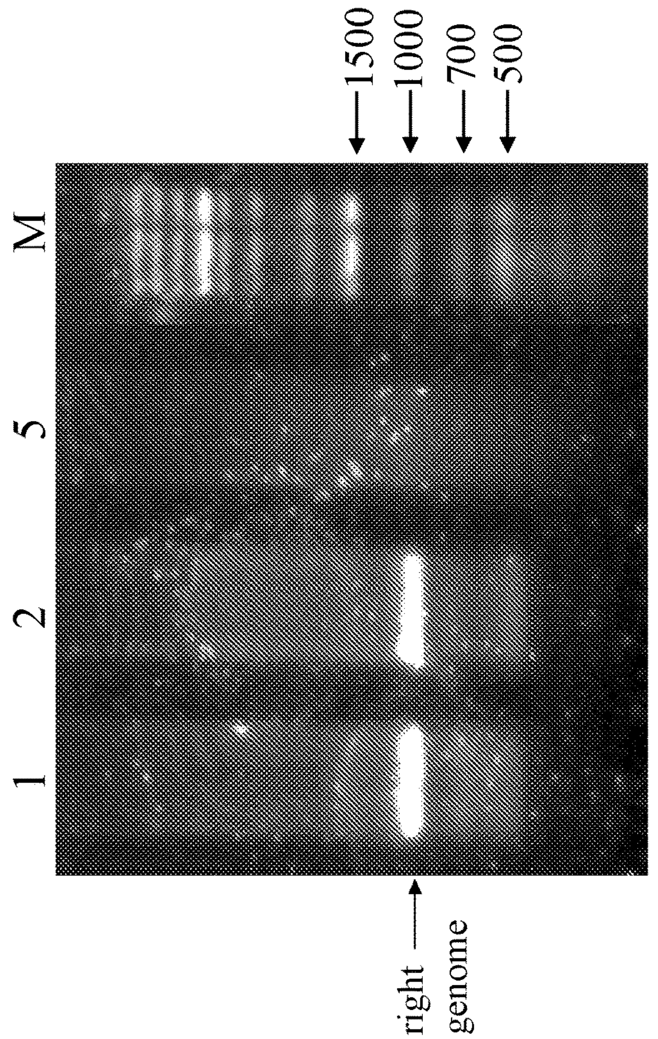
FIG. 14 is an agarose gel illustrating detection of right genome: junction in transgenic moths.
Figure 13:
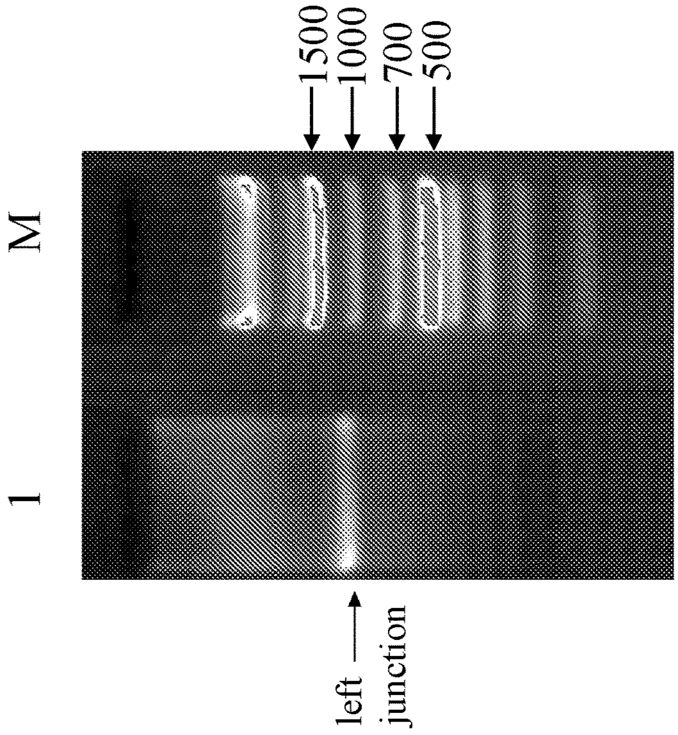
FIG. 13 is an agarose gel illustrating detection of left genome: junction in transgenic moths.

FIG. 13 illustrates detection of left genome: junction in transgenic moths [1: the left junction PCR product of LCA6; M: Gene Ruler 1 kb plus DNA ladder]. FIG. 14 illustrates detection of right genome: junction of the transgenic moths [1, 2, 3 and 5: the genome samples of transgenic moths in LCA6. M: Gene ruler 1 kb plus DNA ladder].

Figure 15B:
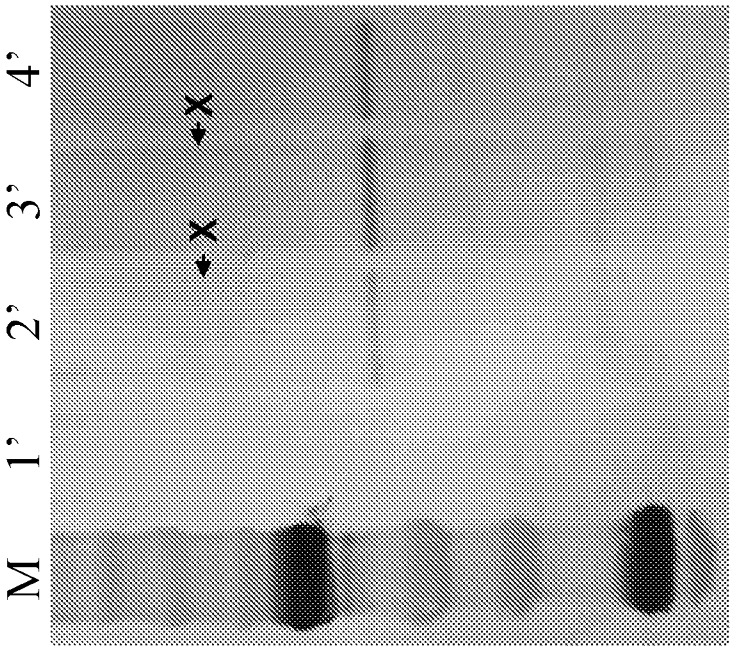
FIG. 15A is a Coomassie blue stained gel and FIG. 15B is a Western blot for detection of eGFP protein in the transgenic silk glands of LCA6.
Figure 15A:
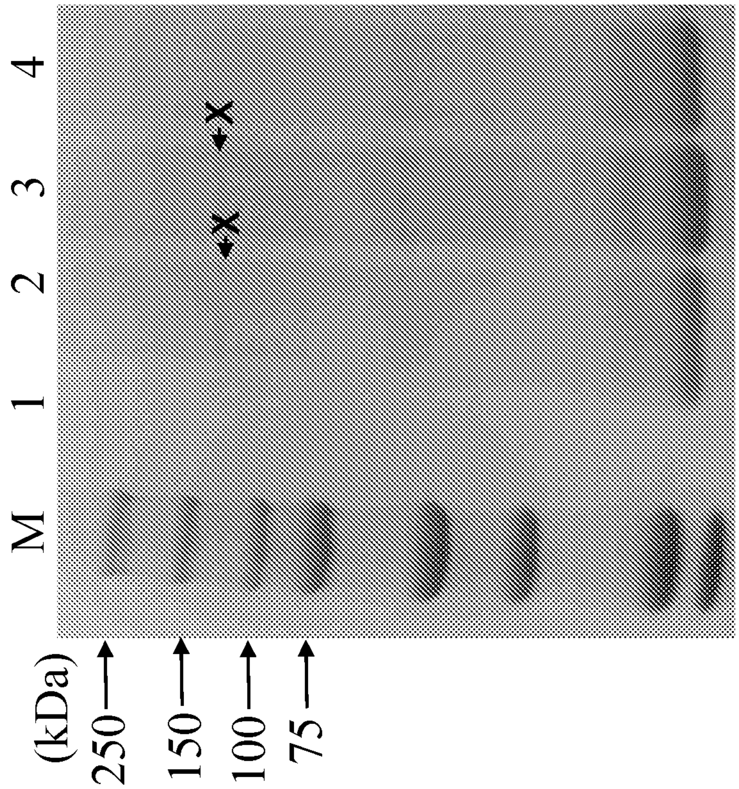

PCR investigation of the left and right genome: junction showed that the LC-NHEJ construct had been successfully inserted at the expected FibL locus in the genome of transgenic moths. (FIG. 13 and FIG. 14). These results indicated that the eGFP-tagged synthetic spider silk protein MaSp1 gene had been successfully incorporated at the FibL target site and was stably inherited through $G_0$ to $G_1$ under the control of the endogenous FibL enhancer and promoter.

at about 130 kDa (FIG. 15). The stronger bands at 60 kDa are either due to translation pauses or cleaved spider silk protein MaSp1 which occurred during the process of dissolution.

Mechanical Testing and Analysis of Silk Fibers.

The mechanical properties of the transgenic silkworm/spider silk fibers were tested in a similar manner to Example 1, herein.

Transgenic silkworm/spider silk fibers (in the $G_1$ LCA6 group) were analyzed by mechanical testing after degumming under the same testing conditions as the control, non-transgenic group (22-25° C. and 40% humidity). FIG. 16 illustrates the mechanical properties of the transgenic silkworm/spider silk fibers in the second generation of LCA6 group [Control: a non-transgenic group with n=57; LCA6: the second generation of the transgenic silkworm/spider silk fibers with MaSp1-6 (n=26). **P<0.001].

Table 11 below reports data showing the mechanical performance of the transgenic silkworm/spider fibers in LC-A6 groups.

TABLE 11

| | Control Non-Transgenic n = 57 | | LCA6 Transgenic n = 26 | | Native Dragline n = 24 | |
|---|---|---|---|---|---|---|
| | Average | SD | Average | SD | Average | SD |
| Diameter (μL) | 9.39 | 1.15 | 7.90 | 1.07 | 2.41 | 0.48 |
| Maximum stress (MPa) | 510.99 | 160.51 | 781.45 | 134.97 | 1432.99 | 336.42 |
| Maximum strain (%) | 20.5 | 8.1 | 20.09 | 7.93 | 11.06 | 3.73 |
| Elastic Modulus (GPa) | 8.73 | 2.45 | 15.95 | 7.02 | 12.56 | 8.21 |
| Energy to Break ($MJ/m^3$) | 77.29 | 38.99 | 105.97 | 55.88 | 77.45 | 34.85 |

Qualitative Detection of Transgenic Silkworm/Spider Protein.

Adult silkworms were dissected on the third day of the fifth larval-stage to remove their silk glands. The glands were treated with 1×PBS and then stored at −80° C. The middle gland proteins were homogenized with 2×SDS lysis buffer (3% SDS, 6 M urea, 40 mM Dithiothreitol, 10% w/v Glycerol, 0.01% Bromophenol blue, 62.5 mM Tris-HCl pH 6.8), boiled at 95° C. for 15-20 min and loaded onto 4-20% gradient gels (Thermo) at 100 V for 1.5 h. Proteins were transferred to a PVDF membrane after gel separation (Bio-Rad). Primary antibodies were commercial the eGFP-specific antibody (Thermo Scientific, cat #: MA1-952), and dsRed2 antibody (Santa Cruz® Biotechnology, sc-101529). The secondary antibody was Anti-Mouse IgG (H+L), HRP Conjugate (Promega, W4021). All antibodies were diluted in blocking buffer (1×TBST with 5% nonfat dry milk) according to the manufacturer's instructions. Antibody-antigen reactions were performed with the one-step ultra TMB blotting solution (Pierce, Thermo Scientific).

FIG. 15 shows the Coomassie blue stained gel and Western blot results [A: Coomassie blue stained gel; B: Western blot. M: protein marker; 1 and 1': negative control; 2, 2' and 3, 3': transgenic silk glands of LCA6; 4 and 4': non-transgenic silk glands. The arrows showed the anti-eGFP positive bands indicating the presence of the synthetic spider silk protein MaSp1 in LCA6].

Figures 16A, 16B, 16C, 16D:
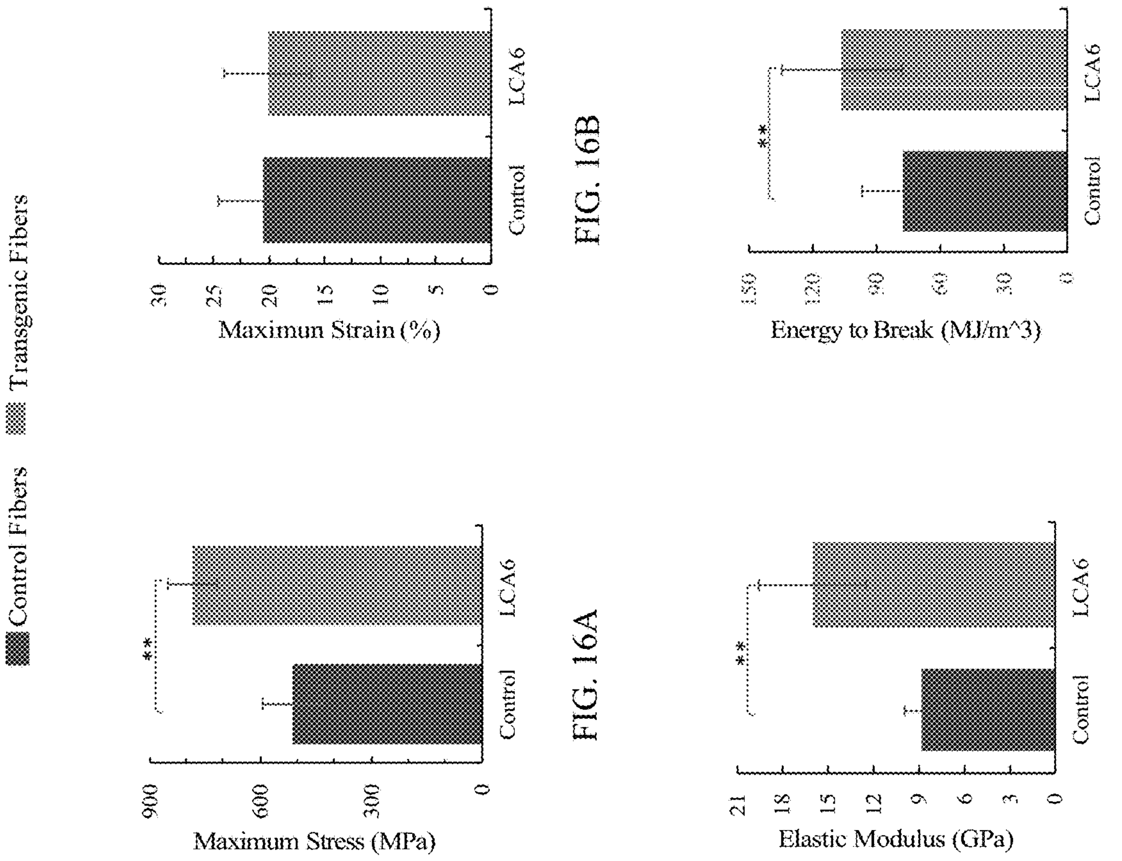
FIGS. 16A, 16B, 16C, and 16D illustrate the mechanical properties of the transgenic silkworm/spider silk fibers in the second generation of LCA6 group.

The synthetic spider silk protein MaSp1 tagged with eGFP showed indistinct bands in the Coomassie blue stained SDS-PAGE (FIG. 15, lanes 1 and 2, "X"); however, the proteins were identified using the anti-eGFP primary antibody, in the Western blot (FIG. 15, Lanes 1' and 2', "X"). This demonstrated that the synthetic spider protein MaSp1 was successfully inserted into the fibroin light chain to form a chimeric silkworm/spider protein with a molecular weight The stress vs. strain results showed that the transgenic silkworm/spider silk fiber had better mechanical properties than fibers in the control group (FIG. 16 and Table 11). The average maximum stress of the transgenic silkworm/spider silk fibers was 781.45 MPa, over 50% higher than the control fibers at 510.99 MPa (FIG. 16 and Table 11). The average elastic modulus of the transgenic silkworm/spider silk fibers was 15.95 GPa, about 83% higher than the control fibers at 8.73 GPa (FIG. 16C and Table 11). The average energy to break of the transgenic silkworm/spider silk fibers was 105.97 $MJ/m^3$, about 37% higher than the control fibers at 77.29 $MJ/m^3$. This demonstrated that the transgenic silkworm/spider silk fibers in the $G_1$ LCA6 group are much stronger than the control fibers.

Figure 17:
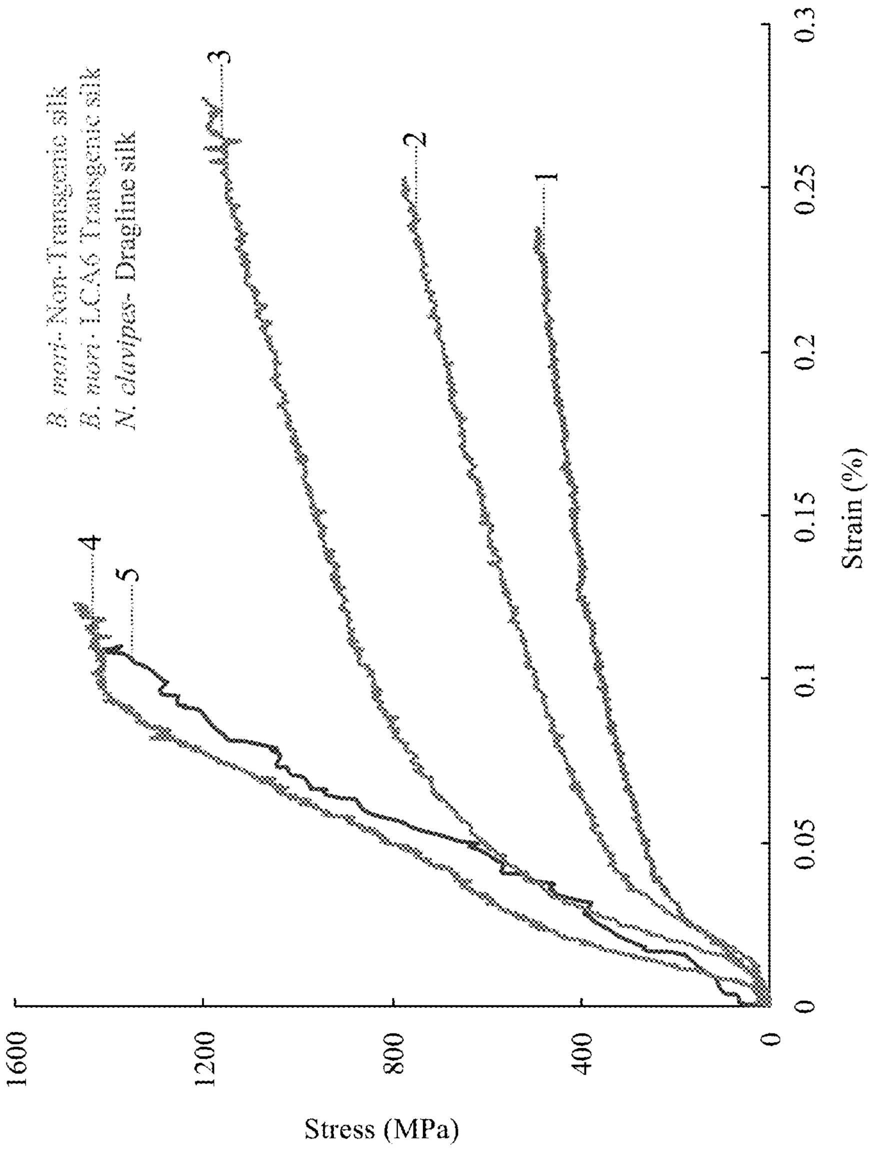
FIG. 17 illustrates the stress vs. strain of the mechanical properties of the degummed transgenic silkworm/spider silk fibers in LCA6 and in the control group. 1: the control (non-transgenic) fibers, 489 MPa; 2: the median transgenic spider/silkworm fibers in the $G_1$ LCA6 group, 776 MPa; 3 and 4: the very best transgenic spider/silkworm fibers in the $G_1$ LCA6 group, 1204 and 1475 MPa; 5: native spider dragline silk (*N. clavipes*), 1375 MPa. Silk fibers from control and transgenic groups tested under equivalent conditions.

FIG. 17 illustrates the stress vs. strain of the mechanical properties of the degummed transgenic silkworm/spider silk fibers in LCA6 and in the control group [1: the control (non-transgenic) fibers, 489 MPa; 2: the median transgenic silkworm/spider silks from the second generation of LCA6 group, 776 MPa; 3 and 4: the best transgenic silkworm/spider silks for extension and tensile strength respectively from the second generation of LCA6 group, 1204 and 1475 MPa; 5: native spider dragline silk (*N. clavipes*), 1375 MPa. n=26].

The highest maximum stress values of the transgenic silkworm/spider silk fibers were 1204 and 1475 MPa. These mechanical properties are close to or better than values for native spider dragline silk (*N. clavipes*), with maximum stress of 1375 MPa (data collected under the same testing conditions as the transgenic silkworm/spider silk fibers) (FIG. 17).

Figure 18:
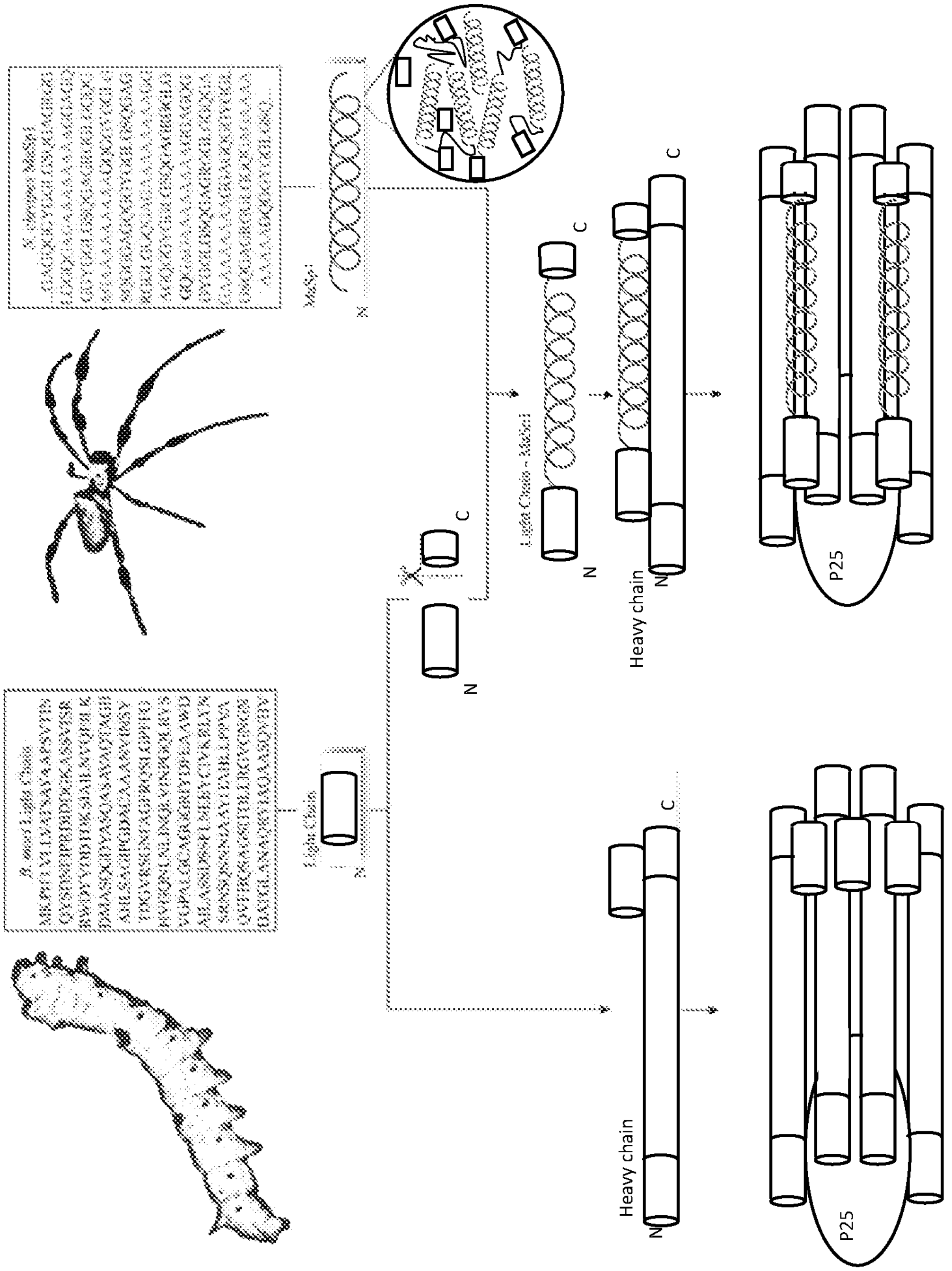
FIG. 18 is a schematic model demonstrating the formation of the composite silkworm/spider silk fibers in the $G_1$ LCA group.

FIG. 18 is a schematic model demonstrating the formation of the composite silkworm/spider silk fibers in the $G_1$ LCA group. *B. mori* light chain is SEQ ID NO:69 and *N. clavipes* MaSp1 protein sequence is SEQ ID NO:70. As provided in the present disclosure, the synthetic spider ampullate silk gene MaSp1 was incorporated into the fibroin light chain of silkworms through CRISPR/Cas9 initiated non-homologous end joining. The donor plasmid (LC-NHEJ vector) has MaSp1 and eGFP flanked by part of the fibroin light chain as N-/C-terminals. The transgenic silkworms expressed spider ampullate dragline silk protein and as a part of the silk fibroin light chain proteins.

Transgenic silkworm/spider fibers showed superior mechanical performance in stress strain testing. Due to integration of the spider silk protein MaSp1 in the FibL of transgenic silkworm/spider fibers, the average maximum stress in LCA6 group is about 50% higher than the control group. The best transgenic silkworm/spider fibers have mechanical properties similar to native spider dragline silk fibers. The spider silk protein MaSp1 is enriched in β-sheets, which leads to an increase in the maximum stress and elastic modulus of transgenic silkworm/spider fibers. MaSp1 also has the secondary structure Gly-II-helixes which might improve the strain. It was thus surprising that the average maximum strain of the transgenic silkworm/spider fibers was similar to that of the control group. Without wishing to be bound to any particular theory, the reason might be because the strain of the silkworm silk fibers is mainly dependent on the conformation of fibroin heavy chain, the predominant protein. This is supported by the mechanical properties of transgenic silkworm/spider fibers in the heavy chain non-homologous end joining (HC-NHEJ) (Example 1), which show a similar pattern. A portion of the original heavy chain was replaced by the synthetic spider silk protein MaSp1 or MiSp1 in the transgenic silkworm/spider fibers. Both maximum stress and strain increased in the transgenic silkworm/spider fibers in the HC-NHEJ (Example 1) due to the combination of the secondary structure β-sheets and $3_{10}$-helixes in MaSp1 or MiSp1.

Compared to MiSp1, MaSp1 combines longer $3_{10}$-helixes that increase the maximum strain in the HCA group compared to that in the HCl group. The arrangement of amino acids in the spider silk proteins MaSp1 and MiSp1 are similar to that of the native fibroin heavy chain of silkworm silks, which allows them to be integrated in to the silk fibers without major disruptions.

In the light chain non-homologous end joining (LC-NHEJ) experiments (Example 2), more β-sheets of spider silk protein MaSp1 were integrated into the fibroin light chain, with no change of fibroin heavy chain in the transgenic silkworms. In addition, $3_{10}$-helixes of MaSp1 were incorporated into the transgenic silkworm/spider fibers in the LCA6 group where there are no $3_{10}$-helixes in the original silkworm silks. In the HC-NHEJ experiments (Example 1), the β-sheets of the original heavy chain were replaced by spider silk protein with the secondary structure β-sheets and $3_{10}$-helixes of the spider silk protein MaSp1 and MiSp1. Overall, the mechanical properties of the transgenic silkworm/spider fibers in LCA6 group are better than that in the HCA or HCl group. The average maximum stress in the G1 LCA6 group is about 800 MPa, a 20% improvement over the $G_0$ HCA and $G_1$ HCl groups (650 and 667 MPa, respectively). That suggests the mechanical properties of transgenic silkworm/spider protein fibers can be improved by the increased β-sheets and $3_{10}$-helixes provided by the spider silk proteins.

Alternative splicing in the FibL gene could also lead to various expression patterns of the integrated spider silk gene MaSp1. It also can change the protein conformation of transgenic silkworm/spider fibers that affects their mechanical properties. As mentioned before, the fibroin light chain has seven exons while the fibroin heavy chain only has two exons in the silkworm genome. In the LC-NHEJ project, the spider silk gene MaSp1 was integrated at the seventh exon of FibL gene that makes an MaSp1 fusion on the C-terminal end of the FibL gene. The C-terminal exon with the fusion to MaSp1 should be always expressed no matter which kind of alternative splicing happened in the FibL gene of the transgenic silkworm genome. However, in the HC-NHEJ project, the non-homologous insertion of the gene cassette with MaSp1 or MiSp1 generated a new FibH C-terminal without destroying the original FibH C-terminal in the transgenic silkworm genome. During alternative splicing, either the new or the original FibH C-terminal has a chance to be expressed while only expression of the FibH C-terminal with spider silk protein will improve the mechanical properties of transgenic silkworm/spider fibers. This may explain the increased mechanical properties of the LC-NHEJ fibers.

What is claimed is:

1. A transgenic silkworm comprising a stably-integrated exogenous synthetic spider silk gene operably linked to an endogenous silkworm promoter, wherein the exogenous spider silk gene is greater than three kilobases (3 kb) in length, is stably integrated in a sixth intron of a fibroin light chain gene, FibL, wherein the endogenous silkworm promoter is a silkworm-specific U6 promoter and the transgenic silkworm stably expresses the spider silk gene.

2. The transgenic silkworm of claim 1, wherein the exogenous synthetic spider silk gene is operably linked to an endogenous silkworm promoter in the silkworm gland.

3. The transgenic silkworm of claim 1, wherein the exogenous spider silk gene is greater than four kilobases (4 kb) in length.

4. The transgenic silkworm of claim 1, wherein the exogenous spider silk gene is greater than five kilobases (5 kb) in length.

5. The transgenic silkworm of claim 1, wherein the exogenous spider silk gene is ten kilobases (10 kb) in length.

6. The transgenic silkworm of claim 1, wherein the exogenous spider silk gene comprises SEQ ID NO. 25 or SEQ ID NO:26 or a fragment of either thereof.

7. The transgenic silkworm of claim 1, wherein the transgenic silkworm stably expresses the spider silk gene.

8. The transgenic silkworm of claim 1, wherein the exogenous synthetic spider silk gene is stably integrated in an intron of a fibroin heavy chain gene, FibH.

9. The transgenic silkworm of claim 1, wherein the exogenous spider silk gene comprises the MaSp1 gene, MaSp2 gene, Ac1 gene, Flag gene, *Piri* gene or the MiSp1 gene of *Nephila clavipes*.

10. The transgenic silkworm of claim 1, wherein the silkworm is *Bombyx* sp.

11. The transgenic silkworm of claim 10, wherein the silkworm is *Bombyx mori*.

12. A progeny silkworm of the transgenic silkworm claim 1, wherein the exogenous synthetic spider silk gene is stably integrated.

13. A transgenic *Bombyx* silkworm, the silkworm comprising:

a stably-integrated MaSp1 gene or the MiSp1 gene of *Nephila clavipes* synthetic spider silk gene in the intron of the fibroin heavy chain gene FibH and operably linked to the silkworm-specific U6 promoter, wherein the exogenous spider silk gene is greater than three kilobases (3 kb) in length, wherein the transgenic silkworm stably expresses the spider silk gene.

14. The transgenic silkworm of claim 13, wherein the exogenous spider silk gene comprises SEQ ID NO. 25 or SEQ ID NO:26, or a fragment of either thereof.

15. A transgenic silkworm comprising a stably-integrated exogenous synthetic spider silk gene operably linked to an endogenous silkworm promoter, wherein the exogenous spider silk gene is greater than three kilobases (3 kb) in length, wherein the exogenous synthetic spider silk gene is stably integrated in a sixth intron of a fibroin light chain gene, FibL.

16. The transgenic silkworm of claim 15, wherein the endogenous silkworm promoter is a silkworm-specific U6 promoter.

17. The transgenic silkworm of claim 15, wherein the exogenous spider silk gene comprises the MaSp1 gene, MaSp2 gene, Ac1 gene, Flag gene, *Piri* gene or the MiSp1 gene of *Nephila clavipes.*

18. The transgenic silkworm of claim 15, wherein the silkworm is *Bombyx* sp.

19. A transgenic *Bombyx* silkworm, the silkworm comprising:

a stably-integrated MaSp1 gene or the MiSp1 gene of *Nephila clavipes* synthetic spider silk gene in a sixth intron of a fibroin light chain gene, wherein the exogenous spider silk gene is greater than three kilobases (3 kb) in length, wherein the transgenic silkworm stably expresses the spider silk gene.

20. The transgenic silkworm of claim 19, wherein the exogenous spider silk gene comprises SEQ ID NO: 25 or SEQ ID NO: 26, or a fragment of either thereof.

* * * * *

SEQUENCE LISTING

```
<160> NUMBER OF SEQ ID NOS: 71

<210> SEQ ID NO 1
<211> LENGTH: 124
<212> TYPE: DNA
<213> ORGANISM: Artificial Sequence
<220> FEATURE:
<223> OTHER INFORMATION: CRISPR/Cas9 system HC3-mediated targeted
      integration in BmN cells, with wt.: wild-type gene sequence

<400> SEQUENCE: 1

taaggcagta tgtcctaact cgttccagat cagcgctaac ttcgattgaa tgtgcgaaat      60

tttaaggcag tatgtcctaa ctcgttccag atcagcgcta acttcgattg aatgtgcgaa     120

attt                                                                  124


<210> SEQ ID NO 2
<211> LENGTH: 51
<212> TYPE: DNA
<213> ORGANISM: Artificial Sequence
```

<220> FEATURE:
<223> OTHER INFORMATION: XZ2-M13F-T2

<400> SEQUENCE: 2
taaggcatta ccagttagag ctccataact tcgattgaat gtgcgaaatt t 51

<210> SEQ ID NO 3
<211> LENGTH: 61
<212> TYPE: DNA
<213> ORGANISM: Artificial Sequence
<220> FEATURE:
<223> OTHER INFORMATION: XZ3-M13F-T3

<400> SEQUENCE: 3
taaggcagta tgtcctaact gttccagatc agcgctaact tcgattgaat gtgcgaaatt 60
t 61

<210> SEQ ID NO 4
<211> LENGTH: 63
<212> TYPE: DNA
<213> ORGANISM: Artificial Sequence
<220> FEATURE:
<223> OTHER INFORMATION: XZ6-M13-T6

<400> SEQUENCE: 4
taaggcagta tgtcctaact tatttctagc tctaaaacaa ctcgttccag atcagcgcac 60
ttg 63

<210> SEQ ID NO 5
<211> LENGTH: 60
<212> TYPE: DNA
<213> ORGANISM: Artificial Sequence
<220> FEATURE:
<223> OTHER INFORMATION: XZ15-M13F-T3

<400> SEQUENCE: 5
taaggcagta tgtcctaact ttccagatca gcgctaactt cgattgaatg tgcgaaattt 60

<210> SEQ ID NO 6
<211> LENGTH: 60
<212> TYPE: DNA
<213> ORGANISM: Artificial Sequence
<220> FEATURE:
<223> OTHER INFORMATION: XZ16-M13F-T4

<400> SEQUENCE: 6
taaggcagta tgtcctaacg ttccagatca gcgctaactt cgattgaatg tgcgaaattt 60

<210> SEQ ID NO 7
<211> LENGTH: 47
<212> TYPE: DNA
<213> ORGANISM: Artificial Sequence
<220> FEATURE:
<223> OTHER INFORMATION: XZ22-M13-T10

<400> SEQUENCE: 7
taaggcagta tgtcctagcg ctaacttcaa ttgaatgtgc gaaattt 47

<210> SEQ ID NO 8
<211> LENGTH: 60
<212> TYPE: DNA
<213> ORGANISM: Artificial Sequence
<220> FEATURE:
<223> OTHER INFORMATION: XZ25-M13-T13

<400> SEQUENCE: 8
taaggcagta tgtcctaact gtccagatca gcgctaactt cgattgaatg tgcgaaattt 60

<210> SEQ ID NO 9
<211> LENGTH: 55
<212> TYPE: DNA
<213> ORGANISM: Artificial Sequence
<220> FEATURE:
<223> OTHER INFORMATION: XZ29-M13F-T17

<400> SEQUENCE: 9
taaggcagta tgtcctaaca gatcagcgct aacttcgatt gaatgtgcga aattt 55

<210> SEQ ID NO 10
<211> LENGTH: 20
<212> TYPE: DNA
<213> ORGANISM: Artificial Sequence
<220> FEATURE:
<223> OTHER INFORMATION: XZ35-M13F-T23

<400> SEQUENCE: 10
taaggcagta tgtcctaact 20

<210> SEQ ID NO 11
<211> LENGTH: 37
<212> TYPE: DNA
<213> ORGANISM: Artificial Sequence
<220> FEATURE:
<223> OTHER INFORMATION: target sites of gRNA HC-1

<400> SEQUENCE: 11
cactagtgct gcagtcgttc tagacgtgag caagggc 37

<210> SEQ ID NO 12
<211> LENGTH: 34
<212> TYPE: DNA
<213> ORGANISM: Artificial Sequence
<220> FEATURE:
<223> OTHER INFORMATION: target sites of gRNA HC-3

<400> SEQUENCE: 12
cagctagaac attcaatctg aattcgtcga caag 34

<210> SEQ ID NO 13
<211> LENGTH: 55
<212> TYPE: DNA
<213> ORGANISM: Artificial Sequence
<220> FEATURE:
<223> OTHER INFORMATION: Target sites of gRNA HC-1 and HC-3

<400> SEQUENCE: 13
ccagctaata ggtagggaaa acaaagctca taatgtagac cataaaatct cgtgg 55

<210> SEQ ID NO 14
<211> LENGTH: 20
<212> TYPE: DNA
<213> ORGANISM: Artificial Sequence
<220> FEATURE:
<223> OTHER INFORMATION: Primer 1 for gBlock DNA amplification

<400> SEQUENCE: 14
aggttatgta gtacacattg 20

<210> SEQ ID NO 15
<211> LENGTH: 19

<212> TYPE: DNA
<213> ORGANISM: Artificial Sequence
<220> FEATURE:
<223> OTHER INFORMATION: Primer 2 for gBlock DNA amplification

<400> SEQUENCE: 15
ttaatgccaa ctttgtaca 19

<210> SEQ ID NO 16
<211> LENGTH: 60
<212> TYPE: DNA
<213> ORGANISM: Artificial Sequence
<220> FEATURE:
<223> OTHER INFORMATION: gRNAs Design of the CRISPR/Cas9 system

<400> SEQUENCE: 16
tttttttagg tatatataca aaatatcgtg ctctacaagt ggttttccct acctattagc 60

<210> SEQ ID NO 17
<211> LENGTH: 140
<212> TYPE: DNA
<213> ORGANISM: Artificial Sequence
<220> FEATURE:
<223> OTHER INFORMATION: gRNA construct for cloning and use in CRISPR/
Cas9 system

<400> SEQUENCE: 17
tattaatgcc aactttgtac aagaaagctg ggtctagaaa aaaagcaccg actcggtgcc 60
actttttcaa gttgataacg gactagcctt attttaactt gctatttcta gctctaaaac 120
gctaataggt agggaaaacc 140

<210> SEQ ID NO 18
<211> LENGTH: 60
<212> TYPE: DNA
<213> ORGANISM: Artificial Sequence
<220> FEATURE:
<223> OTHER INFORMATION: gRNA construct for cloning and use in CRISPR/
Cas9 system

<400> SEQUENCE: 18
tttttttagg tatatataca aaatatcgtg ctctacaagt gatgtgacca taaaatctcg 60

<210> SEQ ID NO 19
<211> LENGTH: 140
<212> TYPE: DNA
<213> ORGANISM: Artificial Sequence
<220> FEATURE:
<223> OTHER INFORMATION: gRNA construct for cloning and use in CRISPR/
Cas9 system

<400> SEQUENCE: 19
tattaatgcc aactttgtac aagaaagctg ggtctagaaa aaaagcaccg actcggtgcc 60
actttttcaa gttgataacg gactagcctt attttaactt gctatttcta gctctaaaac 120
cgagatttta tggtcacatc 140

<210> SEQ ID NO 20
<211> LENGTH: 60
<212> TYPE: DNA
<213> ORGANISM: Artificial Sequence
<220> FEATURE:
<223> OTHER INFORMATION: gRNA construct for cloning and use in CRISPR/
Cas9 system

<400> SEQUENCE: 20

-continued tttttttagg tatatataca aaatatcgtg ctctacaagt gcgctgatct ggaacgagtt 60

<210> SEQ ID NO 21
<211> LENGTH: 140
<212> TYPE: DNA
<213> ORGANISM: Artificial Sequence
<220> FEATURE:
<223> OTHER INFORMATION: gRNA construct for cloning and use in CRISPR/ Cas9 system

<400> SEQUENCE: 21
tattaatgcc aactttgtac aagaaagctg ggtctagaaa aaaagcaccg actcggtgcc 60
actttttcaa gttgataacg gactagcctt attttaactt gctatttcta gctctaaaac 120
aactcgttcc agatcagcgc 140

<210> SEQ ID NO 22
<211> LENGTH: 467
<212> TYPE: DNA
<213> ORGANISM: Artificial Sequence
<220> FEATURE:
<223> OTHER INFORMATION: gBlock DNA for silkworm-specific U6 promoter

<400> SEQUENCE: 22
aggttatgta gtacacattg ttgtaaatca ctgaattgtt ttagatgatt ttaacaatta 60
gtacttatta atattaaata agtacatacc ttgagaattt aaaaatcgtc aactataagc 120
catacgaatt taagcttggt acttggctta tagataagga cagaataaga attgttaacg 180
tgtaagacaa ggtcagatag tcatagtgat tttgtcaaag taataacaga tggcgctgta 240
caaaccataa ctgttttcat ttgtttttat ggattttatt acaaattcta aaggttttat 300
tgttattatt taatttcgtt ttaattatat tatatatctt taatagaata tgttaagagt 360
ttttgctctt tttgaataat ctttgtaaag tcgagtgttg ttgtaaatca cgctttcaat 420
agtttagttt ttttaggtat atatacaatt gtacaaagtt ggcatta 467

<210> SEQ ID NO 23
<211> LENGTH: 29
<212> TYPE: DNA
<213> ORGANISM: Artificial Sequence
<220> FEATURE:
<223> OTHER INFORMATION: HC-lacZdisr-Forward

<400> SEQUENCE: 23
atatctagat tctcagtggg tcgcgttac 29

<210> SEQ ID NO 24
<211> LENGTH: 29
<212> TYPE: DNA
<213> ORGANISM: Artificial Sequence
<220> FEATURE:
<223> OTHER INFORMATION: HC-lacZdisr-Reverse

<400> SEQUENCE: 24
ataggtacct cgataactgc cccagatgc 29

<210> SEQ ID NO 25
<211> LENGTH: 1023
<212> TYPE: DNA
<213> ORGANISM: Artificial Sequence
<220> FEATURE:
<223> OTHER INFORMATION: DNA sequence of the MaSp1

<400> SEQUENCE: 25

-continued

```
ggtggtgcag gtcagggtgg ttatggtggt ctgggtagcc agggtgccgg tcgtggtgga     60
ctgggtggtc aaggtgctgg tgcagcagca gctgccgcag cagcaggcgg tgcaggccaa    120
ggcggatatg gcggactggg ttcacagggt gcaggccgtg gcggtttagg tggtcaaggc    180
gcaggcgctg ctgcagccgc agcggcagca gctggccaag gtggctatgg tggcttaggc    240
tcacagggtg gcggtgctgg acagggtgga tacggtggcc ttggcagtca aggtgcgggt    300
cgcggtggtt taggcggtca gggtgcgggt gcggctgctg cagctgcggc agcgggtggt    360
gctgggcaag gcggttacgg tggattaggt agccaaggtg caggacgcgg aggtcttggt    420
ggacagggtg ctggcgctgc tgcggcagca gcagccgctg gggggtgctgg tcaaggggt    480
tatggcggtt taggatctca gggtgcggga cggggtggtc tgggagggca aggggcaggc    540
gcagcagcag cggcagctgc agccggtggt gccggacaag gggatatgg gggtcttggc    600
tcccaaggcg ctggtcgtgg cggtcttgga ggccaaggtg ccggtgccgc tgcagcggct    660
gctgctgcag cgggtcaagg gggatacggt ggtctgggat cacaaggtgg tggcgcaggg    720
caaggtgggt atgggggttt aggttcgcaa ggtgctggcc gtgggggact gggaggacag    780
ggtgccggtg cggcagccgc tgcagctgct gcgggtggcg ctggtcaggg tggctatggc    840
ggattgggct ctcaaggggc aggtcggggt ggcttgggag gacaaggtgc gggtgcagcc    900
gctgcggcag ctgccgctgg cggagcaggc cagggtggct acggtggact gggttcccaa    960
ggtgcgggaa gaggtggctt gggtggccag ggtgcagggg cagcggctgc agcggcagca   1020
gcc                                                                 1023
```

<210> SEQ ID NO 26
<211> LENGTH: 1176
<212> TYPE: DNA
<213> ORGANISM: Artificial Sequence
<220> FEATURE:
<223> OTHER INFORMATION: DNA sequence of the MiSp1

<400> SEQUENCE: 26

```
ggtggtgccg gtggttatgg tcgtggtgct ggtgcgggtg ccggtgcagc agctggtgcc     60
ggtgctggcg caggcggtta tggtggtcag ggtggctacg gtgccggtgc cggtgctggt    120
gccgcagccg cagcgggtgc gggtgcaggc ggtgctggcg gttatggcag aggtgctggg    180
gctggtgcag gcgctgcagc cggtgcgggt gctggtgcgg gtggatatgg tggccagggt    240
ggttatggcg ctggcgcagg ggcaggcgca gcagcagcag ctggggcagg cgcaggcggt    300
gccggtggct atggacgcgg agccggtgcc ggtgcagggg cagcagcggg tgctggtgcc    360
ggtgcagggg gttatggtgg ccaaggcgga tatggtgcgg gtgcaggcgc tggtgcagca    420
gcagccgctg gtgccggtgc cggtggtgcg ggtggctacg gaagaggtgc gggtgccggt    480
gccggtgctg cagcgggtgc gggtgcgggt gccggtggtt atggcggtca gggtgggtat    540
ggtgcgggtg ctggtgcagg cgcagctgca gccgctggtg ctggtgcagg cggagccggt    600
ggatatggcc gaggtgctgg cgcaggcgct ggcgctgctg ctggtgccgg tgcgggtgct    660
gggggatacg gtggtcaagg gggttatggt gcgggtgccg gtgcgggtgc agccgcagca    720
gctggtgcgg gtgcgggtgg tgcaggggga tatggccgtg gtgccggtgc tggtgcgggt    780
gctgcagccg gtgctggggc aggggctggc ggttatgggg gtcaaggcgg ttatggcgct    840
ggtgctggtg ctggggctgc cgcagcagcc ggtgctggtg ctggcggtgc gggtggttac    900
ggtcggggag ctggcgctgg tgctggcgca gcagcgggtg ccggtgctgg tgccggtggc    960
tacggtggac aaggtggcta tggtgccggt gcaggcgcag ggctgcagc cgcagccggt   1020
```

```
gccggtgccg gtggcgctgg gggttatggt cgcggagcgg gtgcaggcgc aggcgcagcc    1080

gctggcgctg gtgcgggtgc tggcggttat ggtggacaag ggggttatgg ggctggtgct    1140

ggcgcagggg cagctgctgc agcgggtgct ggcgct                              1176
```

```
<210> SEQ ID NO 27
<211> LENGTH: 90
<212> TYPE: DNA
<213> ORGANISM: Artificial Sequence
<220> FEATURE:
<223> OTHER INFORMATION: PCR primer for the constructions of
      pSK-NTD-MaSp1/MiSp1(8)-DsRed-CTD vector

<400> SEQUENCE: 27

ataggtacca gccctaacaa gagctcacgt gatagattct atgaagcact tcggtaacgc    60

gacccagtgt tagcaaattc tttcaggttg                                     90
```

```
<210> SEQ ID NO 28
<211> LENGTH: 37
<212> TYPE: DNA
<213> ORGANISM: Artificial Sequence
<220> FEATURE:
<223> OTHER INFORMATION: PCR primer for the constructions of
      pSK-NTD-MaSp1/MiSp1(8)-DsRed-CTD vector

<400> SEQUENCE: 28

taactcgaga gcttgtacag ctcgtccatg ccgagag                              37
```

```
<210> SEQ ID NO 29
<211> LENGTH: 30
<212> TYPE: DNA
<213> ORGANISM: Artificial Sequence
<220> FEATURE:
<223> OTHER INFORMATION: PCR primer for the constructions of
      pSK-NTD-MaSp1/MiSp1(8)-DsRed-CTD vector

<400> SEQUENCE: 29

ataggatccc gcctcctccg agaacgtcat                                      30
```

```
<210> SEQ ID NO 30
<211> LENGTH: 28
<212> TYPE: DNA
<213> ORGANISM: Artificial Sequence
<220> FEATURE:
<223> OTHER INFORMATION: PCR primer for the constructions of
      pSK-NTD-MaSp1/MiSp1(8)-DsRed-CTD vector

<400> SEQUENCE: 30

taatctagac aggaacaggt ggtggcgg                                        28
```

```
<210> SEQ ID NO 31
<211> LENGTH: 33
<212> TYPE: DNA
<213> ORGANISM: Artificial Sequence
<220> FEATURE:
<223> OTHER INFORMATION: PCR primer for the constructions of
      pSK-NTD-MaSp1/MiSp1(8)-DsRed-CTD vector

<400> SEQUENCE: 31

caaccgcgga agcgtcagtt acggagctgg cag                                  33
```

```
<210> SEQ ID NO 32
<211> LENGTH: 37
<212> TYPE: DNA
<213> ORGANISM: Artificial Sequence
```

-continued

<220> FEATURE:
<223> OTHER INFORMATION: PCR primer for the constructions of
pSK-NTD-MaSp1/MiSp1(8)-DsRed-CTD vector

<400> SEQUENCE: 32
taagagctct atagtattct tagttgagaa ggcatac 37

<210> SEQ ID NO 33
<211> LENGTH: 37
<212> TYPE: DNA
<213> ORGANISM: Artificial Sequence
<220> FEATURE:
<223> OTHER INFORMATION: Left genome:junction testing sequence

<400> SEQUENCE: 33
cactagtgct gcagtcgttc tagacgtgag caagggc 37

<210> SEQ ID NO 34
<211> LENGTH: 34
<212> TYPE: DNA
<213> ORGANISM: Artificial Sequence
<220> FEATURE:
<223> OTHER INFORMATION: right genome:junction testing sequence

<400> SEQUENCE: 34
cagctagaac attcaatctg aattcgtcga caag 34

<210> SEQ ID NO 35
<211> LENGTH: 20
<212> TYPE: DNA
<213> ORGANISM: Artificial Sequence
<220> FEATURE:
<223> OTHER INFORMATION: FibH62454-F primer

<400> SEQUENCE: 35
ttgtgatctt gtgctgcgct 20

<210> SEQ ID NO 36
<211> LENGTH: 19
<212> TYPE: DNA
<213> ORGANISM: Artificial Sequence
<220> FEATURE:
<223> OTHER INFORMATION: H1-R primer

<400> SEQUENCE: 36
cagggtcagc ttgccgtag 19

<210> SEQ ID NO 37
<211> LENGTH: 20
<212> TYPE: DNA
<213> ORGANISM: Artificial Sequence
<220> FEATURE:
<223> OTHER INFORMATION: FibH62737-F primer

<400> SEQUENCE: 37
caccggtaaa tcagcattgc 20

<210> SEQ ID NO 38
<211> LENGTH: 20
<212> TYPE: DNA
<213> ORGANISM: Artificial Sequence
<220> FEATURE:
<223> OTHER INFORMATION: FibH-donor-R primer

<400> SEQUENCE: 38
cgactgcagc actagtgctg 20

<210> SEQ ID NO 39
<211> LENGTH: 20
<212> TYPE: DNA
<213> ORGANISM: Artificial Sequence
<220> FEATURE:
<223> OTHER INFORMATION: PSK-F primer

<400> SEQUENCE: 39
gggcgatcgg tgcgggcctc 20

<210> SEQ ID NO 40
<211> LENGTH: 20
<212> TYPE: DNA
<213> ORGANISM: Artificial Sequence
<220> FEATURE:
<223> OTHER INFORMATION: FibH63746-R primer

<400> SEQUENCE: 40
tgagcaacag taccatcgga 20

<210> SEQ ID NO 41
<211> LENGTH: 20
<212> TYPE: DNA
<213> ORGANISM: Artificial Sequence
<220> FEATURE:
<223> OTHER INFORMATION: PSK-F2 primer

<400> SEQUENCE: 41
tacgactcac tatagggcga 20

<210> SEQ ID NO 42
<211> LENGTH: 20
<212> TYPE: DNA
<213> ORGANISM: Artificial Sequence
<220> FEATURE:
<223> OTHER INFORMATION: FibH63575-R primer

<400> SEQUENCE: 42
tcgataactg ccccagatgc 20

<210> SEQ ID NO 43
<211> LENGTH: 30
<212> TYPE: DNA
<213> ORGANISM: Artificial Sequence
<220> FEATURE:
<223> OTHER INFORMATION: Primers for DsRed detection in the genome of transgenic moths

<400> SEQUENCE: 43
ataggatccc gcctcctccg agaacgtcat 30

<210> SEQ ID NO 44
<211> LENGTH: 28
<212> TYPE: DNA
<213> ORGANISM: Artificial Sequence
<220> FEATURE:
<223> OTHER INFORMATION: Primers for DsRed detection in the genome of transgenic moths

<400> SEQUENCE: 44
taatctagac aggaacaggt ggtggcgg 28

<210> SEQ ID NO 45
<211> LENGTH: 20
<212> TYPE: DNA

<213> ORGANISM: Artificial Sequence
<220> FEATURE:
<223> OTHER INFORMATION: Primers for DsRed detection in the genome of
transgenic moths

<400> SEQUENCE: 45
cacgagttcg agatcgaggg 20

<210> SEQ ID NO 46
<211> LENGTH: 20
<212> TYPE: DNA
<213> ORGANISM: Artificial Sequence
<220> FEATURE:
<223> OTHER INFORMATION: Primers for DsRed detection in the genome of
transgenic moths

<400> SEQUENCE: 46
gcgtccacgt agtagtagcc 20

<210> SEQ ID NO 47
<211> LENGTH: 20
<212> TYPE: DNA
<213> ORGANISM: Artificial Sequence
<220> FEATURE:
<223> OTHER INFORMATION: Primers for DsRed detection in the genome of
transgenic moths

<400> SEQUENCE: 47
ccgacatccc cgactacaag 20

<210> SEQ ID NO 48
<211> LENGTH: 20
<212> TYPE: DNA
<213> ORGANISM: Artificial Sequence
<220> FEATURE:
<223> OTHER INFORMATION: Primers for DsRed detection in the genome of
transgenic moths

<400> SEQUENCE: 48
acgccgatga acttcacctt 20

<210> SEQ ID NO 49
<211> LENGTH: 131
<212> TYPE: PRT
<213> ORGANISM: Artificial Sequence
<220> FEATURE:
<223> OTHER INFORMATION: Amino acid sequence of B. mori heavy chain

<400> SEQUENCE: 49

```
Gly Ala Gly Gln Gly Gly Tyr Gly Gly Leu Gly Ser Gln Gly Ala Gly
1               5                   10                  15

Arg Gly Gly Leu Gly Gly Gln Gly Ala Gly Ala Ala Ala Ala Ala Ala
            20                  25                  30

Ala Ala Gly Gly Ala Gly Gln Gly Gly Tyr Gly Gly Leu Gly Ser Gln
        35                  40                  45

Gly Ala Gly Arg Gly Gly Leu Gly Gly Gln Gly Ala Gly Ala Ala Ala
    50                  55                  60

Ala Ala Ala Ala Ala Ala Gly Gln Gly Gly Tyr Gly Gly Leu Gly Ser
65                  70                  75                  80

Gln Gly Gly Gly Ala Gly Gln Gly Gly Tyr Gly Gly Leu Gly Ser Gln
                85                  90                  95

Gly Ala Gly Arg Gly Gly Leu Gly Gly Gln Gly Ala Gly Ala Ala Ala
            100                 105                 110
```

```
Ala Ala Ala Ala Ala Gly Gly Ala Gly Gln Gly Gly Tyr Gly Gly Leu
        115                 120                 125

Gly Ser Gln
    130


<210> SEQ ID NO 50
<211> LENGTH: 138
<212> TYPE: PRT
<213> ORGANISM: Artificial Sequence
<220> FEATURE:
<223> OTHER INFORMATION: Amino acid sequence of the synthetic spider
      silk protein MiSp1

<400> SEQUENCE: 50

Ser Ser Asp Phe Gly Thr Gly Ser Gly Ala Gly Ala Gly Ser Gly Ala
1               5                   10                  15

Gly Ala Gly Ser Gly Ala Gly Ala Gly Ser Gly Ala Gly Ala Gly Ser
            20                  25                  30

Gly Ala Gly Ala Gly Ser Gly Ala Gly Ala Gly Tyr Gly Ala Gly Val
        35                  40                  45

Gly Val Gly Tyr Gly Ala Gly Tyr Gly Ala Gly Ala Gly Ala Gly Tyr
    50                  55                  60

Gly Ala Gly Ala Gly Ser Gly Ala Ala Ser Gly Ala Gly Ala Gly Ser
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

Gly Ala Gly Ala Gly Ser Gly Ala Gly Val
    130                 135


<210> SEQ ID NO 51
<211> LENGTH: 123
<212> TYPE: PRT
<213> ORGANISM: Artificial Sequence
<220> FEATURE:
<223> OTHER INFORMATION: Amino acid sequence of the synthetic spider
      silk protein MiSp1

<400> SEQUENCE: 51

Gly Ala Gly Ala Gly Ala Gly Ala Ala Ala Gly Ala Gly Ala Gly Ala
1               5                   10                  15

Gly Gly Tyr Gly Gly Gln Gly Gly Tyr Gly Ala Gly Ala Gly Ala Gly
            20                  25                  30

Ala Ala Ala Ala Ala Gly Ala Gly Ala Gly Gly Ala Gly Gly Tyr Gly
        35                  40                  45

Arg Gly Ala Gly Ala Gly Ala Gly Ala Ala Ala Gly Ala Gly Ala Gly
    50                  55                  60

Ala Gly Gly Tyr Gly Gly Gln Gly Gly Tyr Gly Ala Gly Ala Gly Ala
65                  70                  75                  80

Gly Ala Ala Ala Ala Ala Gly Ala Gly Ala Gly Gly Ala Gly Gly Tyr
                85                  90                  95

Gly Arg Gly Ala Gly Ala Gly Ala Gly Ala Ala Ala Gly Ala Gly Ala
            100                 105                 110

Gly Ala Gly Gly Tyr Gly Gly Gln Gly Gly Tyr
        115                 120
```

<210> SEQ ID NO 52
<211> LENGTH: 19
<212> TYPE: DNA
<213> ORGANISM: Artificial Sequence
<220> FEATURE:
<223> OTHER INFORMATION: Synthesized sequences of g5 gRNA

<400> SEQUENCE: 52
agaactttaa attatatct 19

<210> SEQ ID NO 53
<211> LENGTH: 19
<212> TYPE: DNA
<213> ORGANISM: Artificial Sequence
<220> FEATURE:
<223> OTHER INFORMATION: Synthesized sequences of g6 gRNA

<400> SEQUENCE: 53
tcactatgag acttaagct 19

<210> SEQ ID NO 54
<211> LENGTH: 31
<212> TYPE: DNA
<213> ORGANISM: Artificial Sequence
<220> FEATURE:
<223> OTHER INFORMATION: Primers used to construct the LC-NHEJ donors

<400> SEQUENCE: 54
ataggtaccc cggttgctca agtgttccac c 31

<210> SEQ ID NO 55
<211> LENGTH: 32
<212> TYPE: DNA
<213> ORGANISM: Artificial Sequence
<220> FEATURE:
<223> OTHER INFORMATION: Primers used to construct the LC-NHEJ donors

<400> SEQUENCE: 55
attgtcgacg tcattaccgt tgccaacgcc tc 32

<210> SEQ ID NO 56
<211> LENGTH: 36
<212> TYPE: DNA
<213> ORGANISM: Artificial Sequence
<220> FEATURE:
<223> OTHER INFORMATION: Primers used to construct the LC-NHEJ donors

<400> SEQUENCE: 56
atagtcgacg tgagcaaggg cgaggagctg ttcacc 36

<210> SEQ ID NO 57
<211> LENGTH: 34
<212> TYPE: DNA
<213> ORGANISM: Artificial Sequence
<220> FEATURE:
<223> OTHER INFORMATION: Primers used to construct the LC-NHEJ donors

<400> SEQUENCE: 57
gcaagcttct tgtacagctc gtccatgccg agag 34

<210> SEQ ID NO 58
<211> LENGTH: 35
<212> TYPE: DNA
<213> ORGANISM: Artificial Sequence
<220> FEATURE:
<223> OTHER INFORMATION: Primers used to construct the LC-NHEJ donors

<400> SEQUENCE: 58
ataggatcct gcgaccggct tagttgctaa tgctc 35

<210> SEQ ID NO 59
<211> LENGTH: 33
<212> TYPE: DNA
<213> ORGANISM: Artificial Sequence
<220> FEATURE:
<223> OTHER INFORMATION: Primers used to construct the LC-NHEJ donors

<400> SEQUENCE: 59
atagagctcg tacccactgt ccaatccacc gtc 33

<210> SEQ ID NO 60
<211> LENGTH: 50
<212> TYPE: DNA
<213> ORGANISM: Artificial Sequence
<220> FEATURE:
<223> OTHER INFORMATION: LC-NHEJ fragment

<400> SEQUENCE: 60
ccaagaactt taaattatat ctacgcgacc atcactatga gacttaagct 50

<210> SEQ ID NO 61
<211> LENGTH: 28
<212> TYPE: DNA
<213> ORGANISM: Artificial Sequence
<220> FEATURE:
<223> OTHER INFORMATION: Primers used for genome: junction testing

<400> SEQUENCE: 61
aagatggatc aaactgcaca cggtgtgc 28

<210> SEQ ID NO 62
<211> LENGTH: 28
<212> TYPE: DNA
<213> ORGANISM: Artificial Sequence
<220> FEATURE:
<223> OTHER INFORMATION: Primers used for genome: junction testing

<400> SEQUENCE: 62
aagagattgt acaactctcg caacagcc 28

<210> SEQ ID NO 63
<211> LENGTH: 21
<212> TYPE: DNA
<213> ORGANISM: Artificial Sequence
<220> FEATURE:
<223> OTHER INFORMATION: Primers used for genome: junction testing

<400> SEQUENCE: 63
gtaaacggcc acaagttcag c 21

<210> SEQ ID NO 64
<211> LENGTH: 20
<212> TYPE: DNA
<213> ORGANISM: Artificial Sequence
<220> FEATURE:
<223> OTHER INFORMATION: Primers used for genome: junction testing

<400> SEQUENCE: 64
tacggcaagc tgaccctgaa 20

<210> SEQ ID NO 65

<211> LENGTH: 20
<212> TYPE: DNA
<213> ORGANISM: Artificial Sequence
<220> FEATURE:
<223> OTHER INFORMATION: Primers used for genome: junction testing

<400> SEQUENCE: 65
gggcgatcgg tgcgggcctc 20

<210> SEQ ID NO 66
<211> LENGTH: 20
<212> TYPE: DNA
<213> ORGANISM: Artificial Sequence
<220> FEATURE:
<223> OTHER INFORMATION: Primers used for genome: junction testing

<400> SEQUENCE: 66
tacgactcac tatagggcga 20

<210> SEQ ID NO 67
<211> LENGTH: 20
<212> TYPE: DNA
<213> ORGANISM: Artificial Sequence
<220> FEATURE:
<223> OTHER INFORMATION: Primers used for genome: junction testing

<400> SEQUENCE: 67
ccaatccacc gtctttgggt 20

<210> SEQ ID NO 68
<211> LENGTH: 24
<212> TYPE: DNA
<213> ORGANISM: Artificial Sequence
<220> FEATURE:
<223> OTHER INFORMATION: Primers used for genome: junction testing

<400> SEQUENCE: 68
gacggtggat tggacagtgg gtac 24

<210> SEQ ID NO 69
<211> LENGTH: 261
<212> TYPE: PRT
<213> ORGANISM: Artificial Sequence
<220> FEATURE:
<223> OTHER INFORMATION: Composite silkworm/spider silk fibers in the G1
LCA group. B. mori light chain

<400> SEQUENCE: 69

```
Met Lys Pro Ile Phe Leu Val Leu Leu Val Ala Thr Ser Ala Tyr Ala
1               5                   10                  15

Ala Pro Ser Val Thr Ile Asn Gln Tyr Ser Asp Asn Glu Ile Pro Arg
            20                  25                  30

Asp Ile Asp Asp Gly Lys Ala Ser Ser Val Ile Ser Arg Arg Trp Asp
        35                  40                  45

Tyr Val Asp Asp Thr Asp Lys Ser Ile Ala Ile Leu Asn Val Gln Glu
    50                  55                  60

Ile Leu Lys Asp Met Ala Ser Gln Gly Asp Tyr Ala Ser Gln Ala Ser
65                  70                  75                  80

Ala Val Ala Gln Thr Ala Gly Ile Ile Ala His Leu Ser Ala Gly Ile
                85                  90                  95

Pro Gly Asp Ala Cys Ala Ala Ala Asn Val Ile Asn Ser Tyr Thr Asp
            100                 105                 110

Gly Val Arg Ser Gly Asn Phe Ala Gly Phe Arg Gln Ser Leu Gly Pro
```

```
        115                 120                 125

Phe Phe Gly His Val Gly Gln Asn Leu Asn Leu Ile Asn Gln Leu Val
    130                 135                 140

Ile Asn Pro Gly Gln Leu Arg Tyr Ser Val Gly Pro Ala Leu Gly Cys
145                 150                 155                 160

Ala Gly Gly Gly Arg Ile Tyr Asp Phe Glu Ala Ala Trp Asp Ala Ile
                165                 170                 175

Leu Ala Ser Ser Asp Ser Ser Phe Leu Asn Glu Glu Tyr Cys Ile Val
            180                 185                 190

Lys Arg Leu Tyr Asn Ser Arg Asn Ser Gln Ser Asn Asn Ile Ala Ala
        195                 200                 205

Tyr Ile Thr Ala His Leu Leu Pro Pro Val Ala Gln Val Phe His Gln
    210                 215                 220

Ser Ala Gly Ser Ile Thr Asp Leu Leu Arg Gly Val Gly Asn Gly Asn
225                 230                 235                 240

Asp Ala Thr Gly Leu Ala Asn Ala Gln Arg Tyr Ile Ala Gln Ala Ala
                245                 250                 255

Ser Gln Val His Val
            260


<210> SEQ ID NO 70
<211> LENGTH: 234
<212> TYPE: PRT
<213> ORGANISM: Artificial Sequence
<220> FEATURE:
<223> OTHER INFORMATION: N. clavipes MaSp1 protein sequence

<400> SEQUENCE: 70

Gly Ala Gly Gln Gly Gly Tyr Gly Gly Leu Gly Ser Gln Gly Ala Gly
1               5                   10                  15

Arg Gly Gly Leu Gly Gly Gln Gly Ala Gly Ala Ala Ala Ala Ala Ala
            20                  25                  30

Ala Ala Gly Gly Ala Gly Gln Gly Gly Tyr Gly Gly Leu Gly Ser Gln
        35                  40                  45

Gly Ala Gly Arg Gly Gly Leu Gly Gly Gln Gly Ala Gly Ala Ala Ala
    50                  55                  60

Ala Ala Ala Ala Ala Ala Gly Gln Gly Gly Tyr Gly Gly Leu Gly Ser
65                  70                  75                  80

Gln Gly Gly Gly Ala Gly Gln Gly Gly Tyr Gly Gly Leu Gly Ser Gln
                85                  90                  95

Gly Ala Gly Arg Gly Gly Leu Gly Gly Gln Gly Ala Gly Ala Ala Ala
            100                 105                 110

Ala Ala Ala Ala Ala Gly Gly Ala Gly Gln Gly Gly Tyr Gly Gly Leu
        115                 120                 125

Gly Ser Gln Gly Ala Gly Arg Gly Gly Leu Gly Gly Gln Gly Ala Gly
    130                 135                 140

Ala Ala Ala Ala Ala Ala Ala Ala Gly Gly Ala Gly Gln Gly Gly Tyr
145                 150                 155                 160

Gly Gly Leu Gly Ser Gln Gly Ala Gly Arg Gly Gly Leu Gly Gly Gln
                165                 170                 175

Gly Ala Gly Ala Ala Ala Ala Ala Ala Ala Ala Gly Gly Ala Gly Gln
            180                 185                 190

Gly Gly Tyr Gly Gly Leu Gly Ser Gln Gly Ala Gly Arg Gly Gly Leu
        195                 200                 205

Gly Gly Gln Gly Ala Gly Ala Ala Ala Ala Ala Ala Ala Ala Ala Gly
```

-continued

```
    210                 215                 220

Gln Gly Gly Tyr Gly Gly Leu Gly Ser Gln
225                 230


<210> SEQ ID NO 71
<211> LENGTH: 604
<212> TYPE: DNA
<213> ORGANISM: Artificial Sequence
<220> FEATURE:
<223> OTHER INFORMATION: Codonoptimized U6 promoter (sU6)
<220> FEATURE:
<221> NAME/KEY: misc_feature
<222> LOCATION: (468)..(487)
<223> OTHER INFORMATION: n is a, c, g, t or u

<400> SEQUENCE: 71

aggttatgta gtacacattg ttgtaaatca ctgaattgtt ttagatgatt ttaacaatta     60

gtacttatta atattaaata agtacatacc ttgagaattt aaaaatcgtc aactataagc    120

catacgaatt taagcttggt acttggctta tagataagga cagaataaga attgttaacg    180

tgtaagacaa ggtcagatag tcatagtgat tttgtcaaag taataacaga tggcgctgta    240

caaaccataa ctgttttcat ttgtttttat ggattttatt acaaattcta aaggttttat    300

tgttattatt taatttcgtt ttaattatat tatatatctt taatagaata tgttaagagt    360

ttttgctctt tttgaataat ctttgtaaag tcgagtgttg ttgtaaatca cgctttcaat    420

agtttagttt ttttaggtat atatacaaaa tatcgtgctc tacaagtnnn nnnnnnnnnn    480

nnnnnnngtt ttagagctag aaatagcaag ttaaaataag gctagtccgt tatcaacttg    540

aaaaagtggc accgagtcgg tgcttttttt ctagacccag ctttcttgta caaagttggc    600

atta                                                                 604
```